US007671179B2

(12) United States Patent
Nicolaides et al.

(10) Patent No.: US 7,671,179 B2
(45) Date of Patent: Mar. 2, 2010

(54) ANTIBODIES AND METHODS FOR GENERATING GENETICALLY ALTERED ANTIBODIES WITH HIGH AFFINITY

(75) Inventors: Nicholas C. Nicolaides, Boothwyn, PA (US); Luigi Grasso, Bala Cynwyd, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 132 days.

(21) Appl. No.: 11/746,868

(22) Filed: May 10, 2007

(65) Prior Publication Data
US 2007/0244302 A1  Oct. 18, 2007

Related U.S. Application Data

(60) Division of application No. 10/243,130, filed on Sep. 13, 2002, now Pat. No. 7,235,643, which is a continuation-in-part of application No. 09/707,468, filed on Nov. 7, 2000, now Pat. No. 6,808,894.

(51) Int. Cl.
C07K 16/18 (2006.01)
(52) U.S. Cl. .................................................. 530/387.3
(58) Field of Classification Search ............... 530/387.3
See application file for complete search history.

(56) References Cited

U.S. PATENT DOCUMENTS

| | | | | |
|---|---|---|---|---|
| 5,530,101 | A | 6/1996 | Queen et al. | 530/387.3 |
| 5,885,827 | A | 3/1999 | Wabl et al. | 435/320.1 |
| 5,907,079 | A | 5/1999 | Mak et al. | 800/2 |
| 6,146,894 | A | 11/2000 | Nicolaides et al. | 435/440 |
| 6,191,268 | B1 | 2/2001 | Liskay et al. | 536/23.5 |
| 6,287,862 | B1 | 9/2001 | delCardayre et al. | 435/440 |
| 6,808,894 | B1 | 10/2004 | Nicolaides et al. | 435/69.1 |
| 2003/0143682 | A1 | 7/2003 | Nicolaides et al. | 435/69.1 |

FOREIGN PATENT DOCUMENTS

| | | |
|---|---|---|
| CA | 2240609 | 10/1999 |
| JP | 1994327479-A/2 | * 11/1994 |
| WO | WO 97/05268 | 2/1997 |
| WO | WO 99/19492 | 4/1999 |
| WO | WO 02/37967 A1 | 5/2002 |
| WO | WO 02/054856 | 7/2002 |
| WO | 2004/024871 A2 | 3/2004 |
| WO | WO2004/002487 A2 | 3/2004 |
| WO | WO2005/011735 A1 | 2/2005 |

OTHER PUBLICATIONS

Czerwinski et al. (Mol. Immunol. Mar. 1994; 31 (4): 279-288).*
Mertens et al. (Mol. Immunol. Oct. 2000; 37 (15): 901-913).*
GENEMBL Accession No. AF163747.1 (GI:5690300).*
Allen, D., et al., "MutS mediates heteroduplex loop formation by a translocation mechanism," *EMBO J.*, 1997, 16(14), 4467-4476.
Baker, S.M., et al., "Male mice defective in the DNA mismatch repair gene PMS2 exhibit abnormal chromosome synapsis in meiosis," *Cell*, 1995, 82, 309-319.
Bell, C.J., et al., "Assignment of 30 microsatellite loci to the linkage map of *arabidopsis*," *Enomics*, 1994, 19, 137-144.
Bignami M., "Unmasking a Killer: DNA $O^6$-methylguanine and the Cytotoxicity of Methylating Agents", *Mutat. Res.*, 2000, 462, 71-82.
Bjornson, K., et al., "Modulation of MutS ATP hydrolysis by DNA cofactors," *Biochemistry*, 2000, 39, 3176-3183.
Bronner C.E., et al., "Mutation in the DNA mismatch repair gene homologue hMLH1 is associated with hereditary non-polyposis colon cancer," *Nature*, 1994, 368, 258-261.
Chakravarti, D. et al., "Relating aromatic hydrocarbon-induced DNA adducts and c-H-*ras* mutations in mouse skin papillomas: The role of apurinic sites", *Proc. Natl. Acad. Sci. USA*, Oct. 1995, vol. 92, pp. 10422-10426.
de Wind, N., et al., "Inactivation of the mouse Msh2 gene results in mismatch repair deficiency, methylation tolerance, hyperrecombination, and predisposition to cancer," *Cell*, 1995, 82, 321-330.
Drummond, J.T., et al., "Isolation of an hMSH2-p160 heterodimer that restores DNA mismatch repair to tumor cells," *Science*, 1995, 268, 1909-1912.
Drummond, J.T., et al., "Cisplatin and adriamycin resistance are associated with mutlα and mismatch repair deficiency in an ovarian tumor cell line," *J. Biological Chemistry*, 1996, 271(33), 19645-19648.
Edelmann, W., et al., "Meiotic pachytene arrest in MLH1-deficient mice," *Cell*, 1996, 85, 1125-1134.
Emery, S.C. and Harris, W.J., "Strategies for Humanizing Antibodies" In C.A.K. Borrebaeck (Ed.), Antibody Engineering. Oxford University Press, N.Y. 1995; pp. 159-183.
Eshleman, J.R., et al., "Mismatch repair defects in human carcinogenesis," *Human Molecular Genetics*, 1996, 5, 1489-1494.
Fiedler, U. et al., "High-Level Production and Long-Term Storage of Engineered Antibodies in Transgenic Tobacco Seeds", *Bio/Technology*, 1995, 13, 1090-1093.
Frigerio, L. et al., "Assembly, Secretion, and Vacuolar Delivery of a Hybrid Immunoglobin in Plants", *Plant Physiol*, 2000, 123, 1483-1494.
Galio, L., et al., "ATP hydrolysis-dependent formation of a dynamic ternary nucleoprotein complex with MutS and MutL," *Nucleic Acids Research*, 1999, 27(11), 2325-2331.
Glaser, V., "Gene Therapy's Other Investment Window", *Nat. Biotechnol.*, 1996, 14, 1216-1217.
Harfe, B.D., "DNA mismatch repair and genetic instability," *Annu. Rev. Genet.*, 2000, 34, 359-399.

(Continued)

*Primary Examiner*—Stephen L Rawlings
(74) *Attorney, Agent, or Firm*—Woodcock Washburn, LLP

(57) ABSTRACT

Dominant negative alleles of human mismatch repair genes can be used to generate hypermutable cells and organisms. By introducing these genes into cells and transgenic animals, new cell lines and animal varieties with novel and useful properties can be prepared more efficiently than by relying on the natural rate of mutation. These methods are useful for generating genetic diversity within immunoglobulin genes directed against an antigen of interest to produce altered antibodies with enhanced biochemical activity. Moreover, these methods are useful for generating antibody-producing cells with increased level of antibody production. The invention also provides methods for increasing the affinity of monoclonal antibodies and monoclonal antibodies with increased affinity.

5 Claims, 7 Drawing Sheets

OTHER PUBLICATIONS

Hoang J., et al., "BAT-26, an Indicator of the Replication Error Phenotype in Colorectal Cancers and Cell Lines", *Cancer Res.*, 1997, 57, 300-303.

Honma, M. et al., "Cytotoxic and Mutagenic Responses to X-rays and Chemical Mutagens in Normal and p53-mutated Human Lymphoblastoid Cells", *Mut. Res.*, 1997, 374, 89-98.

Jiricny, J., et al., "Mismatch repair defects in cancer," *Curr. Opin. Genet. Dev.*, 2000, 10, 157-161.

Karran, P., et al., "Genomic instability and tolerance to alkylating agents," *Cancer Surveys*, 1996, 28, 69-71.

Khazaeli, M.B. et al., "Human Immune Response to Monoclonal Antibodies", *J. Immunother.*, 1994, 15, 42-52.

Kong, Q., et al., "PMS2-deficiency diminishes hypermutation of a lamdal transgene in young but not older mice", *Mol. Immunol.*, 1999, 36, 83-91.

Liu, T., et al., "Microsatellite instability as a predictor of a mutation in a DNA mismatch repair gene in familial colorectal cancer," *Genes, Chromosomes & Cancer*, 2000, 27, 17-25.

Liu et al., "Analysis of Mismatch Repair Genes in Hereditary Nonpolyposis Colorectal Cancer Patients", *Nature Medicine*, Feb. 1996, 2(2), 169-174.

Leach, F.S., et al., "Mutations of a mutS homolog in hereditary nonpolyposis colorectal cancer," *Cell*, 1993, 75, 1215-1225.

Ma et al., "Dominant Negative Expression of hPMS2 Creates Isogenic Mismatch Repair Deficient Human Colon Cancer Cell Lines", *Proc. Am. Assoc. Cancer Res.*, Mar. 1998, 39, p. 460 (Abstract #3130).

McCallum, C.M., "Targeted screening for induced mutations," *Nature Biotechnology*, 2000, 18, 455-457.

Modrich, P., "Mismatch repair, genetic stability, and cancer," *Science*, 1994, 266, 1959-1960.

Neuberger, M., et al., "Mice perform a human repertoire," *Nature*, 1997, 386, 25-26.

Nicolaides, N.C., et al., "The jun family members, c-jun and junD, transactivate the human c-*myb*, promotor via an Ap1-like element," *J. Biological Chemistry*, 1992, 267(27), 19665-19672.

Nicolaides, N.C., et al., "Genomic organization of the human *PMS2* gene family," *Genomics*, 1995, 30, 195-206.

Nicolaides, N.C., et al., "Positive autoregulation of c-*myb*, expression via Myb binding sites in the 5' flanking region of the human c-*myb* gene," *Moecular and Cellular Biology*, 1991, 11(12), 6166-6176.

Nicolaides, N.C., "A naturally occurring *hPMS2* mutation can confer a dominant negative nutator phenotype," *Mol. Cell. Biol.*, 1998, 18(3), 1635-1641.

Nicolaides, N.C., et al., "Analysis of the 5' region of *PMS2* reveals heterogeneous transcripts and a novel overlapping gene," *Genomics*, 1995, 29, 329-334.

Nicolaides, N.C., et al., "Mutations of two PMS homologues in hereditary nonpolyposis colon cancer," *Nature*, 1994, 371, 75-80.

Palombo, F., et al., "Mismatch repair and cancer," *Nature*, 1994, 367, 417.

Papadopoulos, N., et al., "Mutation of a *mutL* homolog in hereditary colon cancer," *Science*, 1993, 263, 1625-1629.

Papadopoulos, N., et al., "Mutations of *GTBP* in genetically unstable cells," *Science*, 1995, 268, 1915-1917.

Parsons, R., et al., "Hypermutability and mismatch repair deficiency in RER+ tumor cells," *Cell*, 1993, 75, 1227-1236.

Peinado, M.A., et al., "Isolation and characterization of allelic lossesand gains in colorectal tumors by arbitrarily primed polymerase chain reaction," *Proc. Natl. Acad. Sci. USA*, 1992, 89, 10065-10069.

Perucho, M., et al., "Cancer of the microsatellite mutator phenotype," *Biol. Chem.*, 1996, 377, 675-684.

Prolla, T.A., et al., "MLH1, PMS1, and MSH2 interactions during the initiation of DNA mismatch repair in yeast," *Science*, 1994, 265, 1091-1093.

Quian, Y. et al., "Molecular events after antisense inhibition of hMSH2 in a HeLa cell line", *Mutation Research*, Oct. 12, 1998, vol. 418, pp. 61-71.

Reff, M.E., "High-level production of recombinant immunoglobulins in mammalian cells", *Curr. Opin. Biotechnol.*, 1993, 4, 573-576.

Saez-Llorens, X.E. et al., "Safety and pharmacokinetics of an intramuscular humanized monoclonal antibody to respiratory syncytial virus in premature infants and infants with bronchopulmonary dysplasia", *Pediat. Infect. Dis. J.*, 1998, 17(9), 787-791.

Schrader, C.E. et al., "Reduced Isotype Switching in Splenic B Cells from Mice Deficient in Mismatch Repair Enzymes", *Journal of Experimental Medicine*, 1999, 190(3), 323-330.

Shield, C.F. et al., "A Cost-Effectiveness Analysis of OKT3 Induction Therapy in Cadaveric Kidney Transplantation", *Am. J. Kidney Dis.*, 1996, 27, 855-864.

Shields, R.L. et al., "Anti-IgE Monoclonal Antibodies that Inhibit Allergen-Specific Histamine Release", *Int. Arch. Allergy Immunol.*, 1995, 107, 412-413.

Spampinato, C., et al., "The MutL ATPase is required for mismatch repair," *J. Biological Chemistry*, 2000, 275(13), 9863-9869.

Strand, M., et al., "Destabilization of tracts of simple repetitive DNA in yeast by mutations affecting DNA mismatch repair," *Nature*, 1993, 365, 274-276.

Su, S., et al., "Mispair specificity of methyl-directed DNA mismatch correction In Vitro," *J. Biological Chemistry*, 1988, 263(14), 6829-6835.

Vora, K.A. et al., "Severe Attenuation of the B Cell Immune Response in Msh2-deficient Mice", *Journal of Experimental Medicine*, Feb. 1999, 189(3), 471-481.

Wheeler, J.M.D., et al., "The role of hypermethylation of the *hMLH1* promoter region in HNPCC verus MSI+sporadic colorectal cancers," *J. Med. Genet.*, 2000, 588-592.

Weiner, L.M., "Monoclonal Antibody Therapy of Cancer", *Semin. Oncol.*, Oct. 1999, vol. 26, No. 5, Suppl. 14, pp. 43-51.

Winter, D.B. et al., "Altered spectra of hypermutation in antibodies from mice deficient for the DNA mismatch repair protein PMS2", *Proc. Natl. Acad. Sci.*, USA, Jun. 1998, 95, 6953-6958.

Yu, Y. et al., "Adriamycin induces large deletions as a major type of mutation in CHO cells", *Mutation Research*, Nov. 1994, vol. 325, pp. 91-98.

Anderson "Human gene therapy," *Nature*, 1998, 392, 25-30.

Aronshtam, A., et al., "Dominant negative mutator mutations in the mutl gene of *Escherichia coli*," *Nucleic Acids Res.*, 1996, 24(13), 2498-2504.

Bishop, J., "Chromosomal insertion of foreign DNA," *Reproductive Nutrition & Development*, 1996, 36, 607-619.

Caldas, C., et al., "Humanization of the anti-CD18 antibody 6.7: an unexpected effect of a framework residue in binding to antigen," *Molecular Immunology*, 2003, 39, 941-952.

Chien, N.C., et al., "Significant structural and functional change of an antigen-binding site by a distant amino acid substitution: proposal of a structural mechanism," Proc. Natl. Acad. Sci. USA, 1989, 86, 5532-5536.

Crameri, A., et al., "Combinatorial multiple cassette mutagenesis creates all the permutations of mutant and wild-type sequences," *BioTechniques*, 1995, 18(2), 194-196.

Cascalho, M., et al., "Mismatch repair co-opted by hypermutation," *Science*, 1998, 279(20), 1207-1210.

Coia, G. et al., "Protein affinity maturation in vivo using *E. coli* mutator cells," *J Immunol Methods* (2001) 251:187-193.

Culligan, K.M., et al., "DNA mismatch repair in plants," *Plant Physiol.*, 1997, 15, XP-002099372, 833-839.

Giusti, A.M., "Somatic diversification of S107 from an antiphosphocholine to an anti-DNA autoantibody is due to a single base change in its heavy chain variable region," Phoc. Natl. Acad. Sci. USA, 1987, 84, 2926-2930.

Irving, R.A., "Affinity maturation of recombinant antibodies using *E. coli* mutator cells," *Immunotechnology 2*, 1996, 127-143.

Jean, M., et al., "Isolation and characterization of *AtMLH1*, a *MutL* homologue from *Arabidopsis thaliana*," *Mol. Gen. Genet.*, 1999, 262, XP-000986138, 633-642.

Jung, S., et al., "The importance of framework residues H6, H7 and H10 in antibody heavy chains: experimental evidence for a new structural subclassification of antibody $V_H$ domains," J. Mol. Biol., 2001, 309, 701-716.

Kipriyanov, S., et al., "Two amino acid mutations in an anti-human CD3 single chain Fv antibody fragment that affect the yield on bacterial secretion but not the affinity," Protein Engineering, 10(4), 445-453.

Kunkel, T.A., et al., "Efficient site-directed mutagenesis using uracil-containing DNA," *Methods Enzymol.*, 1991, 204, 125-139.

Li, Y. et al., "Three-Dimensional Structures of the Free and Antigen-Bound Fab from Monoclonal Antilysozyme Antibody HyHEL-63," *Biochemistry* (2000) 39:6296-6309.

Lipkin, S.M., et al., "MLH3: a DNA mismatch repair gene associated with mammalian microsatellite instability," *Nature Genetics*, 2000, 24, XP-002165243, 27-35.

Low, N.M. et al., "Mimicking Somatic Hypermutation: Affinity Maturation of Antibodies Displayed on Bacteriophage Using a Bacterial Mutator Strain," *J Mol Biol* (1996) 260:359-368.

Ngo, et al., Computational complexity, protein structure prediction, and the levinthal paradox, 1994, 491-495.

Nicolaides, N.C., et al., "*Morphogenics* as a tool for target discovery and drug development," *Ann. N.Y. Acad. Sci.*, 2005, 1059, 86-95 (Reprinted from Tumor Progression and Therapeutic Resistance, vol. 1059 of the Annals of the N.Y. Acad. Sci., Nov. 2005).

Polaczek, P., et al., "Functional genetic tests of DNA mismatch repair protein activity in *Saccharomyces cerevisiae*," Gene, 1998, 213(1-2), 159-167.

Polejaeva, et al., New advances in somatic cell nuclear transfer application in transgenesis, 2000, 117-126.

Reynaud, C.-A., et al., "Mismatch repair and immunoglobulin gene hypermutation: did we learn something?," *Immunology Today*, 1999, 20(11), 522-527.

Rulicke, et al., Special review series-gene manipulation and integrative physiology, Exp. Physiology, 2000, 85(6), 589-601.

Russell, et al., "Structural features can be unconserved in proteins with similar folds," 1994, 332-350.

Tan, P.H., et al., "Contributions of a highly conserved $V_H/V_L$ hydrogen bonding interaction to scFv folding stability and refolding efficiency," Biophysical J., 1998, 75, 1473-1482.

Verma, et al., "Gene therapy promises, problems and prospects," 1997, 389, 239-242.

Wabl, M. et al., "Hypermutation in antibody affinity maturation," *Curr Opin Immunol* (1999) 11:186-189.

Wiesendanger, M., et al., "Somatic hypermutation, transcription, and DNA mismatch repair," *Cell*, 1998, 94, 415-418.

Xiang, J., et al., "Framework residues 71 and 93 of the chimeric B72.3 antibody are major determinants of the conformation of heavy-chain hypervariable loops," J. Mol. Biol., 1995, 253, 385-390.

Xiang, J., et al., "Light-chain framework region residue Tyr71 of chimeric B72.3 antibody plays an important role in influencing the TAG72 antigen binding," 1999, 12(5), 417-421.

Bockamp, E., et al., "Of mice and models: improved animal models for biomedical research," Physiol. Genomics, 2001, 11, 115-132.

Bork, P., "Powers and pitfalls in sequence analysis: the 70% hurdle," Genome esearch, 2000, 10, 398-400.

Bork, P., "Go hunting in sequence databases but watch out for traps," *Trends in Genetics*, 1996, 12(10), 425-427.

Brenner, S.E., "Errors in genome annotation," *Trends in Genetics*, 1999, 15(4), 132-133.

Goncalves, M.A.F.V., "A concise peer into the background, initial thoughts and practices of human gene therapy," BioEssays, 2005, 27, 506-517.

Haught, C., et al., "A method to insert a DNA fragment into a double-stranded plasmid," *BioTechniques*, 1994, 16(1), 47-48.

Holschneider, D.P., et al., "Genotype to phenotype: challenges and opportunities," Int. J. Devl. Neuroscience, 2000, 18, 615-618.

Muramatsu, M., et al., "Class switch recombination and jypermutation require activation-induced cytidine deaminase (AID), a potential RNA editing enzyme," Cell, 2000, 102, 553-563.

Parsons, R., et al., "Mismatch repair deficiency in phenotypically normal human cells," Science, 1995, 268, 738-740.

Green, N.S. et al., "Immunoglobulin hypermutation in cultured cells," Immunol. Rev., 1998, 162, 77-87.

* cited by examiner

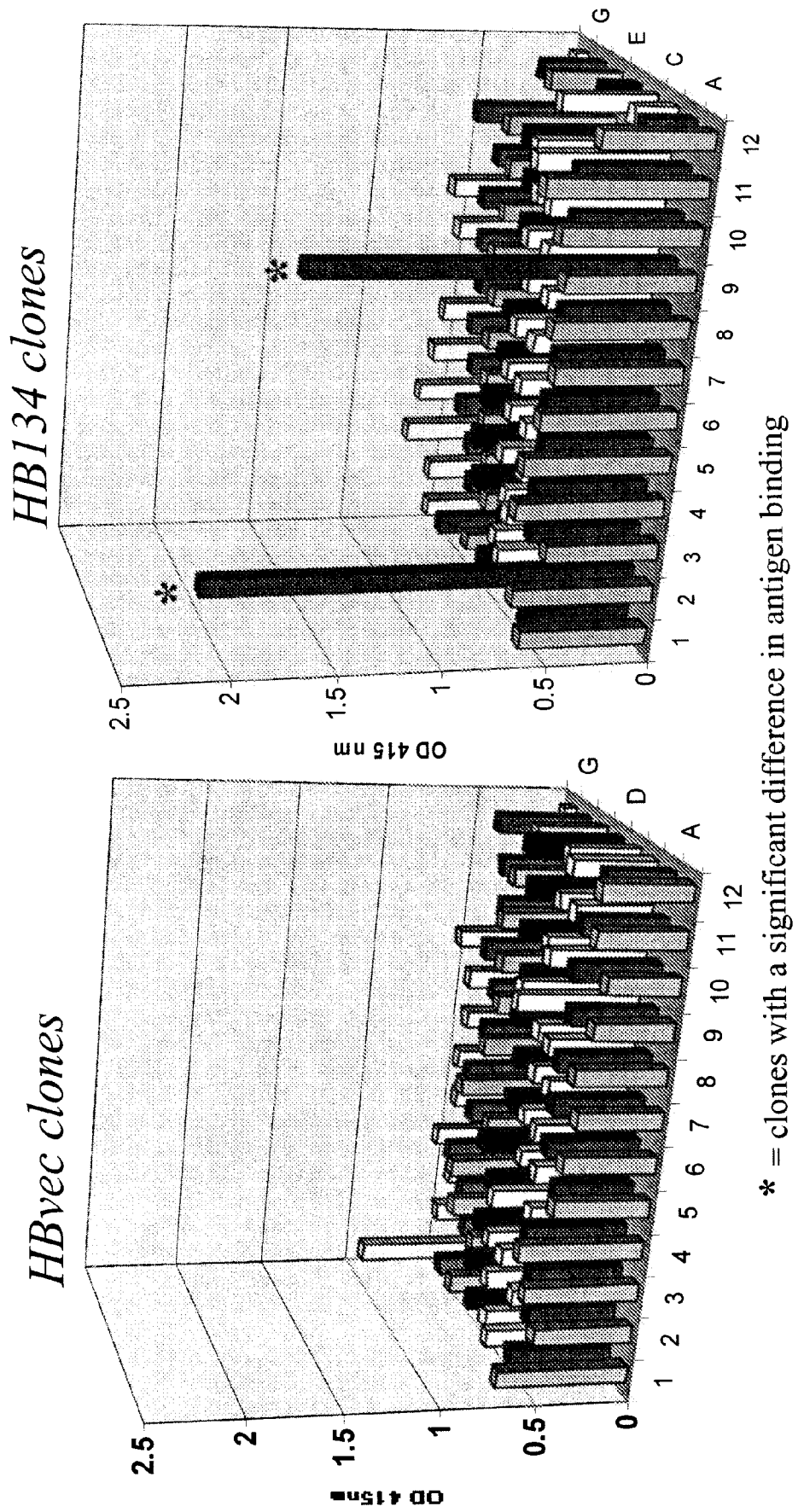

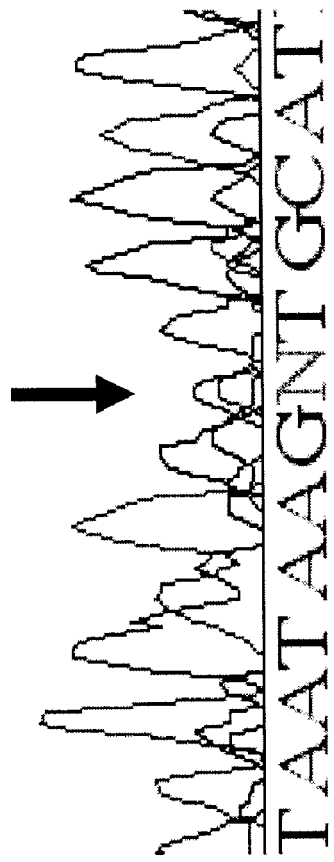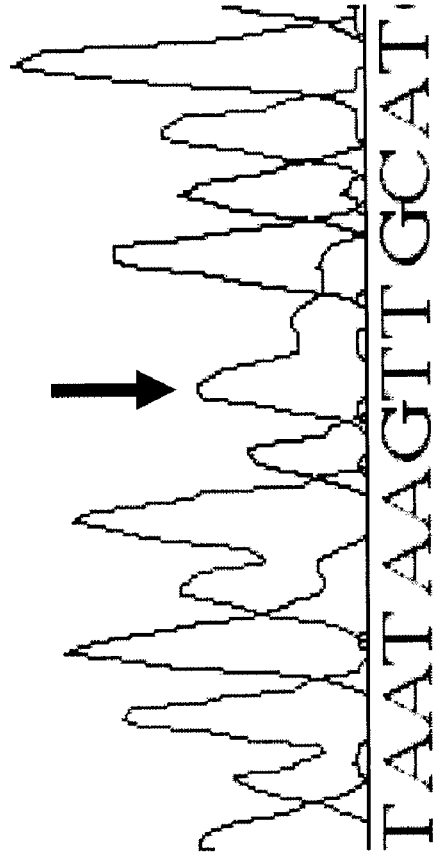
Fig. 5A

ANTIBODIES AND METHODS FOR GENERATING GENETICALLY ALTERED ANTIBODIES WITH HIGH AFFINITY

CROSS-REFERENCE TO RELATED APPLICATIONS

This application is a divisional application of U.S. Nonprovisional application Ser. No. 10/243,130, filed Sep. 13, 2002, which is a continuation-in-part of U.S. application Ser. No. 09/707,468, filed Nov. 7, 2000, the disclosures of which are hereby incorporated by reference in their entireties.

TECHNICAL FIELD OF THE INVENTION

The invention is related to the area of antibody maturation and cellular production. In particular, it is related to the field of mutagenesis.

BACKGROUND OF THE INVENTION

The use of antibodies to block the activity of foreign and/or endogenous polypeptides provides an effective and selective strategy for treating the underlying cause of disease. In particular is the use of monoclonal antibodies (MAb) as effective therapeutics such as the FDA approved ReoPro (Glaser, V. (1996) Can ReoPro repolish tarnished monoclonal therapeutics? *Nat. Biotechnol.* 14:1216-1217), an anti-platelet MAb from Centocor; Herceptin (Weiner, L. M. (1999) Monoclonal antibody therapy of cancer. *Semin. Oncol.* 26:43-51), an anti-Her2/neu MAb from Genentech; and Synagis (Saez-Llorens, X. E., et al. (1998) Safety and pharmacokinetics of an intramuscular humanized monoclonal antibody to respiratory syncytial virus in premature infants and infants with bronchopulmonary dysplasia. *Pediat. Infect. Dis. J.* 17:787-791), an anti-respiratory syncytial virus MAb produced by Medimmune.

Standard methods for generating MAbs against candidate protein targets are known by those skilled in the art. Briefly, rodents such as mice or rats are injected with a purified antigen in the presence of adjuvant to generate an immune response (Shield, C. F., et al. (1996) A cost-effective analysis of OKT3 induction therapy in cadaveric kidney transplantation. *Am. J. Kidney Dis.* 27:855-864). Rodents with positive immune sera are sacrificed and splenocytes are isolated. Isolated splenocytes are fused to melanomas to produce immortalized cell lines that are then screened for antibody production. Positive lines are isolated and characterized for antibody production. The direct use of rodent MAbs as human therapeutic agents were confounded by the fact that human anti-rodent antibody (HARA) responses occurred in a significant number of patients treated with the rodent-derived antibody (Khazaeli, M. B., et al., (1994) Human immune response to monoclonal antibodies. *J. Immunother.* 15:42-52). In order to circumvent the problem of HARA, the grafting of the complementarity determining regions (CDRs), which are the critical motifs found within the heavy and light chain variable regions of the immunoglobulin (Ig) subunits making up the antigen binding domain, onto a human antibody backbone found these chimeric molecules are able to retain their binding activity to antigen while lacking the HARA response (Emery, S. C., and Harris, W. J. "Strategies for humanizing antibodies" In: ANTIBODY ENGINEERING C.A.K. Borrebaeck (Ed.) Oxford University Press, N.Y. 1995. pp. 159-183. A common problem that exists during the "humanization" of rodent-derived MAbs (referred to hereon as HAb) is the loss of binding affinity due to conformational changes in the 3 dimensional structure of the CDR domain upon grafting onto the human Ig backbone (U.S. Pat. No. 5,530,101 to Queen et al.). To overcome this problem, additional HAb vectors are usually needed to be engineered by inserting or deleting additional amino acid residues within the framework region and/or within the CDR coding region itself in order to recreate high affinity HAbs (U.S. Pat. No. 5,530,101 to Queen et al). This process is a very time consuming procedure that involves the use of expensive computer modeling programs to predict changes that may lead to a high affinity HAb. In some instances the affinity of the HAb is never restored to that of the MAb, rendering them of little therapeutic use.

Another problem that exists in antibody engineering is the generation of stable, high yielding producer cell lines that is required for manufacturing of the molecule for clinical materials. Several strategies have been adopted in standard practice by those skilled in the art to circumvent this problem. One method is the use of Chinese Hamster Ovary (CHO) cells transfected with exogenous Ig fusion genes containing the grafted human light and heavy chains to produce whole antibodies or single chain antibodies, which are a chimeric molecule containing both light and heavy chains that form an antigen-binding polypeptide (Reff, M. E. (1993) High-level production of recombinant immunoglobulins in mammalian cells. *Curr. Opin. Biotechnol.* 4:573-576). Another method employs the use of human lymphocytes derived from transgenic mice containing a human grafted immune system or transgenic mice containing a human Ig gene repertoire. Yet another method employs the use of monkeys to produce primate MAbs, which have been reported to lack a human anti-monkey response (Neuberger, M., and Gruggermann, M. (1997) Monoclonal antibodies. Mice perform a human repertoire. *Nature* 386:25-26). In all cases, the generation of a cell line that is capable of generating sufficient amounts of high affinity antibody poses a major limitation for producing sufficient materials for clinical studies. Because of these limitations, the utility of other recombinant systems such as plants are currently being explored as systems that will lead to the stable, high-level production of humanized antibodies (Fiedler, U., and Conrad, U. (1995) High-level production and long-term storage of engineered antibodies in transgenic tobacco seeds. *Bio/Technology* 13:1090-1093).

A method for generating diverse antibody sequences within the variable domain that results in HAbs and MAbs with high binding affinities to antigens would be useful for the creation of more potent therapeutic and diagnostic reagents respectively. Moreover, the generation of randomly altered nucleotide and polypeptide residues throughout an entire antibody molecule will result in new reagents that are less antigenic and/or have beneficial pharmacokinetic properties. The invention described herein is directed to the use of random genetic mutation throughout an antibody structure in vivo by blocking the endogenous mismatch repair (MMR) activity of a host cell producing immunoglobulins that encode biochemically active antibodies. The invention also relates to methods for repeated in vivo genetic alterations and selection for antibodies with enhanced binding and pharmacokinetic profiles.

In addition, the ability to develop genetically altered host cells that are capable of secreting increased amounts of antibody will also provide a valuable method for creating cell hosts for product development. The invention described herein is directed to the creation of genetically altered cell hosts with increased antibody production via the blockade of MMR.

The invention facilitates the generation of high affinity antibodies and the production of cell lines with elevated levels of antibody production. Other advantages of the present invention are described in the examples and figures described herein.

SUMMARY OF THE INVENTION

The invention provides methods for generating genetically altered antibodies (including single chain molecules) and antibody producing cell hosts in vitro and in vivo, whereby the antibody possess a desired biochemical property(s), such as, but not limited to, increased antigen binding, increased gene expression, and/or enhanced extracellular secretion by the cell host. One method for identifying antibodies with increased binding activity or cells with increased antibody production is through the screening of MMR defective antibody producing cell clones that produce molecules with enhanced binding properties or clones that have been genetically altered to produce enhanced amounts of antibody product.

The antibody producing cells suitable for use in the invention include, but are not limited to rodent, primate, or human hybridomas or lymphoblastoids; mammalian cells transfected and expressing exogenous Ig subunits or chimeric single chain molecules; plant cells, yeast or bacteria transfected and expressing exogenous Ig subunits or chimeric single chain molecules.

Thus, the invention provides methods for making hypermutable antibody-producing cells by introducing a polynucleotide comprising a dominant negative allele of a mismatch repair gene into cells that are capable of producing antibodies. The cells that are capable of producing antibodies include cells that naturally produce antibodies, and cells that are engineered to produce antibodies through the introduction of immunoglobulin encoding sequences. Conveniently, the introduction of polynucleotide sequences into cells is accomplished by transfection.

The invention also provides methods of making hypermutable antibody producing cells by introducing a dominant negative mismatch repair (MMR) gene such as PMS2 (preferably human PMS2), MLH1, PMS1, MSH2, or MSH2 into cells that are capable of producing antibodies. The dominant negative allele of a mismatch repair gene may be a truncation mutation of a mismatch repair gene (preferably a truncation mutation at codon 134, or a thymidine at nucleotide 424 of wild-type PMS2). The invention also provides methods in which mismatch repair gene activity is suppressed. This may be accomplished, for example, using antisense molecules directed against the mismatch repair gene or transcripts.

Other embodiments of the invention provide methods for making hypermutable antibody producing cells by introducing a polynucleotide comprising a dominant negative allele of a mismatch repair gene into fertilized eggs of animals. These methods may also include subsequently implanting the eggs into pseudo-pregnant females whereby the fertilized eggs develop into a mature transgenic animal. The mismatch repair genes may include, for example, PMS2 (preferably human PMS2), MLH1, PMS1, MSH2, or MSH2. The dominant negative allele of a mismatch repair gene may be a truncation mutation of a mismatch repair gene (preferably a truncation mutation at codon 134, or a thymidine at nucleotide 424 of wild-type PMS2).

The invention further provides homogeneous compositions of cultured, hypermutable, mammalian cells that are capable of producing antibodies and contain a dominant negative allele of a mismatch repair gene. The mismatch repair genes may include, for example, PMS2 (preferably human PMS2), MLH1, PMS1, MSH2, or MSH2. The dominant negative allele of a mismatch repair gene may be a truncation mutation of a mismatch repair gene (preferably a truncation mutation at codon 134, or a thymidine at nucleotide 424 of wild-type PMS2). The cells of the culture may contain PMS2 (preferably human PMS2), MLH1, or PMS1; or express a human mutL homolog, or the first 133 amino acids of hPMS2.

The invention further provides methods for generating a mutation in an immunoglobulin gene of interest by culturing an immunoglobulin producing cell selected for an immunoglobulin of interest wherein the cell contains a dominant negative allele of a mismatch repair gene. The properties of the immunoglobulin produced from the cells can be assayed to ascertain whether the immunoglobulin gene harbors a mutation. The assay may be directed to analyzing a polynucleotide encoding the immunoglobulin, or may be directed to the immunoglobulin polypeptide itself.

The invention also provides methods for generating a mutation in a gene affecting antibody production in an antibody-producing cell by culturing the cell expressing a dominant negative allele of a mismatch repair gene, and testing the cell to determine whether the cell harbors mutations within the gene of interest, such that a new biochemical feature (e.g., over-expression and/or secretion of immunoglobulin products) is generated. The testing may include analysis of the steady state expression of the immunoglobulin gene of interest, and/or analysis of the amount of secreted protein encoded by the immunoglobulin gene of interest. The invention also embraces prokaryotic and eukaryotic transgenic cells made by this process, including cells from rodents, non-human primates and humans.

Other aspects of the invention encompass methods of reversibly altering the hypermutability of an antibody-producing cell, in which an inducible vector containing a dominant negative allele of a mismatch repair gene operably linked to an inducible promoter is introduced into an antibody-producing cell. The cell is treated with an inducing agent to express the dominant negative mismatch repair gene (which can be PMS2 (preferably human PMS2), MLH1, or PMS1). Alternatively, the cell may be induced to express a human mutL homolog or the first 133 amino acids of hPMS2. In another embodiment, the cells may be rendered capable of producing antibodies by co-transfecting a preselected immunoglobulin gene of interest. The immunoglobulin genes of the hypermutable cells, or the proteins produced by these methods may be analyzed for desired properties, and induction may be stopped such that the genetic stability of the host cell is restored.

The invention also embraces methods of producing genetically altered antibodies by transfecting a polynucleotide encoding an immunoglobulin protein into a cell containing a dominant negative mismatch repair gene (either naturally or in which the dominant negative mismatch repair gene was introduced into the cell), culturing the cell to allow the immunoglobulin gene to become mutated and produce a mutant immunoglobulin, screening for a desirable property of said mutant immunoglobulin protein, isolating the polynucleotide molecule encoding the selected mutant immunoglobulin possessing the desired property, and transfecting said mutant polynucleotide into a genetically stable cell, such that the mutant antibody is consistently produced without further genetic alteration. The dominant negative mismatch repair gene may be PMS2 (preferably human PMS2), MLH1, or PMS1. Alternatively, the cell may express a human mutL homolog or the first 133 amino acids of hPMS2.

The invention further provides methods for generating genetically altered cell lines that express enhanced amounts of an antigen binding polypeptide. These antigen-binding polypeptides may be, for example, immunoglobulins. The methods of the invention also include methods for generating genetically altered cell lines that secrete enhanced amounts of an antigen binding polypeptide. The cell lines are rendered hypermutable by dominant negative mismatch repair genes that provide an enhanced rate of genetic hypermutation in a cell producing antigen-binding polypeptides such as antibodies. Such cells include, but are not limited to, hybridomas. Expression of enhanced amounts of antigen-binding polypeptides may be through enhanced transcription or translation of the polynucleotides encoding the antigen binding polypeptides, or through the enhanced secretion of the antigen-binding polypeptides, for example.

Methods are also provided for creating genetically altered antibodies in vivo by blocking the MMR activity of the cell host, or by transfecting genes encoding for immunoglobulin in a MMR defective cell host.

Antibodies with increased binding properties to an antigen due to genetic changes within the variable domain are provided in methods of the invention that block endogenous MMR of the cell host. Antibodies with increased binding properties to an antigen due to genetic changes within the CDR regions within the light and/or heavy chains are also provided in methods of the invention that block endogenous MMR of the cell host.

The invention provides methods of creating genetically altered antibodies in MMR defective Ab producer cell lines with enhanced pharmacokinetic properties in host organisms including but not limited to rodents, primates, and man.

These and other aspects of the invention are provided by one or more of the embodiments described below. In one embodiment of the invention, a method for making an antibody-producing cell line hypermutable is provided. A polynucleotide encoding a dominant negative allele of a MMR gene is introduced into an antibody-producing cell. The cell becomes hypermutable as a result of the introduction of the gene.

In another embodiment of the invention, a method is provided for introducing a mutation into an endogenous gene encoding for an immunoglobulin polypeptide or a single chain antibody. A polynucleotide encoding a dominant negative allele of a MMR gene is introduced into a cell. The cell becomes hypermutable as a result of the introduction and expression of the MMR gene allele. The cell further comprises an immunoglobulin gene of interest. The cell is grown and tested to determine whether the gene encoding for an immunoglobulin or a single chain antibody of interest harbors a mutation. In another aspect of the invention, the gene encoding the mutated immunoglobulin polypeptide or single chain antibody may be isolated and expressed in a genetically stable cell. In a preferred embodiment, the mutated antibody is screened for at least one desirable property such as, but not limited to, enhanced binding characteristics.

In another embodiment of the invention, a gene or set of genes encoding for Ig light and heavy chains or a combination therein are introduced into a mammalian cell host that is MMR defective. The cell is grown, and clones are analyzed for antibodies with enhanced binding characteristics.

In another embodiment of the invention, a method will be provided for producing new phenotypes of a cell. A polynucleotide encoding a dominant negative allele of a MMR gene is introduced into a cell. The cell becomes hypermutable as a result of the introduction of the gene. The cell is grown. The cell is tested for the expression of new phenotypes where the phenotype is enhanced secretion of a polypeptide.

The invention also provides antibodies having increased affinity for antigen comprising immunoglobulin molecules wherein a substitution has been made for at least one amino acid in the variable domain of the heavy and/or light chain. In some embodiments, the substitution is in a position wherein the parental amino acid in that position is an amino acid with a non-polar side chain. In some embodiments the parental amino acid is substituted with a different amino acid that has a non-polar side chain. In other embodiments, the parental amino acid is replaced with a proline or hydroxyproline. In some embodiments, the substitution(s) are made in the framework regions of the heavy and/or light chain variable domains. In some embodiments, the substitution(s) are made within the first framework region of the heavy chain. In some embodiments, the substitution(s) are made within the second framework region of the light chain. In some embodiments, the substitutions are made within the first framework region of the heavy chain and the second framework region of the light chain. In some embodiments, a substitution is made at position 6 of the first framework region of the heavy chain as shown in SEQ ID NO:18. In some embodiments a substitution is made at position 22 of the second framework region of the light chain as shown in SEQ ID NO:21. For the specific position mutations, in some embodiments the amino acid substitution is a proline or hydroxyproline.

The invention also provides methods for increasing the affinity of an antibody for an antigen comprising substituting an amino acid within the variable domain of the heavy or light chain of the subject antibody with another amino acid having a non-polar side chain. In some embodiments, a proline is substituted for the original amino acid at the position. In some embodiments, proline is used to substitute for another amino acid having a non-polar side chain. In some embodiments alanine and/or leucine is replaced by proline. In certain embodiments, the amino acid in position 6 of the first framework region of the heavy chain of the antibody as shown in SEQ ID NO:18 is replaced with a proline. In other embodiments, the amino acid in position 22 of the second framework region of the light chain variable domain as shown in SEQ ID NO:21 is replaced with proline. The invention also provides antibodies produced by these methods.

The antibodies produced in the invention may be made using the process of the invention wherein a dominant negative allele of a mismatch repair gene is introduced into the antibody producing cell and the cell becomes hypermutable as described more fully herein. Alternatively, one may disrupt mismatch repair using chemical inhibitors of mismatch repair, such as using anthracene and/or its derivatives as described in PCT Publication No. WO 02/054856, published Jul. 18, 2002, which is specifically incorporated herein in its entirety. The cells treated with the chemicals that disrupt mismatch repair or which express a dominant-negative mismatch repair gene become hypermutable. The antibodies produced by the hypermutable cells are screened for increased affinity, and those antibodies comprising the amino acid substitutions described above display increased affinity for antigen. The cells producing the antibodies which have the increased affinity and the molecular characteristics described herein may be rendered genetically stable again by withdrawing the chemical inhibitor, or by rendering the cells genetically stable through the inactivation of the expression of the dominant negative allele. For example, a dominant negative allele that is under the control of an inducible promoter may be inactivated by withdrawing the inducer. Alternatively, the dominant negative allele may be knocked out, or a CRE-LOX expression system may be used whereby the dominant negative allele is spliced from the genome once the cells containing a genetically diverse immunoglobulin have been established.

In other embodiments, one of skill in the art may use any known method of introducing mutations into proteins and selecting for antibodies having higher affinity with the amino acid substitutions described above. Methods of introducing mutations may be random, such as chemical mutagenesis, or may be specific, such as site-directed mutagenesis. Methods for random and specific mutagenesis are well-known in the art and include, but are not limited to, for example, chemical mutagenesis (e.g. using such chemicals as methane sulfonate, dimethyl sulfonate, O6-methyl benzadine, methylnitrosourea (MNU), and ethylnitrosourea (ENU)); oligonucleotide-mediated site-directed mutagenesis; alanine scanning; and PCR mutagenesis (see, for example, Kunkel et al. (1991) *Methods Enzymol.* 204:125-139, site-directed mutagenesis; Crameri et al. (1995) *BioTechniques* 18(2):194-196, cassette mutagenesis; and Haught et al. (1994) *BioTechniques* 16(1):47-48, restriction selection mutagenesis).

These and other embodiments of the invention provide the art with methods that can generate enhanced mutability in cells and animals as well as providing cells and animals harboring potentially useful mutations for the large-scale production of high affinity antibodies with beneficial pharmacokinetic profiles.

BRIEF DESCRIPTION OF THE DRAWINGS

FIG. 4 shows generation of a genetically altered antibody with an increased binding activity. Shown are ELISA values from 96-well plates, screened for antibodies specific to hIgE. Two clones with a high binding value were found in HB134 cultures.

FIG. 5A illustrates sequence alteration within the variable chain of an antibody (a mutation within the light chain variable region in MMR-defective HB134 antibody producer cells). Arrows indicate the nucleotide at which a mutation occurred in a subset of cells from a clone derived from HB134 cells. The HB134 sequence (SEQ ID NO:25), the consensus sequence (SEQ ID NO:26), and the parental H36 sequence (SEQ ID NO:30) are shown. The change results in a Thr to Ser change within the light chain variable region. The coding sequence is in the antisense direction.

Figure 1:
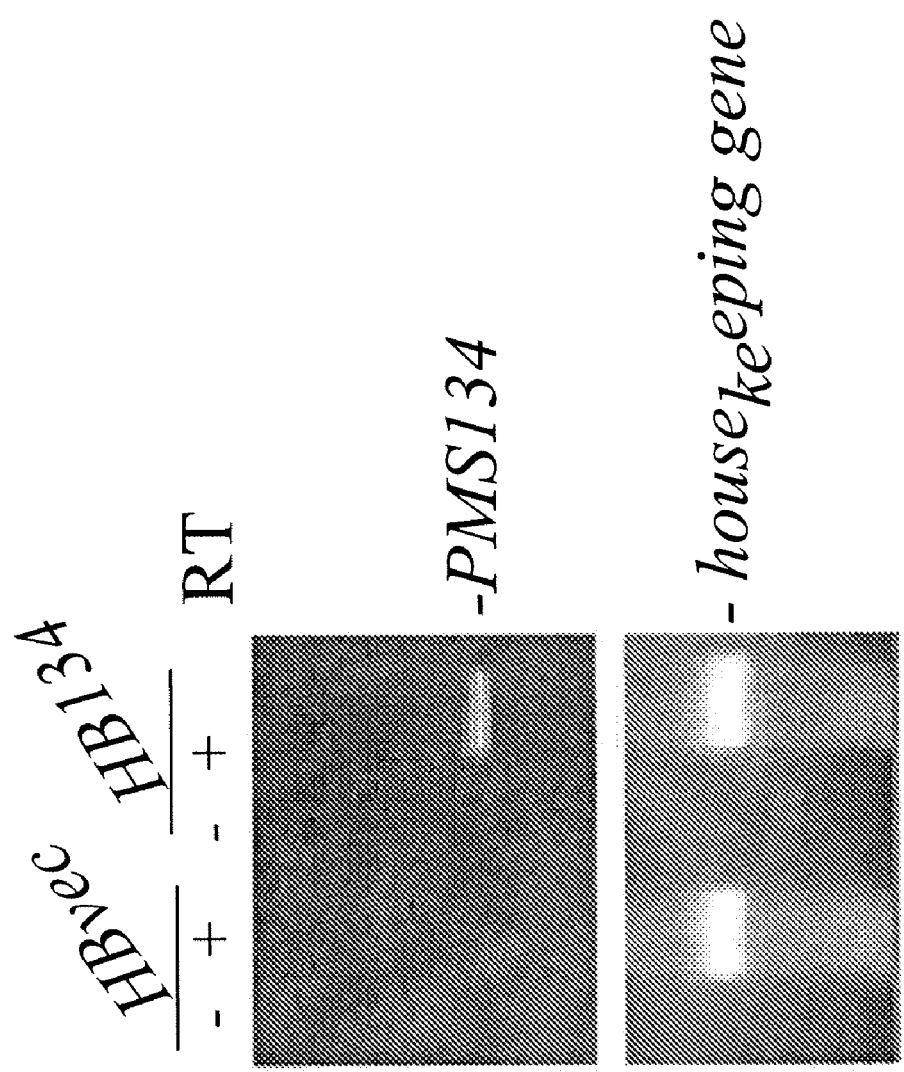
FIG. 1 shows stable expression of PMS2 and PMS 134 MMR genes by hybridoma cells. Shown is steady state mRNA expression of MMR genes transfected into a murine hybridoma cell line. Stable expression was found after 3 months of continuous growth. The (−) lanes represent negative controls where no reverse transcriptase was added, and the (+) lanes represent samples reverse transcribed and PCR amplified for the MMR genes and an internal housekeeping gene as a control.

Methods have been discovered for developing hypermutable antibody-producing cells by taking advantage of the conserved mismatch repair (MMR) process of host cells. Dominant negative alleles of such genes, when introduced into cells or transgenic animals, increase the rate of spontaneous mutations by reducing the effectiveness of DNA repair and thereby render the cells or animals hypermutable. Hypermutable cells or animals can then be utilized to develop new mutations in a gene of interest. Blocking MMR in antibody-producing cells such as but not limited to: hybridomas; mammalian cells transfected with genes encoding for Ig light and heavy chains; mammalian cells transfected with genes encoding for single chain antibodies; eukaryotic cells transfected with Ig genes, can enhance the rate of mutation within these cells leading to clones that have enhanced antibody production and/or cells containing genetically altered antibodies with enhanced biochemical properties such as increased antigen binding. The process of MMR, also called mismatch proofreading, is carried out by protein complexes in cells ranging from bacteria to mammalian cells. A MMR gene is a gene that encodes for one of the proteins of such a mismatch repair complex. Although not wanting to be bound by any particular theory of mechanism of action, a MMR complex is believed to detect distortions of the DNA helix resulting from non-complementary pairing of nucleotide bases. The non-complementary base on the newer DNA strand is excised, and the excised base is replaced with the appropriate base, which is complementary to the older DNA strand. In this way, cells eliminate many mutations that occur as a result of mistakes in DNA replication.

Dominant negative alleles cause a MMR defective phenotype even in the presence of a wild-type allele in the same cell. An example of a dominant negative allele of a MMR gene is the human gene hPMS2-134, which carries a truncating mutation at codon 134 (SEQ ID NO:15). The mutation causes the product of this gene to abnormally terminate at the position of the 134th amino acid, resulting in a shortened polypeptide containing the N-terminal 133 amino acids. Such a mutation causes an increase in the rate of mutations, which accumulate in cells after DNA replication. Expression of a dominant negative allele of a mismatch repair gene results in impairment of mismatch repair activity, even in the presence of the wild-type allele. Any allele which produces such effect can be used in this invention. Dominant negative alleles of a MMR gene can be obtained from the cells of humans, animals, yeast, bacteria, or other organisms. Such alleles can be identified by screening cells for defective MMR activity. Cells from animals or humans with cancer can be screened for defective mismatch repair. Cells from colon cancer patients may be particularly useful. Genomic DNA, cDNA, or mRNA from any cell encoding a MMR protein can be analyzed for variations from the wild type sequence. Dominant negative alleles of a MMR gene can also be created artificially, for example, by producing variants of the hPMS2-134 allele or other MMR genes. Various techniques of site-directed mutagenesis can be used. The suitability of such alleles, whether natural or artificial, for use in generating hypermutable cells or animals can be evaluated by testing the mismatch repair activity caused by the allele in the presence of one or more wild-type alleles, to determine if it is a dominant negative allele.

A cell or an animal into which a dominant negative allele of a mismatch repair gene has been introduced will become hypermutable. This means that the spontaneous mutation rate of such cells or animals is elevated compared to cells or animals without such alleles. The degree of elevation of the spontaneous mutation rate can be at least 2-fold, 5-fold, 10-fold, 20-fold, 50-fold, 100-fold, 200-fold, 500-fold, or 1000-fold that of the normal cell or animal. The use of chemical mutagens such as but limited to methane sulfonate, dimethyl sulfonate, O6-methyl benzadine, MNU, ENU, etc. can be used in MMR defective cells to increase the rates an additional 10- to 100-fold that of the MMR deficiency itself.

According to one aspect of the invention, a polynucleotide encoding for a dominant negative form of a MMR protein is introduced into a cell. The gene can be any dominant negative allele encoding a protein, which is part of a MMR complex, for example, PMS2, PMS1, MLH1, or MSH2. The dominant negative allele can be naturally occurring or made in the laboratory. The polynucleotide can be in the form of genomic DNA, cDNA, RNA, or a chemically synthesized polynucleotide.

The polynucleotide can be cloned into an expression vector containing a constitutively active promoter segment (such as but not limited to CMV, SV40, Elongation Factor or LTR sequences) or to inducible promoter sequences such as the steroid inducible pIND vector (Invitrogen), where the expression of the dominant negative MMR gene can be regulated. The polynucleotide can be introduced into the cell by transfection.

According to another aspect of the invention, an immunoglobulin (Ig) gene, a set of Ig genes or a chimeric gene containing whole or parts of an Ig gene can be transfected into MMR deficient cell hosts, the cell is grown and screened for clones containing genetically altered Ig genes with new biochemical features. MMR defective cells may be of human, primates, mammals, rodent, plant, yeast or of the prokaryotic kingdom. The mutated gene encoding the Ig with new biochemical features may be isolated from the respective clones and introduced into genetically stable cells (i.e., cells with normal MMR) to provide clones that consistently produce Ig with the new biochemical features. The method of isolating the Ig gene encoding Ig with new biochemical features may be any method known in the art. Introduction of the isolated polynucleotide encoding the Ig with new biochemical features may also be performed using any method known in the art, including, but not limited to transfection of an expression vector containing the polynucleotide encoding the Ig with new biochemical features. As an alternative to transfecting an Ig gene, a set of Ig genes or a chimeric gene containing whole or parts of an Ig gene into an MMR deficient host cell, such Ig genes may be transfected simultaneously with a gene encoding a dominant negative mismatch repair gene into a genetically stable cell to render the cell hypermutable.

Transfection is any process whereby a polynucleotide is introduced into a cell. The process of transfection can be carried out in a living animal, e.g. using a vector for gene therapy, or it can be carried out in vitro, e.g., using a suspension of one or more isolated cells in culture. The cell can be any type of eukaryotic cell, including, for example, cells isolated from humans or other primates, mammals or other vertebrates, invertebrates, and single celled organisms such as protozoa, yeast, or bacteria.

In general, transfection will be carried out using a suspension of cells, or a single cell, but other methods can also be applied as long as a sufficient fraction of the treated cells or tissue incorporates the polynucleotide so as to allow transfected cells to be grown and utilized. The protein product of the polynucleotide may be transiently or stably expressed in the cell. Techniques for transfection are well known. Available techniques for introducing polynucleotides include but are not limited to electroporation, transduction, cell fusion, the use of calcium chloride, and packaging of the polynucleotide together with lipid for fusion with the cells of interest. Once a cell has been transfected with the MMR gene, the cell can be grown and reproduced in culture. If the transfection is stable, such that the gene is expressed at a consistent level for many cell generations, then a cell line results.

An isolated cell is a cell obtained from a tissue of humans or animals by mechanically separating out individual cells and transferring them to a suitable cell culture medium, either with or without pretreatment of the tissue with enzymes, e.g., collagenase or trypsin. Such isolated cells are typically cultured in the absence of other types of cells. Cells selected for the introduction of a dominant negative allele of a mismatch repair gene may be derived from a eukaryotic organism in the form of a primary cell culture or an immortalized cell line, or may be derived from suspensions of single-celled organisms.

A polynucleotide encoding for a dominant negative form of a MMR protein can be introduced into the genome of an animal by producing a transgenic animal. The animal can be any species for which suitable techniques are available to produce transgenic animals. For example, transgenic animals can be prepared from domestic livestock, e.g., bovine, swine, sheep, goats, horses, etc.; from animals used for the production of recombinant proteins, e.g. bovine, swine, or goats that express a recombinant polypeptide in their milk; or experimental animals for research or product testing, e.g., mice, rats, guinea pigs, hamsters, rabbits, etc. Cell lines that are determined to be MMR defective can then be used as a source for producing genetically altered immunoglobulin genes in vitro by introducing whole, intact immunoglobulin genes and/or chimeric genes encoding for single chain antibodies into MMR defective cells from any tissue of the MMR defective animal.

Once a transfected cell line or a colony of transgenic animals has been produced, it can be used to generate new mutations in one or more gene(s) of interest. A gene of interest can be any gene naturally possessed by the cell line or transgenic animal or introduced into the cell line or transgenic animal. An advantage of using such cells or animals to induce mutations is that the cell or animal need not be exposed to mutagenic chemicals or radiation, which may have secondary harmful effects, both on the object of the exposure and on the workers. However, chemical mutagens may be used in combination with MMR deficiency, which renders such mutagens less toxic due to an undetermined mechanism. Hypermutable animals can then be bred and selected for those producing genetically variable B-cells that may be isolated and cloned to identify new cell lines that are useful for producing genetically variable cells. Once a new trait is identified, the dominant negative MMR gene allele can be removed by directly knocking out the allele by technologies used by those skilled in the art or by breeding to mates lacking the dominant negative allele to select for offspring with a desired trait and a stable genome. Another alternative is to use a CRE-LOX expression system, whereby the dominant negative allele is spliced from the animal genome once an animal containing a genetically diverse immunoglobulin profile has been established. Yet another alternative is the use of inducible vectors such as the steroid induced pIND (Invitrogen) or pMAM (Clonetech) vectors which express exogenous genes in the presence of corticosteroids.

Mutations can be detected by analyzing for alterations in the genotype of the cells or animals, for example by examining the sequence of genomic DNA, cDNA, messenger RNA, or amino acids associated with the gene of interest. Mutations can also be detected by screening for the production of antibody titers. A mutant polypeptide can be detected by identifying alterations in electrophoretic mobility, spectroscopic properties, or other physical or structural characteristics of a protein encoded by a mutant gene. One can also screen for altered function of the protein in situ, in isolated form, or in model systems. One can screen for alteration of any property of the cell or animal associated with the function of the gene of interest, such as but not limited to Ig secretion.

Examples of mismatch repair proteins and nucleic acid sequences include the following:

```
PMS2 (mouse) (SEQ ID NO: 5)
MEQTEGVSTE CAKAIKPIDG KSVHQICSGQ VILSLSTAVK    60
ELIENSVDAG ATTIDLRLKD

YGVDLIEVSD NGCGVEEENF EGLALKHHTS KIQEFADLTQ   120
VETFGFRGEA LSSLCALSDV

TISTCHGSAS VGTRLVFDHN GKITQKTPYP RPKGTTVSVQ   180
HLFYTLPVRY KEFQRNIKKE

YSKMVQVLQA YCIISAGVRV SCTNQLGQGK RHAVVCTSGT   240
SGMKENIGSV FGQKQLQSLI

PFVQLPPSDA VCEEYGLSTS GRHKTFSTFR ASFHSARTAP   300
GGVQQTGSFS SSTRGPVTQQ

RSLSLSMRFY HMYNRHQYPF VVLNVSVDSE CVDINVTPDK   360
RQILLQEEKL LLAVLKTSLI

GMFDSDANKL NVNQQPLLDV EGNLVKLHTA ELEKPVPGKQ   420
DNSPSLKSTA DEKRVASISR

LREAFSLHPT KETKSRGPET AELTRSFPSE KRGVLSSYPS   480
DVISYRGLRG SQDKLVSPTD

SPGDCMDREK TEKDSGLSST SAGSEEEFST PEVASSFSSD   540
YNVSSLEDRP SQETINCGDL

DCRPPGTGQS LKPEDHGYQC KALPLARLSP TNAKRFKTEE   600
RPSNVNISQR LPGPQSTSAA

EVDVAIKMNK RIVLLEFSLS SLAKRMKQLQ HLKAQNKHEL   660
SYRKFRAKIC PGENQAAEDE

LRKEISKSMF AEMEILGQFN LGFIVTKLKE DLFLVDQHAA   720
DEKYNFEMLQ QHTVLQAQRL

ITPQTLNLTA VNEAVLIENL EIFRKNGFDF VIDEDAPVTE   780
RAKLISLPTS KNWTFGPQDI
```

```
DELIFMLSDS PGVMCRPSRV RQMFASRACR KSVMIGTALN   840
ASEMKKLITH MGEMDHPWNC

PHGRPTMRHV ANLDVISQN                          859

PMS2 (mouse cDNA) (SEQ ID NO: 6)
gaattccggt gaaggtcctg aagaatttcc agattcctga    60
gtatcattgg aggagacaga taacctgtcg tcaggtaacg atggtgtata tgcaacagaa   120
atgggtgttc ctggagacgc gtcttttccc gagagcggca ccgcaactct cccgcggtga   180
ctgtgactgg aggagtcctg catccatgga gcaaaccgaa ggcgtgagta cagaatgtgc   240
taaggccatc aagcctattg atgggaagtc agtccatcaa atttgttctg ggcaggtgat   300
actcagttta agcaccgctg tgaaggagtt gatagaaaat agtgtagatg ctggtgctac   360
tactattgat ctaaggctta aagactatgg ggtggacctc attgaagttt cagacaatgg   420
atgtggggta gaagaagaaa actttgaagg tctagctctg aaacatcaca catctaagat   480
tcaagagttt gccgacctca cgcaggttga aactttcggc tttcgggggg aagctctgag   540
ctctctgtgt gcactaagtg atgtcactat atctacctgc cacgggtctg caagcgttgg   600
gactcgactg gtgtttgacc ataatgggaa aatcacccag aaaactccct accccgacc    660
taaaggaacc acagtcagtg tgcagcactt attttataca ctaccgtgc gttacaaaga    720
gtttcagagg aacattaaaa aggagtattc caaatggtg caggtcttac aggcgtactg    780
tatcatctca gcaggcgtcc gtgtaagctg cactaatcag ctcggacagg ggaagcggca   840
cgctgtggtg tgcacaagcg gcacgtctgg catgaaggaa aatatcgggt ctgtgtttgg   900
ccagaagcag ttgcaaagcc tcattccttt tgttcagctg ccccctagtg acgctgtgtg   960
tgaagagtac ggcctgagca cttcaggacg ccacaaaacc ttttctacgt ttcgggcttc  1020
atttcacagt gcacgcacgg cgccgggagg agtgcaacag acaggcagtt tttcttcatc  1080
aatcagaggc cctgtgaccc agcaaaggtc tctaagcttg tcaatgaggt tttatcacat  1140
gtataaccgg catcagtacc catttgtcgt ccttaacgtt tccgttgact cagaatgtgt  1200
ggatattaat gtaactccag ataaaaggca aattctacta caagaagaga agctattgct  1260
ggccgtttta aagacctcct tgataggaat gtttgacagt gatgcaaaca agcttaatgt  1320
caaccagcag ccactgctag atgttgaagg taacttagta aagctgcata ctgcagaact  1380
agaaaagcct gtgccaggaa agcaagataa ctctccttca ctgaagagca cagcagacga  1440
gaaaagggta gcatccatct ccaggctgag agaggccttt tctcttcatc ctactaaaga  1500
gatcaagtct aggggtccag
```

-continued

```
agactgctga actgacacgg agttttccaa gtgagaaaag      1560
gggcgtgtta tcctcttatc cttcagacgt catctcttac agaggcctcc gtggctcgca      1620
ggacaaattg gtgagtccca cggacagccc tggtgactgt atggacagag agaaaataga      1680
aaaagactca gggctcagca gcacctcagc tggctctgag gaagagttca gcaccccaga      1740
agtggccagt agctttagca gtgactataa cgtgagctcc ctagaagaca gaccttctca      1800
ggaaaccata aactgtggtg acctggactg ccgtcctcca ggtacaggac agtccttgaa      1860
gccagaagac catggatatc aatgcaaagc tctacctcta gctcgtctgt cacccacaaa      1920
tgccaagcgc ttcaagacag aggaaagacc ctcaaatgtc aacatttctc aaagattgcc      1980
tggtcctcag agcacctcag cagctgaggt cgatgtagcc ataaaaatga ataagagaat      2040
cgtgctcctc gagttctctc tgagttctct agctaagcga atgaagcagt tacagcacct      2100
aaaggcgcag aacaaacatg aactgagtta cagaaaattt agggccaaga tttgccctgg      2160
agaaaaccaa gcagcagaag atgaactcag aaaagagatt agtaaatcga tgtttgcaga      2220
gatgaagatc ttgggtcagt ttaacctggg atttatagta accaaactga agaggacct      2280
cttcctggtg gaccagcatg ctgcggatga gaagtacaac tttgagatgc tgcagcagca      2340
cacggtgctc caggcgcaga ggctcatcac cccccagact ctgaacttaa ctgctgtcaa      2400
tgaagctgta ctgatagaaa atctggaaat attcagaaag aatggctttg actttgtcat      2460
tgatgaggat gctccagtca ctgaaaggc taaattgatt tccttaccaa ctagtaaaaa      2520
ctggaccttt ggaccccaag atatagatga actgatcttt atgttaagtg acagccctgg      2580
ggtcatgtgc cggccctcac gagtcagaca gatgtttgct tccagagcct gtcggaagtc      2640
agtgatgatt ggaacggcgc tcaatgcgag cgagatgaag aagctcatca cccacatggg      2700
tgagatggac caccctgga actgccccca cggcaggcca accatgaggc acgttgccaa      2760
tctgatgtc atctctcaga actgacacgg cccttgtagc atagagttta ttacagattg      2820
ttcggtttgc aaagagaagg ttttaagtaa tctgattatc gttgtacaaa aattagcatg      2880
ctgctttaat gtactggatc catttaaaag cagtgttaag gcaggcatga tggagtgttc      2940
ctctagctca gctactggg tgatccggtg ggagctcatg tgagcccagg acttgagac      3000
cactccgagc acattcatg agactcaatt caaggacaaa aaaaaaaga tattttgaa      3056
gcctttaaa aaaaaa
```

PMS2 (human) (SEQ ID NO: 7)

```
MERAESSSTE PAKAIKPIDR KSVHQICSGQ VVLSLSTAVK
ELVENSLDAG
ATNIDLKLKD                                        60

YGVDLIEVSD NGCGVEEENF EGLTLKHHTS KIQEFADLTQ
VETFGFRGEA LSSLCALSDV                            120

TISTCHASAK VGTRLMFDHN GKIIQKTPYP RPRGTTVSVQ
QLFSTLPVRH KEFQRNIKKE                            180

YAKMVQVLHA YCIISAGIRV SCTNQLGQGK RQPVVCTGGS
PSIKENIGSV FGQKQLQSLI                            240

PFVQLPPSDS VCEEYGLSCS DALHNLFYIS GFISQCTHGV
GRSSTDRQFF FINRRPCDPA                            300

KVCRLVNEVY HMYNRHQYPF VVLNISVDSE CVDINVTPDK
RQILLQEEKL LLAVLKTSLI                            360

GMFDSDVNKL NVSQQPLLDV EGNLIKMHAA DLEKPNVEKQ
DQSPSLRTGE EKKDVSISRL                            420

REAFSLRHTT ENKPHSPKTP EPRRSPLGQK RGMLSSSTSG
AISDKGVLRP QKEAVSSSHG                            480

PSDPTDRAEV EKDSGHGSTS VDSEGFSIPD TGSHCSSEYA
ASSPGDRGSQ EHVDSQEKAP                            540

ETDDSFSDVD CHSNQEDTGC KFRVLPQPTN LATPNTKRFK
KEEILSSSDI CQKLVNTQDM                            600

SASQVDVAVK INKKVVPLDF SMSSLAKRIK QLHHEAQQSE
GEQNYRKFRA KICPGENQAA                            660

EDELRKEISK TMFAEMEIIG QFNLGFIITK LNEDIFIVDQ
HATDEKYNFE MLQQHTVLQG                            720

QRLIAPQTLN LTAVNEAVLI ENLEIFRKNG FDFVIDENAP
VTERAKLISL PTSKNWTFGP                            780

QDVDELIFML SDSPGVMCRP SRVKQMFASR ACRKSVMIGT
ALNTSEMKKL ITHMGEMDHP                            840

WNCPHGRPTM RHIANLGVIS QN                         862
```

PMS2 (human cDNA) (SEQ ID NO: 8)

```
cgaggcggat cgggtgttgc atccatggag cgagctgaga      60
gctcgagtac agaacctgct aaggccatca aacctattga tcggaagtca gtccatcaga     120
tttgctctgg gcaggtggta ctgagtctaa gcactgcggt aaaggagtta gtagaaaaca     180
gtctggatgc tggtgccact aatattgatc taaagcttaa ggactatgga gtggatctta     240
ttgaagtttc agacaatgga tgtggggtag aagaagaaaa cttcgaaggc ttaactctga     300
aacatcacac atctaagatt caagagtttg ccgacctaac tcaggttgaa acttttggct     360
ttcgggggga agctctgagc tcactttgtg cactgagcga tgtcaccatt tctacctgcc     420
acgcatcggc gaaggttgga actcgactga tgtttgatca caatgggaaa attatccaga     480
aaacccccta cccccgcccc agagggacca cagtcagcgt gcagcagtta ttttccacac     540
tacctgtgcg ccataaggaa tttcaaagga atattaagaa ggagtatgcc aaaatggtcc     600
aggtcttaca tgcatactgt atcatttcag caggcatccg tgtaagttgc accaatcagc     660
ttggacaagg aaaacgacag cctgtggtat gcacaggtgg aagccccagc ataaaggaaa     720
```

-continued

```
atatcggctc tgtgtttggg cagaagcagt tgcaaagcct cattccttt gttcagctgc       780
cccctagtga ctccgtgtgt gaagagtacg gttgagctg ttcggatgct ctgcataatc       840
ttttttacat ctcaggtttc atttcacaat gcacgcatgg agttggaagg agttcaacag       900
acagacagtt tttctttatc aaccggcggc cttgtgaccc agcaaaggtc tgcagactcg       960
tgaatgaggt ctaccacatg tataatcgac accagtatcc atttgttgtt cttaacattt      1020
ctgttgattc agaatgcgtt gatatcaatg ttactccaga taaaaggcaa attttgctac      1080
aagaggaaaa gcttttgttg gcagttttaa agacctcttt gataggaatg tttgatagtg      1140
atgtcaacaa gctaaatgtc agtcagcagc cactgctgga tgttgaaggt aacttaataa      1200
aaatgcatgc agcggatttg gaaaagccca tggtagaaaa gcaggatcaa tccccttcat      1260
taaggactgg agaagaaaaa aaagacgtgt ccatttccag actgcgagag gccttttctc      1320
ttcgtcacac aacagagaac aagcctcaca gcccaaagac tccagaacca agaaggagcc      1380
ctctaggaca gaaaagggt atgctgtctt ctagcacttc aggtgccatc tctgacaaag      1440
gcgtcctgag acctcagaaa gaggcagtga gttccagtca cggacccagt gaccctacgg      1500
acagagcgga ggtggagaag gactcggggc acggcagcac ttccgtggat tctgaggggt      1560
tcagcatccc agacacgggc agtcactgca gcagcgagta tgcggccagc tccccagggg      1620
acaggggctc gcaggaacat gtggactctc aggagaaagc gcctgaaact gacgactctt      1680
tttcagatgt ggactgccat tcaaaccagg aagataccgg atgtaaattt cgagttttgc      1740
ctcagccaac taatctcgca accccaaaca caaagcgttt taaaaaagaa gaaattcttc      1800
ccagttctga catttgtcaa aagttagtaa atactcagga catgtcagcc tctcaggttg      1860
atgtagctgt gaaaattaat aagaaagttg tgcccctgga cttttctatg agttctttag      1920
ctaaacgaat aaagcagtta catcatgaag cacagcaaag tgaaggggaa cagaattaca      1980
ggaagtttag ggcaaagatt tgtcctggag aaaatcaagc agccgaagat gaactaagaa      2040
aagagataag taaaacgatg tttgcagaaa tggaaatcat tggtcagttt aacctgggat      2100
ttataataac caaactgaat gaggatatct tcatagtgga ccagcatgcc acggacgaga      2160
agtataactt cgagatgctg cagcagcaca ccgtgctcca ggggcagagg ctcatagcac      2220
ctcagactct caacttaact gctgttaatg aagctgttct gatagaaaat ctggaaatat      2280
ttagaaagaa tggctttgat
```

-continued

```
tttgttatcg atgaaaatgc tccagtcact gaaagggcta      2340
aactgatttc cttgccaact agtaaaaact ggaccttcgg acccaggac gtcgatgaac       2400
tgatcttcat gctgagcgac agccctgggg tcatgtgccg gccttcccga gtcaagcaga      2460
tgtttgcctc cagagcctgc cggaagtcgg tgatgattgg gactgctctt aacacaagcg      2520
agatgaagaa actgatcacc cacatggggg agatggacca cccctggaac tgtccccatg      2580
gaaggccaac catgagacac atcgccaacc tgggtgtcat ttctcagaac tgaccgtagt      2640
cactgtatgg aataattggt tttatcgcag attttatgt tttgaaagac agagtcttca      2700
ctaacctttt ttgttttaaa atgaaacctg ctacttaaaa aaaatacaca tcacacccat      2760
ttaaaagtga tcttgagaac cttttcaaac c                                     2771

PMS1 (human) (SEQ ID NO: 9)
MKQLPAATVR LLSSSQIITS VVSVVKELIE NSLDAGATSV       60
DVKLENYGFD KIEVRDNEG

IKAVDAPVMA MKYYTSKINS HEDLENLTTY GFRGEALGSI      120
CCIAEVLITT RTAADNFSTQ

YVLDGSGHIL SQKPSHLGQG TTVTALRLFK NLPVRKQFYS      180
TAKKCKDEIK KIQDLLMSFG

ILKPDLRIVF VHNKAVIWQK SRVSDHKMAL MSVLGTAVMN      240
NNESFQYHSE ESQIYLSGFL

PKCDADHSFT SLSTPERSFI FINSRPVHQK DILKLIRHHY      300
NLKCLKESTR LYPVFFLKID

VPTADVDVNL TPDKSQVLLQ NKESVLIALE NLMTTCYGPL      360
PSTNSYENNK TDVSAADIVL

SKTAETDVLF NKVESSGKNY SNVDTSVIPF QNDMHNDESG      420
KNTDDCLNHQ ISIGDFGYGH

CSSEISNIDK NTKNAFQDIS MSNVSWENSQ TEYSKTCFIS      480
SVKHTQSENG NKDHIDESGE

NEEEAGLENS SEISADEWSR GNILKNSVGE NIEPVKILVP      540
EKSLPCKVSN NNYPIPEQMN

LNEDSCNKKS NVIDNKSGKV TAYDLLSNRV IKKPMSASAL      600
FVQDHRPQFL IENPKTSLED

ATLQIEELWK TLSEEEKLKY EEKATKDLER YNSQMKRAIE      660
QESQMSLKDG RKKIKPTSAW

NLAQKHKLKT SLSNQPKLDE LLQSQIEKRR SQNIKNVQIP      720
FSMKNLKINF KKQNKVDLEE

KDEPCLIHNL RFPDAWLMTS KTEVMLLNPY RVEEALLFKR      780
LLENHKLPAE PLEKPIMLTE

SLFNGSHYLD VLYKMTADDQ RYSGSTYLSD PRLTANGFKI      840
KLIPGVSITE NYLEIEGMAN

CLPFYGVADL KEILNAILNR NAKEVYECRP RKVISYLEGE      900
AVRLSRQLPM YLSKEDIQDI

IYRMKHQFGN EIKECVHGRP FFHHLTYLPE TT              932

PMS1 (human) (SEQ ID NO: 10)
ggcacgagtg gctgcttgcg gctagtggat ggtaattgcc        60
tgcctcgcgc tagcagcaag ctgtctctgtt aaaagcgaaa atgaaacaat tgcctgcggc      120
aacagttcga ctcctttcaa
```

-continued

```
gttctcagat catcacttcg gtggtcagtg ttgtaaaaga      180
gcttattgaa aactccttgg atgctggtgc cacaagcgta gatgttaaac tggagaacta      240
tggatttgat aaaattgagg tgcgagataa cggggagggt atcaaggctg ttgatgcacc      300
tgtaatggca atgaagtact acacctcaaa aataaatagt catgaagatc ttgaaaattt      360
gacaacttac ggttttcgtg gagaagcctt ggggtcaatt tgttgtatag ctgaggtttt      420
aattacaaca agaacggctg ctgataattt tagcacccag tatgttttag atggcagtgg      480
ccacatactt tctcagaaac cttcacatct tggtcaaggt acaactgtaa ctgctttaag      540
attatttaag aatctacctg taagaaagca gttttactca actgcaaaaa aatgtaaaga      600
tgaaataaaa aagatccaag atctcctcat gagctttggt atccttaaac ctgacttaag      660
gattgtcttt gtacataaca aggcagttat ttggcagaaa agcagagtat cagatcacaa      720
gatggctctc atgtcagttc tggggactgc tgttatgaac aatatggaat cctttcagta      780
ccactctgaa gaatctcaga tttatctcag tggatttctt ccaaagtgtg atgcagacca      840
ctctttcact agtctttcaa caccagaaag aagtttcatc ttcataaaca gtcgaccagt      900
acatcaaaaa gatatcttaa agttaatccg acatcattac aatctgaaat gcctaaagga      960
atctactcgt ttgtatcctg ttttctttct gaaaatcgat gttcctacag ctgatgttga     1020
tgtaaattta acaccagata aaagccaagt attattacaa aataaggaat ctgttttaat     1080
tgctcttgaa aatctgatga cgacttgtta tggaccatta cctagtacaa attcttatga     1140
aaataataaa acagatgttt ccgcagctga catcgttctt agtaaaacag cagaaacaga     1200
tgtgcttttt aataaagtgg aatcatctgg aaagaattat tcaaatgttg atacttcagt     1260
cattccattc caaaatgata tgcataatga tgaatctgga aaaaacactg atgattgttt     1320
aaaatcaccag ataagtattg gtgactttgg ttatggtcat tgtagtagtg aaatttctaa     1380
cattgataaa aacactaaga atgcatttca ggacatttca atgagtaatg tatcatggga     1440
gaactctcag acgaatatat gtaaaacttg ttttataagt tccgttaagc acacccagtc     1500
agaaaatggc aataaagacc atatagatga gagtgggaa atgaggaag aagcaggtct      1560
tgaaaactct tcggaaattt ctgcagatga gtggagcagg ggaaatatac ttaaaaattc     1620
agtgggagag aatattgaac ctgtgaaaat tttagtgcct gaaaaagtt taccatgtaa      1680
agtaagtaat aataattatc caatccctga acaaatgaat cttaatgaag attcatgtaa     1740
```

```
caaaaaatca aatgtaatag ataataaatc tggaaaagtt acagcttatg atttacttag     1800
caatcgagta atcaagaaac ccatgtcagc aagtgctctt tttgttcaag atcatcgtcc     1860
tcagtttctc atagaaaatc ctaagactag tttagaggat gcaacactac aaattgaaga     1920
actgtggaag acattgagtg aagaggaaaa actgaaatat gaagagaagg ctactaaaga     1980
cttggaacga tacaatagtc aaatgaagag agccattgaa caggagtcac aaatgtcact     2040
aaaagatggc agaaaaaaga taaaacccac cagcgcatgg aatttggccc agaagcacaa     2100
gttaaaaacc tcattatcta atcaaccaaa acttgatgaa ctccttcagt cccaaattga     2160
aaaaagaagg agtcaaaata ttaaaatggt acagatcccc ttttctatga aaaacttaaa     2220
aataaatttt aagaaacaaa acaaagttga cttagaagag aaggatgaac cttgcttgat     2280
ccacaatctc aggtttcctg atgcatggct aatgacatcc aaaacagagg taatgttatt     2340
aaatccatat agagtagaag aagccctgct atttaaaaga cttcttgaga atcataaact     2400
tcctgcagag ccactggaaa agccaattat gttaacagag gtctttttta tggatctca      2460
ttatttagac gttttatata aaatgacagc agatgaccaa agatacagtg gatcaactta     2520
cctgtctgat cctcgtctta cagcgaatgg tttcaagata aaattgatac caggagtttc     2580
aattactgaa aattacttgg aaatagaagg aatggctaat tgtctcccat tctatggagt     2640
agcagattta aaagaaattc ttaatgctat attaaacaga aatgcaaagg aagtttatga     2700
atgtagacct cgcaaagtga taagttattt agagggagaa gcagtgcgtc tatccagaca     2760
attacccatg tacttatcaa aagaggacat ccaagacatt atctacagaa tgaagcacca     2820
gtttggaaat gaaattaaag agtgtgttca tggtcgccca tttttttcatc atttaaccta     2880
tcttccagaa actacatgat taaatatgtt taagaagatt agttaccatt gaaattggtt     2940
ctgtcataaa acagcatgag tctggtttta aattatcttt gtattatgtg tcacatggtt     3000
attttttaaa tgaggattca ctgacttgtt tttatattga aaaaagttcc acgtattgta     3060
gaaaacgtaa ataaactaat aac                                              3063

MSH2 (human) (SEQ ID NO: 11)
MAVQPKETLQ LESAAEVGFV RFFQGMPEKP TTTVRLFDRG       60
DFYTAHGEDA LLAAREVFKT

QGVIKYMGPA GAKNLQSVVL SKMNFESFVK DLLLVRQYRV      120
EVYKNRAGNK ASKENDWYLA

YKASPGNLSQ FEDILFGNND MSASIGVVGV KMSAVDGQRQ      180
VGVGYVDSIQ RKLGLCEFPD
```

-continued

```
NDQFSNLEAL LIQIGPKECV LPGGETAGDM GKLRQIIQRG      240
GILITERKKA DFSTKDIYQD

LNRLLKGKKG EQMNSAVLPE MENQVAVSSL SAVIKFLELL      300
SDDSNFGQFE LTTFDFSQYM

KLDIAAVRAL NLFQGSVEDT TGSQSLAALL NKCKTPQGQR      360
LVNQWIKQPL MDKNRIEERL

NLVEAFVEDA ELRQTLQEDL LRRFPDLNRL AKKFQRQAAN      420
LQDCYRLYQG INQLPNVIQA

LEKHEGKHQK LLLAVFVTPL TDLRSDFSKF QEMIETTLDM      480
DQVENHEFLV KPSFDPNLSE

LREIMNDLEK KMQSTLISAA RDLGLDPGKQ IKLDSSAQFG      540
YYFRVTCKEE KVLRNNKNFS

TVDIQKNGVK FTNSKLTSLN EEYTKNKTEY EEAQDAIVKE      600
IVNISSGYVE PMQTLNDVLA

QLDAVVSFAH VSNGAPVPYV RPAILEKGQG RIILKASRHA      660
CVEVQDEIAF IPNDVYFEKD

KQMFHIITGP NMGGKSTYIR QTGVIVLMAQ IGCFVPCESA      720
EVSIVDCILA RVGAGDSQLK

GVSTFMAEML ETASILRSAT KDSLIIIDEL GRGTSTYDGF      780
GLAWAISEYI ATKIGAFCMF

ATHFHELTAL ANQIPTVNNL HVTALTTEET LTMLYQVKKG      840
VCDQSFGIHV AELANFPKHV

IECAKQKALE LEEFQYIGES QGYDIMEPAA KKCYLEREQG      900
EKIIQEFLSK VKQMPFTEMS

EENITIKLKQ LKAEVIAKNN SFVNEIISRI KVTT            934

MSH2 (human cDNA) (SEQ ID NO: 12)
ggcgggaaac agcttagtgg gtgtggggtc gcgcattttc       60
ttcaaccagg aggtgaggag gtttcgacat ggcggtgcag ccgaaggaga cgctgcagtt      120
ggagagcgcg gccgaggtcg gcttcgtgcg cttctttcag ggcatgccgg agaagccgac      180
caccacagtg cgccttttcg accggggcga cttctatacg gcgcacggcg aggacgcgct      240
gctggccgcc cgggaggtgt tcaagaccca gggggtgatc aagtacatgg ggccggcagg      300
agcaaagaat ctgcagagtg ttgtgcttag taaaatgaat tttgaatctt ttgtaaaaga      360
tcttcttctg gttcgtcagt atagagttga agtttataag aatagagctg gaaataaggc      420
atccaaggag aatgattggt atttggcata taaggcttct cctggcaatc tctctcagtt      480
tgaagacatt ctctttggta acaatgatat gtcagcttcc attggtgttg tgggtgttaa      540
aatgtccgca gttgatggcc agagacaggt tggagttggg tatgtggatt ccatacagag      600
gaaactagga ctgtgtgaat tccctgataa tgatcagttc tccaatcttg aggctctcct      660
catccagatt ggaccaaagg aatgtgtttt acccgaggag agactgctg gagacatggg      720
gaaactgaga cagataattc aaagaggagg aattctgatc acagaaagaa aaaagctga      780
ctttttccaca aaagacattt atcaggacct caaccggttg ttgaaaggca aaaagggaga      840
gcagatgaat agtgctgtat
```

-continued

```
tgccagaaat ggagaatcag gttgcagttt catcactgtc      900
tgcggtaatc aagttttag aactcttatc agatgattcc aactttggac agtttgaact      960
gactactttt gacttcagcc agtatatgaa attggatatt gcagcagtca gagcccttaa     1020
ccttttttcag ggttctgttg aagataccac tggctctcag tctctggctg ccttgctgaa     1080
taagtgtaaa accccctcaag gacaaagact tgttaaccag tggattaagc agcctctcat     1140
ggataagaac agaatagagg agagattgaa tttagtggaa gcttttgtag aagatgcaga     1200
attgaggcag actttacaag aagatttact tcgtcgattc ccagatctta accgacttgc     1260
caagaagttt caaagacaag cagcaaactt acaagattgt taccgactct atcagggtat     1320
aaatcaacta cctaatgtta tacaggctct ggaaaaacat gaaggaaaac accagaaatt     1380
attgttggca gttttgtga ctcctcttac tgatcttcgt tctgacttct ccaagtttca     1440
ggaaatgata gaaacaactt tagatatgga tcaggtggaa aaccatgaat tccttgtaaa     1500
accttcattt gatcctaatc tcagtgaatt aagagaaata atgaatgact ggaaaagaa     1560
gatgcagtca acattaataa gtgcagccag agatcttggc ttggaccctg gcaaacagat     1620
taaactggat tccagtgcac agtttggata ttactttcgt gtaacctgta aggaagaaaa     1680
agtccttcgt aacaataaaa actttagtac tgtagatatc cagaagaatg tgttaaattt     1740
taccaacagc aaattgactt ctttaaatga agagtatacc aaaaataaaa cagaatatga     1800
agaagcccag gatgccattg ttaagagaaat tgtcaatatt tcttcaggct atgtagaacc     1860
aatgcagaca ctcaatgatg tgttagctca gctagatgct gttgtcagct ttgctcacgt     1920
gtcaaatgga gcacctgttc catatgtacg accagccatt ttggagaaag acaaggaag     1980
aattatatta aaagcatcca ggcatgcttg tgttgaagtt caagatgaaa ttgcatttat     2040
tcctaatgac gtatactttg aaaaagataa acagatgttc acatcatta ctggccccaa     2100
tatgggaggt aaatcaacat atattcgaca aactggggtg atagtactca tggcccaaat     2160
tgggtgtttt gtgccatgtg agtcagcaga agtgtccatt gtggactgca tcttagcccg     2220
agtagggct ggtgacagtc aattgaaagg agtctccacg ttcatggctg aaatgttgga     2280
aactgcttct atcctcaggt ctgcaaccaa agattcatta ataatcatag atgaattggg     2340
aagaggaact tctacctacg atgatttggg gttagcatgg gctatatcag aatacattgc     2400
aacaaagatt ggtgcttttt gcatgtttgc aacccatttt catgaactta ctgccttggc     2460
```

-continued

```
caatcagata ccaactgtta ataatctaca tgtcacagca ctcaccactg aagagacctt    2520
aactatgctt tatcaggtga agaaaggtgt ctgtgatcaa agttttggga ttcatgttgc    2580
agagcttgct aatttcccta agcatgtaat agagtgtgct aaacagaaag ccctggaact    2640
tgaggagttt cagtatattg gagaatcgca aggatatgat atcatggaac cagcagcaaa    2700
gaagtgctat ctggaaagag agcaaggtga aaaaattatt caggagttcc tgtccaaggt    2760
gaaacaaatg cccctttactg aaatgtcaga agaaacatc acaataaagt taaaacagct    2820
aaaagctgaa gtaatagcaa agaataatag ctttgtaaat gaaatcattt cacgaataaa    2880
agttactacg tgaaaaatcc cagtaatgga atgaaggtaa tattgataag ctattgtctg    2940
taatagtttt atattgtttt atattaaccc ttttccata gtgttaactg tcagtgccca     3000
tgggctatca acttaataag atatttagta atattttact ttgaggacat tttcaaagat    3060
ttttattttg aaaaatgaga gctgtaactg aggactgttt gcaattgaca taggcaataa    3120
taagtgatgt gctgaatttt ataaataaaa tcatgtagtt tgtgg                    3145

MLH1 (human) (SEQ ID NO: 13)
MSFVAGVIRR LDETVVNRIA AGEVIQRPAN AIKEMIENCL     60
DAKSTSIQVI VKEGGLKLIQ

IQDNGTGIRK EDLDIVCERF TTSKLQSFED LASISTYGFR    120
GEALASISHV AHVTITTKTA

DGKCAYRASY SDGKLKAPPK PCAGNQGTQI TVEDLFYNIA    180
TRRKALKUPS EEYGKILEVV

GRYSVHNAGI SFSVKKQGET VADVRTLPNA STVDNIRSIF    240
GNAVSRELIE IGCEDKTLAF

KMNGYISNAN YSVKKCIFLL FINHRLVEST SLRKAIETVY    300
AAYLPKNTHP FLYLSLEISP

QNVDVNVHPT KHEVHFLHEE SILERVQQHI ESKLLGSNSS    360
RMYFTQTLLP GLAGPSGEMV

KSTTSLTSSS TSGSSDKVYA HQMVRTDSRE QKLDAFLQPL    420
SKPLSSQPQA IVTEDKTDIS

SGRARQQDEE MLELPAPAEV AAKNQSLEGD TTKGTSEMSE    480
KRGPTSSNPR KRHREDSDVE

NVEDDSRKEM TAACTPRRRI INLTSVLSLQ EEINEQGHEV    540
LREMLHNHSF VGCVNPQWAL

AQHQTKLYLL NTTKLSEELF YQILIYDFAN FGVLRLSEPA    600
PLFDLAMLAL DSPESGWTEE

DGPKEGLAEY IVEFLKKKAE MLADYFSLEI DEEGNLIGLP    660
LLIDNYVPPL EGLPIFILRL

ATEVNWDEEK ECFESLSKEC AMFYSIRKQY ISEESTLSGQ    720
QSEVPGSIPN SWKWTVEHIV

YKALRSHILP PKHFTEDGNI LQLATLPDLY KVFERC        756

MLH1 (human) (SEQ ID NO: 14)
cttggctctt ctggcgccaa aatgtcgttc gtggcagggg     60
ttattccggcg gctggacgag acagtggtga accgcatcgc ggcgggggaa gttatccagc    120
ggccagctaa tgctatcaaa gagatgattg agaactgttt agatgcaaaa tccacaagta    180
ttcaagtgat tgttaaagag ggaggcctga agttgattca gatccaagac aatggcaccg    240
ggatcaggaa agaagatctg gatattgtat gtgaaaggtt cactactagt aaactgcagt    300
cctttgagga tttagccagt atttctacct atggctttcg aggtgaggct ttggccagca    360
taagccatgt ggctcatgtt actattacaa cgaaaacagc tgatggaaag tgtgcataca    420
gagcaagtta ctcagatgga aaactgaaag cccctcctaa accatgtgct ggcaatcaag    480
ggacccagat cacggtggag gacctttttt acaacatagc cacgaggaga aaagctttaa    540
aaaatccaag tgaagaatat gggaaaattt tggaagttgt tggcaggtat tcagtacaca    600
atgcaggcat tagtttctca gttaaaaaac aaggagagac agtagctgat gttaggacac    660
tacccaatgc ctcaaccgtg gacaatattc gctccatctt tggaaatgct gttagtcgag    720
aactgataga aattggatgt gaggataaaa ccctagcctt caaaatgaat ggttacatat    780
ccaatgcaaa ctactcagtg aagaagtgca tcttcttact cttcatcaac catcgtctgg    840
tagaatcaac ttccttgaga aaagccatag aaacagtgta tgcagcctat ttgcccaaaa    900
acacacaccc attcctgtac ctcagtttag aaatcagtcc ccagaatgtg gatgttaatg    960
tgcaccccac aaagcatgaa gttcacttcc tgcacgagga gagcatcctg gagcgggtgc   1020
agcagcacat cgagagcaag ctcctgggct ccaattcctc caggatgtac ttcacccaga  1080
ctttgctacc aggacttgct ggccctctg gggagatggt aaaatccaca acaagtctga   1140
cctcgtcttc tacttctgga agtagtgata aggtctatgc ccaccagatg gttcgtacag   1200
attcccggga acagaagctt gatgcatttc tgcagcctct gagcaaaccc ctgtccagtc   1260
agccccaggc cattgtcaca gaggataaga cagatatttc tagtggcagg gctaggcagc   1320
aagatgagga gatgcttgaa ctcccagccc ctgctgaagt ggctgccaaa atcagagctc  1380
tggaggggga tacaacaaag gggacttcag aaatgtcaga aagagagga cctacttcca   1440
gcaaccccag aaagagacat cgggaagatt ctgatgtgga aatggtggaa gatgattccc   1500
gaaaggaaat gactgcagct tgtaccccc ggagaaggat cattaacctc actagtgttt    1560
tgagtctcca ggaagaaatt aatgagcagg gacatgaggt tctccgggag atgttgcata   1620
accactcctt cgtgggctgt gtgaatcctc agtgggcctt ggcacagcat caaaccaagt   1680
tataccttct caacaccacc
```

```
                                           -continued
aagcttagtg aagaactgtt ctaccagata ctcatttatg        1740
attttgccaa ttttggtgtt ctcaggttat cggagccagc accgctcttt gaccttgcca        1800
tgcttgcctt agatagtcca gagagtggct ggacagagga agatggtccc aaagaaggac        1860
ttgctgaata cattgttgag tttctgaaga agaaggctga gatgcttgca gactatttct        1920
ctttggaaat tgatgaggaa gggaacctga ttggattacc ccttctgatt gacaactatg        1980
tgcccccttt ggagggactg cctatcttca ttcttcgact agccactgag gtgaattggg        2040
acgaagaaaa ggaatgtttt gaaagcctca gtaaagaatg cgctatgttc tattccatcc        2100
ggaagcagta catatctgag gagtcgaccc tctcaggcca gcagagtgaa gtgcctggct        2160
ccattccaaa ctcctggaag tggactgtgg aacacattgt ctataaagcc ttgcgctcac        2220
acattctgcc tcctaaacat ttcacagaag atggaaatat cctgcagctt gctaacctgc        2280
ctgatctata caaagtcttt gagaggtgtt aaatatggtt atttatgcac tgtgggatgt        2340
gttcttcttt ctctgtattc cgatacaaag tgttgtatca aagtgtgata tacaaagtgt        2400
accaacataa gtgttggtag cacttaagac ttatacttgc cttctgatag tattccttta        2460
tacacagtgg attgattata aataaataga tgtgtcttaa cata                         2484 hPMS2-134 (human) (SEQ ID NO: 15)
MERAESSSTE PAKAIKPIDR KSVHQICSGQ VVLSLSTAVK          60
ELVENSLDAG ATNIDLKLKD

YGVDLIEVSD NGCGVEEENF EGLTLKHHTS KIQEFADLTQ         120
VETFGFRGEA LSSLCALSDV

TISTCHASAK VGT                                      133 hPMS2-134 (human cDNA) (SEQ ID NO: 16)
cgaggcggat cgggtgttgc atccatggag cgagctgaga          60
gctcgagtac agaacctgct aaggccatca aacctattga tcggaagtca gtccatcaga         120
tttgctctgg gcaggtggta ctgagtctaa gcactgcggt aaaggagtta gtagaaaaca         180
gtctggatgc tggtgccact aatattgatc taaagcttaa ggactatgga gtggatctta         240
ttgaagtttc agacaatgga tgtgggtag aagaagaaaa cttcgaaggc ttaactctga          300
aacatcacac atctaagatt caagagtttg ccgacctaac tcaggttgaa acttttggct         360
ttcgggggga agctctgagc tcactttgtg cactgagcga tgtcaccatt tctacctgcc         420
acgcatcggc gaaggttgga acttga                                              426
```

Mutant antibodies showing increased affinity for antigen were sequenced and compared to the sequence of the wild-type (WT) H36 parental antibody. It has been discovered that alterations of amino acids to proline has the effect of increasing affinity for antigen when introduced into the variable region of either the light chain or heavy chain of the immunoglobulin molecule. While not wishing to be bound by any particular theory of operation, it is believed that the prolines introduce a localized area of rigidity and lend stability to the immunoglobulin molecule, particularly to the regions around the antigen combining sites.

Thus, the invention provides for a method to increase the affinity of antibodies comprising replacing amino acids of the variable domain heavy and/or light chain with proline or hydroxyproline (collectively referred to as "proline"). In some embodiments, the substitution of prolines is in the heavy chain variable domain. In some embodiments, the substitution of prolines is in the light chain variable domain. In other embodiments, the substitution of proline is in both the heavy chain and the light chain of the variable domain of the immunoglobulin molecule. In some embodiments, the proline substitutes for another amino acid having a non-polar sidechain (e.g., glycine, alanine, valine, leucine, isoleucine, phenylalanine, methionine, tryptophan and cysteine). In some embodiments, further exchanges of amino acids having non-polar sidechains with other amino acids having non-polar sidechains may also confer increased affinity of the antibody for the antigen. In some embodiments, the amino acid substitutions are in a framework region of the heavy chain. In other embodiments, the amino acid substitutions are in a framework region of the light chain. In other embodiments, the amino acid substitutions are in a framework region of both the heavy and light chain. In some embodiments, the amino acid substitutions are in the first framework region (FR1) of the heavy chain. In other embodiments, the amino acid substitution is in the second framework region (FR2) of the heavy chain. In other embodiments, the amino acid substitution is in the third framework region (FR3) of the heavy chain. In other embodiments, the amino acid substitution is in the fourth framework region (FR4) of the heavy chain. In some embodiments, the amino acid substitutions are in the first framework region (FR1) of the light chain. In other embodiments, the amino acid substitution is in the second framework region (FR2) of the light chain. In other embodiments, the amino acid substitution is in the third framework region (FR3) of the light chain. In other embodiments, the amino acid substitution is in the fourth framework region (FR4) of the light chain.

In certain embodiments of the invention, a proline substitutes for an alanine at position 6 of SEQ ID NO:18. In other embodiments, proline substitutes for alanine at position 6 of SEQ ID NO:18 and the glycine at position 9 of SEQ ID NO:18, and/or the lysine at position 10 of SEQ ID NO:18 is substituted with an amino acid having a non-polar side chain (preferably, valine and arginine, respectively). In other embodiments, proline substitutes for leucine at position 22 of SEQ ID NO:21. For further information on the background of the invention the following references may be consulted, each of which is incorporated herein by reference in its entirety:

1. Glaser, V. (1996) Can ReoPro repolish tarnished monoclonal therapeutics? Nat. Biotechol. 14:1216-1217.
2. Weiner, L. M. (1999) Monoclonal antibody therapy of cancer. Semin. Oncol. 26:43-51.
3. Saez-Llorens, X. E. et al. (1998) Safety and pharmacokinetics of an intramuscular humanized monoclonal antibody to respiratory syncytial virus in premature infants and infants with bronchopulmonary dysplasia. Pediat. Infect. Dis. J. 17:787-791.
4. Shield, C. F. et al. (1996) A cost-effective analysis of OKT3 induction therapy in cadaveric kidney transplantation. Am. J. Kidney Dis. 27:855-864.

5. Khazaeli, M. B. et al. (1994) Human immune response to monoclonal antibodies. J. Immunother. 15:42-52.
6. Emery, S. C. and W. J. Harris "Strategies for humanizing antibodies" In: Antibody Engineering C.A.K. Borrebaeck (Ed.) Oxford University Press, N.Y. 1995, pp. 159-183.
7. U.S. Pat. No. 5,530,101 to Queen and Selick.
8. Reff, M. E. (1993) High-level production of recombinant immunoglobulins in mammalian cells. Curr. Opin. Biotechnol. 4:573-576.
9. Neuberger, M. and M. Gruggermann, (1997) Monoclonal antibodies. Mice perform a human repertoire. Nature 386: 25-26.
10. Fiedler, U. and U. Conrad (1995) High-level production and long-term storage of engineered antibodies in transgenic tobacco seeds. Bio/Technology 13:1090-1093.
11. Baker S. M. et al. (1995) Male defective in the DNA mismatch repair gene PMS2 exhibit abnormal chromosome synapsis in meiosis. Cell 82:309-319.
12. Bronner, C. E. et al. (1994) Mutation in the DNA mismatch repair gene homologue hMLH1 is associated with hereditary non-polyposis colon cancer. Nature 368:258-261.
13. de Wind N. et al. (1995) Inactivation of the mouse Msh2 gene results in mismatch repair deficiency, methylation tolerance, hyperrecombination, and predisposition to cancer. Cell 82:321-300.
14. Drummond, J. T. et al. (1995) Isolation of an hMSH2-p160 heterodimer that restores mismatch repair to tumor cells. Science 268:1909-1912.
15. Modrich, P. (1994) Mismatch repair, genetic stability, and cancer. Science 266: 1959-1960.
16. Nicolaides, N. C. et al. (1998) A Naturally Occurring hPMS2 Mutation Can Confer a Dominant Negative Mutator Phenotype. Mol. Cell. Biol. 18:1635-1641.
17. Prolla, T. A. et al. (1994) MLH1, PMS1, and MSH2 Interaction during the initiation of DNA mismatch repair in yeast. Science 264:1091-1093.
18. Strand, M. et al. (1993) Destabilization of tracts of simple repetitive DNA in yeast by mutations affecting DNA mismatch repair. Nature 365:274-276.
19. Su, S. S., R. S. Lahue, K. G. Au, and P. Modrich (1988) Mispair specificity of methyl directed DNA mismatch corrections in vitro. J. Biol. Chem. 263:6829-6835.
20. Parsons, R. et al. (1993) Hypermutability and mismatch repair deficiency in RER+ tumor cells. Cell 75:1227-1236.
21. Papadopoulos, N. et al. (1993) Mutation of a mutL homolog is associated with hereditary colon cancer. Science 263:1625-1629.
22. Perucho, M. (1996) Cancer of the microsatellite mutator phenotype. Biol. Chem. 377:675-684.
23. Nicolaides N. C., K. W. Kinzler, and B. Vogelstein (1995) Analysis of the 5' region of PMS2 reveals heterogenous transcripts and a novel overlapping gene. Genomics 29:329-334.
24. Nicolaides, N. C. et al. (1995) Genomic organization of the human PMS2 gene family. Genomics 30:195-206.
25. Palombo, F. et al. (1994) Mismatch repair and cancer. Nature 36:417.
26. Eshleman J. R. and S. D. Markowitz (1996) Mismatch repair defects in human carcinogenesis. Hum. Mol. Genet. 5:1489-494.
27. Liu, T. et al. (2000) Microsatellite instability as a predictor of a mutation in a DNA mismatch repair gene in familial colorectal cancer. Genes Chromosomes Cancer 27:17-25.
28. Nicolaides, N. C. et al. (1992) The Jun family members, c-JUN and JUND, transactivate the human c-myb promoter via an Ap1 like element. J. Biol. Chem. 267: 19665-19672.
29. Shields, R. L. et al. (1995) Anti-IgE monoclonal antibodies that inhibit allergen-specific histamine release. Int. Arch. Allergy Immunol. 107:412-413.
30. Frigerio L. et al. (2000) Assembly, secretion, and vacuolar delivery of a hybrid immunoglobulin in plants. Plant Physiol. 123:1483-1494.
31. Bignami M, (2000) Unmasking a killer: DNA 0(6)-methylguanine and the cytotoxicity of methylating agents. Mutat. Res. 462:71-82.
32. Drummond, J. T. et al. (1996) Cisplatin and adriamycin resistance are associated with MutLα and mismatch repair deficiency in an ovarian tumor cell line. J. Biol. Chem. 271:9645-19648.
33. Galio, L. et al. (1999) ATP hydrolysis-dependent formation of a dynamic ternary nucleoprotein complex with MutS and MutL. Nucl. Acids Res. 27:2325-23231.

The above disclosure generally describes the present invention. A more complete understanding can be obtained by reference to the following specific examples which are provided herein for purposes of illustration only, and are not intended to limit the scope of the invention.

EXAMPLE 1

Stable Expression of Dominant Negative MMR Genes in Hybridoma Cells

It has been previously shown by Nicolaides et al. (Nicolaides et al. (1998) A Naturally Occurring hPMS2 Mutation Can Confer a Dominant Negative Mutator Phenotype Mol. Cell. Biol. 18:1635-1641) that the expression of a dominant negative allele in an otherwise MMR proficient cell could render these host cells MMR deficient. The creation of MMR deficient cells can lead to the generation of genetic alterations throughout the entire genome of a host organism's offspring, yielding a population of genetically altered offspring or siblings that may produce biochemicals with altered properties. This patent application teaches of the use of dominant negative MMR genes in antibody-producing cells, including but not limited to rodent hybridomas, human hybridomas, chimeric rodent cells producing human immunoglobulin gene products, human cells expressing immunoglobulin genes, mammalian cells producing single chain antibodies, and prokaryotic cells producing mammalian immunoglobulin genes or chimeric immunoglobulin molecules such as those contained within single-chain antibodies. The cell expression systems described above that are used to produce antibodies are well known by those skilled in the art of antibody therapeutics.

To demonstrate the ability to create MMR defective hybridomas using dominant negative alleles of MMR genes, we first transfected a mouse hybridoma cell line that is known to produce an antibody directed against the human IgE protein with an expression vector containing the human PMS2 (cell line referred to as HBPMS2), the previously published dominant negative PMS2 mutant referred herein as PMS134 (cell line referred to as HB134), or with no insert (cell line referred to as HBvec). The results showed that the PMS134 mutant could indeed exert a robust dominant negative effect, resulting in biochemical and genetic manifestations of MMR deficiency. Unexpected was the finding that the full length PMS2 also resulted in a lower MMR activity while no effect was seen in cells containing the empty vector. A brief description of the methods is provided below.

The MMR proficient mouse H36 hybridoma cell line was transfected with various hPMS2 expression plasmids plus reporter constructs for assessing MMR activity. The MMR genes were cloned into the pEF expression vector, which contains the elongation factor promoter upstream of the cloning site followed by a mammalian polyadenylation signal. This vector also contains the NEOr gene that allows for selection of cells retaining this plasmid. Briefly, cells were transfected with 1 μg of each vector using polyliposomes following the manufacturer's protocol (Life Technologies). Cells were then selected in 0.5 mg/ml of G418 for 10 days and G418 resistant cells were pooled together to analyze for gene expression. The pEF construct contains an intron that separates the exon 1 of the EF gene from exon 2, which is juxtaposed to the 5' end of the polylinker cloning site. This allows for a rapid reverse transcriptase polymerase chain reaction (RT-PCR) screen for cells expressing the spliced products. At day 17, 100,000 cells were isolated and their RNA extracted using the trizol method as previously described (Nicolaides N. C., Kinzler, K. W., and Vogelstein, B. (1995) Analysis of the 5' region of PMS2 reveals heterogeneous transcripts and a novel overlapping gene. *Genomics* 29:329-334). RNAs were reverse transcribed using Superscript II (Life Technologies) and PCR amplified using a sense primer located in exon 1 of the EF gene (5'-ttt cgc aac ggg ttt gcc g-3') (SEQ ID NO:23) and an antisense primer (5'-gtt tca gag tta agc ctt cg-3') (SEQ ID NO:24) centered at nt 283 of the published human PMS2 cDNA, which will detect both the full length as well as the PMS134 gene expression. Reactions were carried out using buffers and conditions as previously described (Nicolaides, N. C., et al. (1995) Genomic organization of the human PMS2 gene family. *Genomics* 30:195-206), using the following amplification parameters: 94° C. for 30 sec, 52° C. for 2 min, 72° C. for 2 min, for 30 cycles. Reactions were analyzed on agarose gels. FIG. 1 shows a representative example of PMS expression in stably transduced H36 cells.

Expression of the protein encoded by these genes were confirmed via western blot using a polyclonal antibody directed to the first 20 amino acids located in the N-terminus of the protein following the procedures previously described (data not shown) (Nicolaides et al. (1998) A Naturally Occurring hPMS2 Mutation Can Confer a Dominant Negative Mutator Phenotype. *Mol. Cell. Biol.* 18:1635-1641).

EXAMPLE 2 hPMS134 Causes a Defect in MMR Activity and Hypermutability in Hybridoma Cells

A hallmark of MMR deficiency is the generation of unstable microsatellite repeats in the genome of host cells. This phenotype is referred to as microsatellite instability (MI) (Modrich, P. (1994) Mismatch repair, genetic stability, and cancer *Science* 266:1959-1960; Palombo, F., et al. (1994) Mismatch repair and cancer *Nature* 36:417). MI consists of deletions and/or insertions within repetitive mono-, di- and/or tri-nucleotide repetitive sequences throughout the entire genome of a host cell. Extensive genetic analyses of eukaryotic cells have found that the only biochemical defect that is capable of producing MI is defective MMR (Strand, M., et al. (1993) Destabilization of tracts of simple repetitive DNA in yeast by mutations affecting DNA mismatch repair *Nature* 365:274-276; Perucho, M. (1996) Cancer of the microsatellite mutator phenotype. *Biol Chem.* 377:675-684; Eshleman J. R., and Markowitz, S. D. (1996) Mismatch repair defects in human carcinogenesis. *Hum. Mol. Genet.* 5:1489-494). In light of this unique feature that defective MMR has on promoting MI, it is now used as a biochemical marker to survey for lack of MMR activity within host cells (Perucho, M. (1996) Cancer of the microsatellite mutator phenotype. *Biol Chem.* 377:675-684; Eshleman J. R., and Markowitz, S. D. (1996) Mismatch repair defects in human carcinogenesis. *Hum. Mol. Genet.* 5:1489-494; Liu, T., et al. (2000) Microsatellite instability as a predictor of a mutation in a DNA mismatch repair gene in familial colorectal cancer *Genes Chromosomes Cancer* 27: 17-25).

A method used to detect MMR deficiency in eukaryotic cells is to employ a reporter gene that has a polynucleotide repeat inserted within the coding region that disrupts its reading frame due to a frame shift. In the case where MMR is defective, the reporter gene will acquire random mutations (i.e. insertions and/or deletions) within the polynucleotide repeat yielding clones that contain a reporter with an open reading frame. We have employed the use of an MMR-sensitive reporter gene to measure for MMR activity in HBvec, HBPMS2, and HBPMS134 cells. The reporter construct used the pCAR-OF, which contains a hygromycin resistance (HYG) gene plus a β-galactosidase gene containing a 29 bp out-of-frame poly-CA tract at the 5' end of its coding region. The pCAR-OF reporter would not generate β-galactosidase activity unless a frame-restoring mutation (i.e., insertion or deletion) arose following transfection. HBvec, HBPMS2, and HB134 cells were each transfected with pCAR-OF vector in duplicate reactions following the protocol described in Example 1. Cells were selected in 0.5 mg/ml G418 and 0.5 mg/ml HYG to select for cells retaining both the MMR effector and the pCAR-OF reporter plasmids. All cultures transfected with the pCAR vector resulted in a similar number of HYG/G418 resistant cells. Cultures were then expanded and tested for β-galactosidase activity in situ as well as by biochemical analysis of cell extracts. For in situ analysis, 100,000 cells were harvested and fixed in 1% gluteraldehyde, washed in phosphate buffered saline solution and incubated in 1 ml of X-gal substrate solution [0.15 M NaCl, 1 mM $MgCl_2$, 3.3 mM $K_4Fe(CN)_6$, 3.3 mM $K_3Fe(CN)_6$, 0.2% X-Gal] in 24 well plates for 2 hours at 37° C. Reactions were stopped in 500 mM sodium bicarbonate solution and transferred to microscope slides for analysis. Three fields of 200 cells each were counted for blue (β-galactosidase positive cells) or white (β-galactosidase negative cells) to assess for MMR inactivation. Table 1 shows the results from these studies. While no β-galactosidase positive cells were observed in HBvec cells, 10% of the cells per field were β-galactosidase positive in HB134 cultures and 2% of the cells per field were β-galactosidase positive in HBPMS2 cultures.

Cell extracts were prepared from the above cultures to measure β-galactosidase using a quantitative biochemical assay as previously described (Nicolaides et al. (1998) A Naturally Occurring hPMS2 Mutation Can Confer a Dominant Negative Mutator Phenotype *Mol. Cell. Biol.* 18:1635-1641; Nicolaides, N. C., et al. (1992) The Jun family members, c-JUN and JUND, transactivate the human c-myb promoter via an Ap1 like element. *J. Biol. Chem.* 267:19665-19672). Briefly, 100,000 cells were collected, centrifuged and resuspended in 200 μls of 0.25M Tris, pH 8.0. Cells were lysed by freeze/thawing three times and supernatants collected after microfugation at 14,000 rpms to remove cell debris. Protein content was determined by spectrophotometric analysis at $OD^{280}$. For biochemical assays, 20 μg of protein was added to buffer containing 45 mM 2-mercaptoethanol, 1 mM $MgCl_2$, 0.1 M $NaPO_4$ and 0.6 mg/ml Chlorophenol red-β-D-galactopyranoside (CPRG, Boehringer Mannheim).

Figure 2:
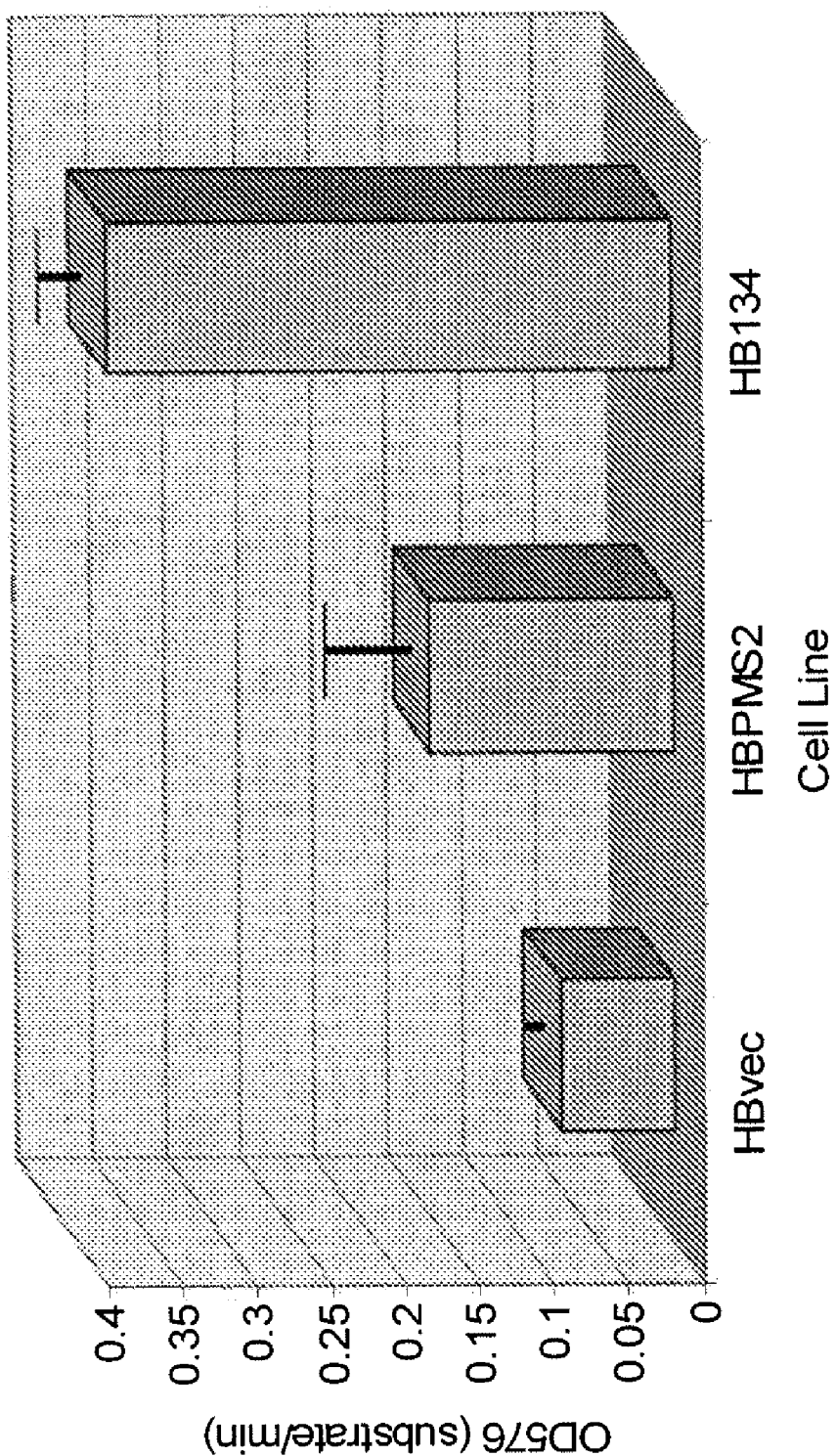
FIG. 2 illustrates creation of genetically hypermutable hybridoma cells. Dominant negative MMR gene alleles were expressed in cells expressing a MMR-sensitive reporter gene. Dominant negative alleles such as PMS134 and the expression of MMR genes from other species results in antibody producer cells with a hypermutable phenotype that can be used to produce genetically altered immunoglobulin genes with enhanced biochemical features as well as lines with increased Ig expression and/or secretion. Values shown represent the amount of converted CPRG substrate which is reflective of the amount of function β-galactosidase contained within the cell from genetic alterations within the pCAR-OF reporter gene. Higher amounts of β-galactosidase activity reflect a higher mutation rate due to defective MMR.

Reactions were incubated for 1 hour, terminated by the addition of 0.5 M $Na_2CO_3$, and analyzed by spectrophotometry at 576 nm. H36 cell lysates were used to subtract out background. FIG. 2 shows the β-galactosidase activity in extracts from the various cell lines. As shown, the HB134 cells produced the highest amount of α-galactosidase, while no activity was found in the HBvec cells containing the pCAR-OF. These data demonstrate the ability to generate MMR defective hybridoma cells using dominant negative MMR gene alleles.

Table 1. β-galactosidase expression of HBvec, HBPMS2 and HB134 cells transfected with pCAR-OF reporter vectors. Cells were transfected with the pCAR-OF β-galactosidase reporter plasmid. Transfected cells were selected in hygromycin and G418, expanded and stained with X-gal solution to measure for beta-galactosidase activity (blue colored cells). 3 fields of 200 cells each were analyzed by microscopy. The results below represent the mean +/− standard deviation of these experiments.

TABLE 1

| CELL LINE | # BLUE CELLS |
| --- | --- |
| HBvec | 0 +/− 0 |
| HBPMS2 | 4 +/− 1 |
| HB134 | 20 +/− 3 |

EXAMPLE 3

Figure 3:
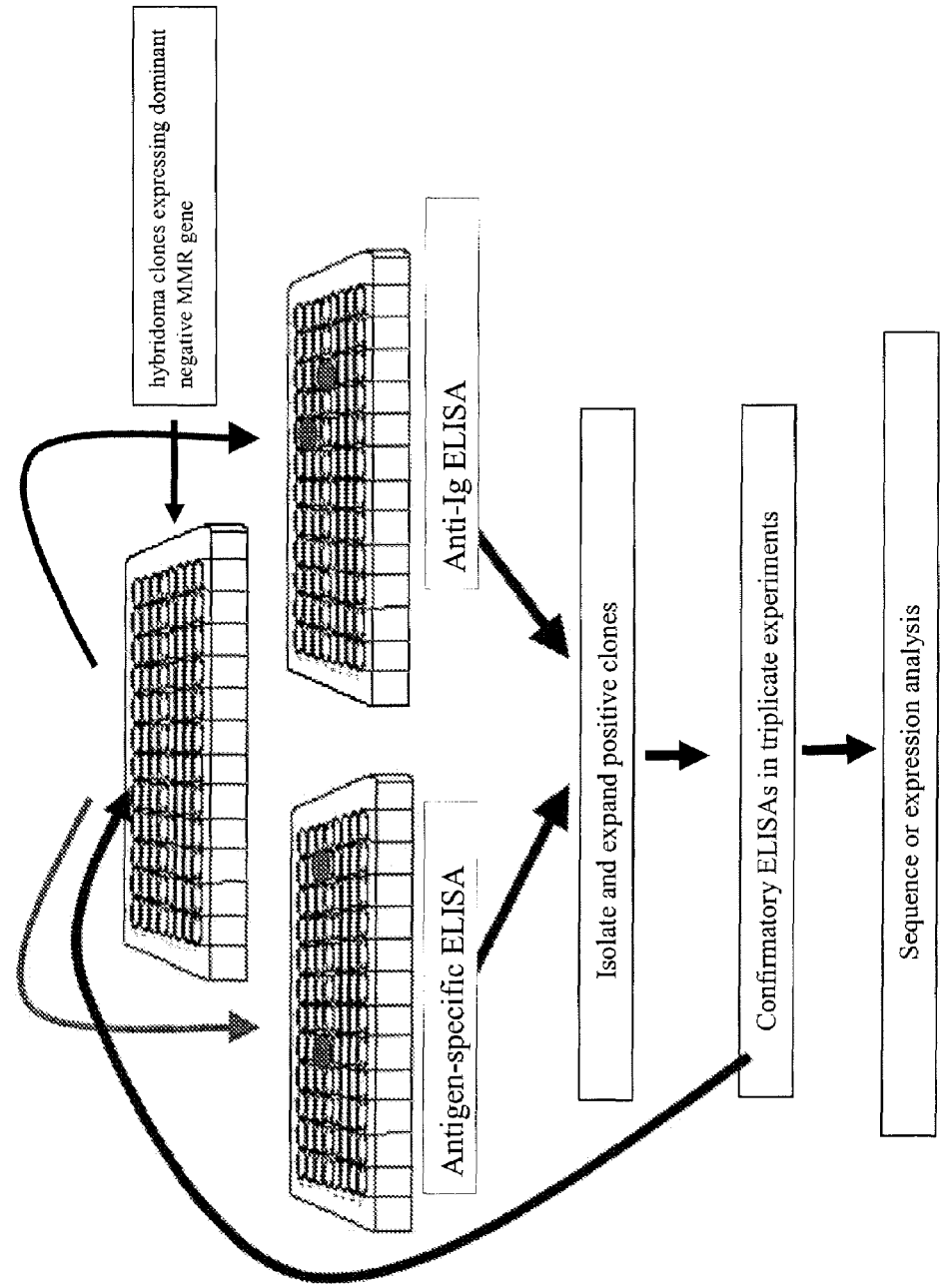
FIG. 3 shows a screening method for identifying antibody-producing cells containing antibodies with increased binding activity and/or increased expression/secretion

Screening Strategy to Identify Hybridoma Clones Producing Antibodies with Higher Binding Affinities and/or Increased Immunoglobulin Production An application of the methods presented within this document is the use of MMR deficient hybridomas or other immunoglobulin-producing cells to create genetic alterations within an immunoglobulin gene that will yield antibodies with altered biochemical properties. An illustration of this application is demonstrated within this example whereby the HB134 hybridoma (see Example 1), which is a MMR-defective cell line that produces an anti-human immunoglobulin type E (hIgE) MAb, is grown for 20 generations and clones are isolated in 96-well plates and screened for hIgE binding. FIG. 3 outlines the screening procedure to identify clones that produce high affinity MAbs, which is presumed to be due to an alteration within the light or heavy chain variable region of the protein. The assay employs the use of a plate Enzyme Linked Immunosorbant Assay (ELISA) to screen for clones that produce high-affinity MAbs. 96-well plates containing single cells from HBvec or HB134 pools are grown for 9 days in growth medium (RPMI 1640 plus 10% fetal bovine serum) plus 0.5 mg/ml G418 to ensure clones retain the expression vector. After 9 days, plates are screened using an hIgE plate ELISA, whereby a 96 well plate is coated with 50 µls of a 1 µg/ml hIgE solution for 4 hours at 4° C. Plates are washed 3 times in calcium and magnesium free phosphate buffered saline solution ($PBS^{-/-}$) and blocked in 100 µls of $PBS^{-/-}$ with 5% dry milk for 1 hour at room temperature. Wells are rinsed and incubated with 100 µls of a PBS solution containing a 1:5 dilution of conditioned medium from each cell clone for 2 hours. Plates are then washed 3 times with $PBS^{-/-}$ and incubated for 1 hour at room temperature with 50 µls of a $PBS^{-/-}$ solution containing 1:3000 dilution of a sheep anti-mouse horse radish peroxidase (HRP) conjugated secondary antibody. Plates are then washed 3 times with $PBS^{-/-}$ and incubated with 50 µls of TMB-HRP substrate (BioRad) for 15 minutes at room temperature to detect amount of antibody produced by each clone. Reactions are stopped by adding 50 µls of 500 mM sodium bicarbonate and analyzed by OD at 415 nm using a BioRad plate reader. Clones exhibiting an enhanced signal over background cells (H36 control cells) are then isolated and expanded into 10 ml cultures for additional characterization and confirmation of ELISA data in triplicate experiments. ELISAs are also performed on conditioned medium (CM) from the same clones to measure total Ig production within the conditioned medium of each well. Clones that produce an increased ELISA signal and have increased antibody levels are then further analyzed for variants that over-express and/or over-secrete antibodies as described in Example 4. Analysis of five 96-well plates each from HBvec or HB134 cells have found that a significant number of clones with a higher Optical Density (OD) value is observed in the MMR-defective HB134 cells as compared to the HBvec controls. FIG. 4 shows a representative example of HB134 clones producing antibodies that bind to specific antigen (in this case IgE) with a higher affinity. FIG. 4 provides raw data from the analysis of 96 wells of HBvec (left graph) or HB134 (right graph) which shows 2 clones from the HB134 plate to have a higher OD reading due to 1) genetic alteration of the antibody variable domain that leads to an increased binding to IgE antigen, or 2) genetic alteration of a cell host that leads to over-production/secretion of the antibody molecule. Anti-Ig ELISA found that the two clones, shown in FIG. 4 have Ig levels within their CM similar to the surrounding wells exhibiting lower OD values. These data suggest that a genetic alteration occurred within the antigen-binding domain of the antibody which in turn allows for higher binding to antigen.

Clones that produced higher OD values as determined by ELISA were further analyzed at the genetic level to confirm that mutations within the light or heavy chain variable region have occurred that lead to a higher binding affinity hence yielding to a stronger ELISA signal. Briefly, 100,000 cells are harvested and extracted for RNA using the Triazol method as described above. RNAs are reverse-transcribed using Superscript II as suggested by the manufacturer (Life Technology) and PCR-amplified for the antigen-binding sites contained within the variable light and heavy chains. Because of the heterogeneous nature of these genes, the following degenerate primers are used to amplify light and heavy chain alleles from the parent H36 strain.

```
                                        (SEQ ID NO: 1)
Light chain sense:
5'-GGA TTT TCA GGT GCA GAT TTT CAG-3'

(SEQ ID NO: 2)
Light chain antisense:
5'-ACT GGA TGG TGG GAA GAT GGA-3'

(SEQ ID NO: 3)
Heavy chain sense:
5'-A(G/T) GTN (A/C)AG CTN CAG (C/G)AG TC-3'

(SEQ ID NO: 4)
Heavy chain antisense:
5'-TNC CTT G(A/G)C CCC AGT A(G/A)(A/T)C-3'
```

PCR reactions using degenerate oligonucleotides are carried out at 94° C. for 30 sec, 52° C. for 1 min, and 72° C. for 1 min for 35 cycles. Products are analyzed on agarose gels. Products of the expected molecular weights are purified from the gels by Gene Clean (Bio 101), cloned into T-tailed vectors, and sequenced to identify the wild type sequence of the variable light and heavy chains. Once the wild type sequence has been determined, non-degenerate primers were made for RT-PCR amplification of positive HB134 clones. Both the light and heavy chains were amplified, gel purified and sequenced using the corresponding sense and antisense primers. The sequencing of RT-PCR products gives representative sequence data of the endogenous immunoglobulin gene and not due to PCR-induced mutations. Sequences from clones were then compared to the wild type sequence for sequence comparison. An example of the ability to create in vivo mutations within an immunoglobulin light or heavy chain is shown in FIG. 5, where HB134 clone 92 was identified by ELISA to have an increased signal for hIgE. The light chain was amplified using specific sense and antisense primers. The light chain was RT-PCR amplified and the resulting product was purified and analyzed on an automated ABI377 sequencer. As shown in clone A, a residue-4 upstream of the CDR region 3 had a genetic change from ACT to TCT, which results in a Thr to Ser change within the framework region just preceding the CDR#3. In clone B, a residue-6 upstream of the CDR region had a genetic change from CCC to CTC, which results in a Pro to Leu change within framework region preceding CDR#2.

The ability to generate random mutations in immunoglobulin genes or chimeric immunoglobulin genes is not limited to hybridomas. Nicolaides et al. (Nicolaides et al. (1998) A Naturally Occurring hPMS2 Mutation Can Confer a Dominant Negative Mutator Phenotype *Mol. Cell. Biol.* 18:1635-1641) has previously shown the ability to generate hypermutable hamster cells and produce mutations within an endogenous gene. A common method for producing humanized antibodies is to graft CDR sequences from a MAb (produced by immunizing a rodent host) onto a human Ig backbone, and transfection of the chimeric genes into Chinese Hamster Ovary (CHO) cells which in turn produce a functional Ab that is secreted by the CHO cells (Shields, R. L., et al. (1995) Anti-IgE monoclonal antibodies that inhibit allergen-specific histamine release. *Int. Arch. Allergy Immunol.* 107:412-413). The methods described within this application are also useful for generating genetic alterations within Ig genes or chimeric Igs transfected within host cells such as rodent cell lines, plants, yeast and prokaryotes (Frigerio L, et al. (2000) Assembly, secretion, and vacuolar delivery of a hybrid immunoglobulin in plants. *Plant Physiol.* 123:1483-1494).

These data demonstrate the ability to generate hypermutable hybridomas, or other Ig producing host cells that can be grown and selected, to identify structurally altered immunoglobulins yielding antibodies with enhanced biochemical properties, including but not limited to increased antigen binding affinity. Moreover, hypermutable clones that contain missense mutations within the immunoglobulin gene that result in an amino acid change or changes can be then further characterized for in vivo stability, antigen clearance, on-off binding to antigens, etc. Clones can also be further expanded for subsequent rounds of in vivo mutations and can be screened using the strategy listed above.

The use of chemical mutagens to produce genetic mutations in cells or whole organisms are limited due to the toxic effects that these agents have on "normal" cells. The use of chemical mutagens such as MNU in MMR defective organisms is much more tolerable yielding to a 10 to 100 fold increase in genetic mutation over MMR deficiency alone (Bignami M, (2000) Unmasking a killer: DNA O(6)-methylguanine and the cytotoxicity of methylating agents. *Mutat. Res.* 462:71-82). This strategy allows for the use of chemical mutagens to be used in MMR-defective Ab producing cells as a method for increasing additional mutations within immunoglobulin genes or chimeras that may yield functional Abs with altered biochemical properties such as enhanced binding affinity to antigen, etc.

EXAMPLE 4

Generation of Antibody Producing Cells with Enhanced Antibody Production

Analysis of clones from H36 and HB134 following the screening strategy listed above has identified a significant number of clones that produce enhanced amounts of antibody into the medium. While a subset of these clones gave higher Ig binding data as determined by ELISA as a consequence of mutations within the antigen binding domains contained in the variable regions, others were found to contain "enhanced" antibody production. A summary of the clones producing enhanced amounts of secreted MAb is shown in TABLE 2, where a significant number of clones from HB134 cells were found to produce enhanced Ab production within the conditioned medium as compared to H36 control cells.

TABLE 2. Generation of hybridoma cells producing high levels of antibody. HB134 clones were assayed by ELISA for elevated Ig levels. Analysis of 480 clones showed that a significant number of clones had elevated MAb product levels in their CM. Quantification showed that several of these clones produced greater than 500 ngs/ml of MAb due to either enhanced expression and/or secretion as compared to clones from the H36 cell line.

TABLE 2

| Production of MAb in CM from H36 and HB134 clones. | | |
|---|---|---|
| Cell Line | % clones > 400 ng/ml | % clones > 500 ng/ml |
| H36 | 1/480 = 0.2% | 0/480 = 0% |
| HB134 | 50/480 = 10% | 8/480 = 1.7% |

Figure 6:
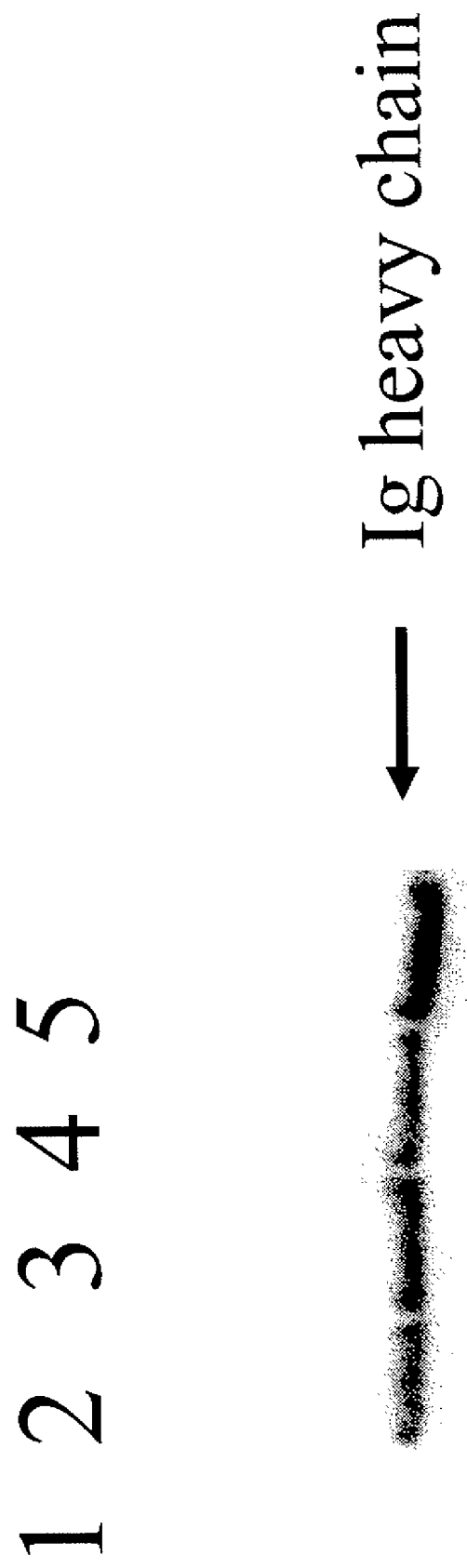
FIG. 6 shows generation of MMR-defective clones with enhanced steady state Ig protein levels. A Western blot of heavy chain immunoglobulins from HB134 clones with high levels of MAb (>500 ngs/ml) within the conditioned medium shows that a subset of clones express higher steady state levels of immunoglobulins (Ig). The H36 cell line was used as a control to measure steady state levels in the parental strain. Lane 1: fibroblast cells (negative control); Lane 2: H36 cell; Lane 3: HB134 clone with elevated MAb levels; Lane 4: HB134 clone with elevated MAb levels; Lane 5: HB134 clone with elevated MAb levels.

Cellular analysis of HB134 clones with higher MAb levels within the conditioned medium (CM) were analyzed to determine if the increased production was simply due to genetic alterations at the Ig locus that may lead to over-expression of the polypeptides forming the antibody, or due to enhanced secretion due to a genetic alteration affecting secretory pathway mechanisms. To address this issue, we expanded three HB134 clones that had increased levels of antibody within their CM. 10,000 cells were prepared for western blot analysis to assay for intracellular steady state Ig protein levels (FIG. 6). In addition, H36 cells were used as a standard reference (Lane 2) and a rodent fibroblast (Lane 1) was used as an Ig negative control. Briefly, cells were pelleted by centrifugation and lysed directly in 300 µl of SDS lysis buffer (60 mM Tris, pH 6.8, 2% SDS, boo glycerol, 0.1 M 2-mercaptoethanol, 0.001% bromophenol blue) and boiled for 5 minutes. Lysate proteins were separated by electrophoresis on 4-12% NuPAGE® gels (Invitrogen, Carlsbad, Calif.) (for analysis of Ig heavy chain. Gels were electroblotted onto Immobilon®-P filters (Millipore) in 48 mM Tris base, 40 mM glycine, 0.0375% SDS, 20% methanol and blocked at room temperature for 1 hour in Tris-buffered saline (TBS) plus 0.050% Tween-20™ reagent (polysorbate-20) and 500 condensed milk. Filters were probed with a 1:10,000 dilution of sheep anti-mouse horseradish peroxidase conjugated monoclonal antibody in TBS buffer and detected by chemiluminescence using Supersignal® substrate (Pierce). Experiments were repeated in duplicates to ensure reproducibility. FIG. 6 shows a representative analysis where a subset of clones had enhanced Ig production which accounted for increased Ab production (Lane 5) while others had a similar steady state level as the control sample, yet had higher levels of Ab within the CM. These data suggest a mechanism whereby a subset of HB134 clones contained a genetic alteration that in turn produces elevated secretion of antibody.

The use of chemical mutagens to produce genetic mutations in cells or whole organisms are limited due to the toxic effects that these agents have on "normal" cells. The use of chemical mutagens such as MNU in MMR defective organisms is much more tolerable yielding to a 10 to 100 fold increase in genetic mutation over MMR deficiency alone (Bignami M, (2000) Unmasking a killer: DNA O(6)-methylguanine and the cytotoxicity of methylating agents. *Mutat. Res.* 462:71-82). This strategy allows for the use of chemical mutagens to be used in MMR-defective Ab producing cells as a method for increasing additional mutations within immunoglobulin genes or chimeras that may yield functional Abs with altered biochemical properties such as enhanced binding affinity to antigen, etc.

EXAMPLE 5

Establishment of Genetic Stability in Hybridoma Cells with New Output Trait

The initial steps of MMR are dependent on two protein complexes, called MutS-alpha and MutL-alpha (Nicolaides et al. (1998) A Naturally Occurring hPMS2 Mutation Can Confer a Dominant Negative Mutator Phenotype. *Mol. Cell. Biol.* 18:1635-1641). Dominant negative MMR alleles are able to perturb the formation of these complexes with downstream biochemicals involved in the excision and polymerization of nucleotides comprising the "corrected" nucleotides. Examples from this application show the ability of a truncated MMR allele (PMS134) as well as a full length human PMS2 when expressed in a hybridoma cell line is capable of blocking MMR resulting in a hypermutable cell line that gains genetic alterations throughout its entire genome per cell division. Once a cell line is produced that contains genetic alterations within genes encoding for an antibody, a single chain antibody, over expression of immunoglobulin genes and/or enhanced secretion of antibody, it is desirable to restore the genomic integrity of the cell host. This can be achieved by the use of inducible vectors whereby dominant negative MMR genes are cloned into such vectors, introduced into Ab producing cells and the cells are cultured in the presence of inducer molecules and/or conditions. Inducible vectors include but are not limited to chemical regulated promoters such as the steroid inducible MMTV, tetracycline regulated promoters, temperature sensitive MMR gene alleles, and temperature sensitive promoters.

The results described above lead to several conclusions. First, expression of hPMS2 and PMS134 results in an increase in microsatellite instability in hybridoma cells. That this elevated microsatellite instability is due to MMR deficiency was proven by evaluation of extracts from stably transduced cells. The expression of PMS 134 results in a polar defect in MMR, which was only observed using heteroduplexes designed to test repair from the 5' direction (no significant defect in repair from the 3' direction was observed in the same extracts) (Nicolaides et al. (1998) A Naturally Occurring hPMS2 Mutation Can Confer a Dominant Negative Mutator Phenotype. *Mol. Cell. Biol.* 18:1635-1641). Interestingly, cells deficient in hMLH1 also have a polar defect in MMR, but in this case preferentially affecting repair from the 3' direction (Drummond, J. T, et al. (1996) Cisplatin and adriamycin resistance are associated with MutLa and mismatch repair deficiency in an ovarian tumor cell line. *J. Biol. Chem.* 271:9645-19648). It is known from previous studies in both prokaryotes and eukaryotes that the separate enzymatic components mediate repair from the two different directions. Our results, in combination with those of Drummond et al. (Shields, R. L., et al. (1995) Anti-IgE monoclonal antibodies that inhibit allergen-specific histamine release. *Int. Arch Allergy Immunol.* 107:412-413), strongly suggest a model in which 5' repair is primarily dependent on hPMS2 while 3' repair is primarily dependent on hMLH1. It is easy to envision how the dimeric complex between PMS2 and MLH1 might set up this directionality. The combined results also demonstrate that a defect in directional MMR is sufficient to produce a MMR defective phenotype and suggests that any MMR gene allele is useful to produce genetically altered hybridoma cells, or a cell line that is producing Ig gene products. Moreover, the use of such MMR alleles will be useful for generating genetically altered Ig polypeptides with altered biochemical properties as well as cell hosts that produce enhanced amounts of antibody molecules.

Another method that is taught in this application is that ANY method used to block MMR can be performed to generate hypermutablility in an antibody-producing cell that can lead to genetically altered antibodies with enhanced biochemical features such as but not limited to increased antigen binding, enhanced pharmacokinetic profiles, etc. These processes can also to be used to generate antibody producer cells that have increased Ig expression as shown in Example 4, FIG. 6 and/or increased antibody secretion as shown in Table 2.

Figure 5B:
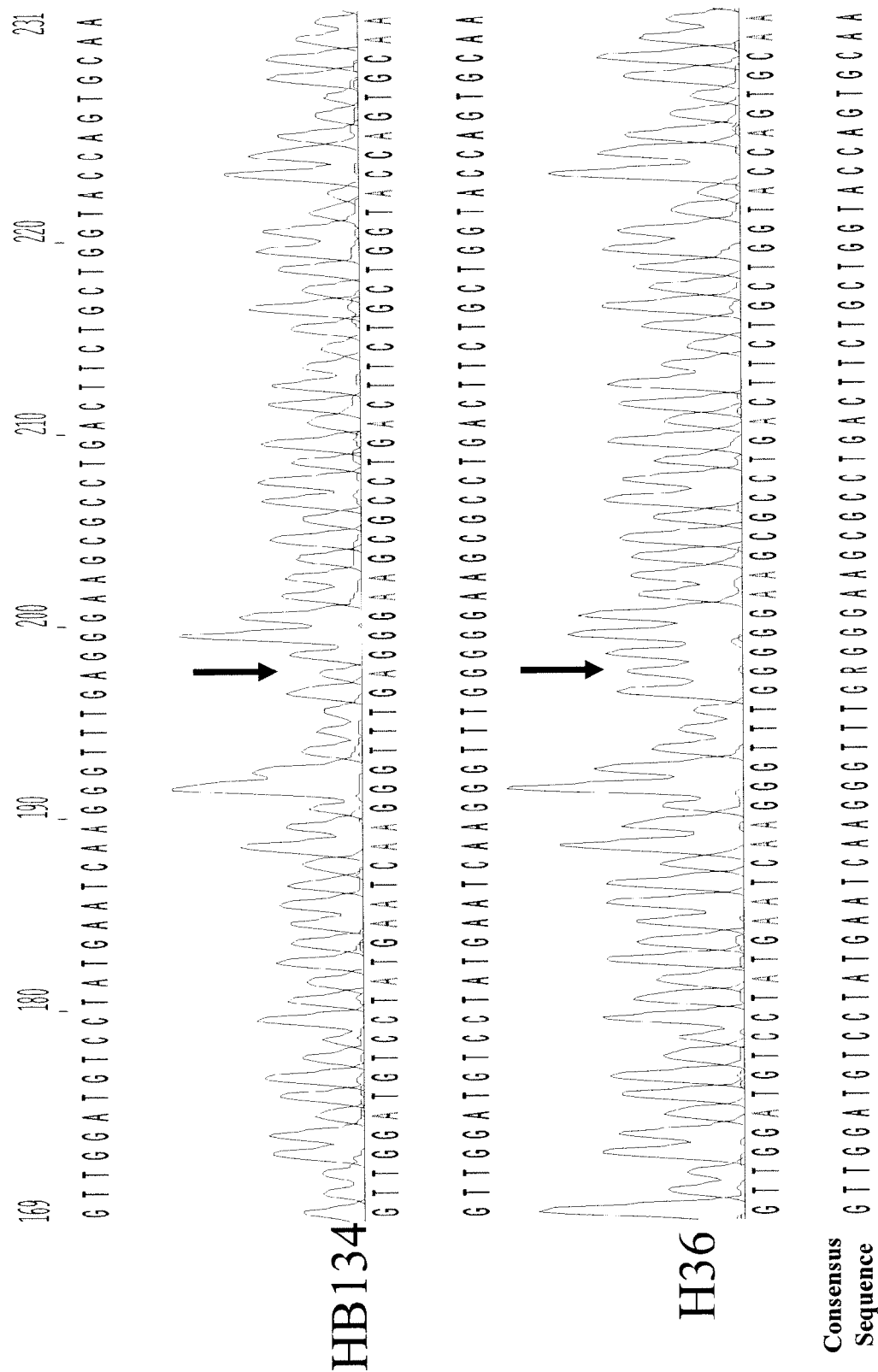
FIG. 5B illustrates sequence alteration within the variable chain of an antibody (a mutation within the light chain variable region in MMR-defective HB134 antibody producer cells). The HB134 sequence (SEQ ID NO:27) is shown above and below the tracing for the HB134 sequence, and the parental H36 sequence (SEQ ID NO:28) is shown above and below the H36 sequence tracing. A consensus sequence (SEQ ID NO:29) is shown at the bottom of the figure. Arrows indicate the nucleotide at which a mutation occurred in a subset of cells from a clone derived from HB134 cells. The change results in a Pro to Leu change within the light chain variable region.

In addition, we demonstrate the utility of blocking MMR in antibody producing cells to increase genetic alterations within Ig genes that may lead to altered biochemical features such as, but not limited to, increased antigen binding affinities (FIGS. 5A and 5B). The blockade of MMR in such cells can be through the use of dominant negative MMR gene alleles from any species including bacteria, yeast, protozoa, insects, rodents, primates, mammalian cells, and man. Blockade of MMR can also be generated through the use of antisense RNA or deoxynucleotides directed to any of the genes involved in the MMR biochemical pathway. Blockade of MMR can be through the use of polypeptides that interfere with subunits of the MMR complex including but not limited to antibodies. Finally, the blockade of MMR may be through the use chemicals such as but not limited to nonhydrolyzable ATP analogs, which have been shown to block MMR (Galio, L, et al. (1999) ATP hydrolysis-dependent formation of a dynamic ternary nucleoprotein complex with MutS and MutL. *Nucl. Acids Res.* 27:2325-23231).

EXAMPLE 6

Analysis of Genetic Sequence of Mutant H36 Cell Lines Producing High Affinity Antibodies The nucleic acid sequence of the light and heavy chains of the antibodies produced by the H36 mutant cell lines were examined for mutations within the immunoglobulin coding sequence that contribute to the increased affinity of the antibodies as compared to the parent clone. The results are shown in Table 3. The data show that proline substitutions in both the heavy and light chain variable domains contribute to increased affinity of the antibodies to antigen. A particular hot spot appears to be amino acid position 6 of SEQ ID NO:18 in which an amino acid substitution occurred changing the parental alanine to proline for HB91-47, HB134DRMA13, and HB134DRMA55. These three clones also had mutations at positions 9 and 10. In position 9, the parental valine was changed to glycine or arginine, while at position 10 of SEQ ID NO:18, the parental arginine was changed to lysine in both cases.

TABLE 3

| Clones | Chain | Sequence Change | Amino Acid Change | Mean ELISA | Affinity |
|---|---|---|---|---|---|
| H36 | | WT | None | 0.542 | 4.80E−08 |
| HB-134al | L | A > T | Thr > Ser | 1.632 | nd |
| HB91-34 | H | C insertion | Frame-shift | 0 | 0 |
| HB91-37 | L | T > C | Leu > Pro | 1.743 | 1.40E−09 |
| HB91-38 | H | T > A | Ser > Ser | 1.641 | nd |
| HB91-40 | H | A > G | Ala > Thr | 1.333 | nd |
| HB91-47 | H | Multiple | Ala > Pro, Val > Gly, Arg > Lys | 1.979 | 3.12E−09 |
| HB91-53 | H | TT > AA | Phe > Lys | 1.144 | nd |
| HB91-62 | H | A > G | Met > Gly | 0.218 | 6.60E−07 |
| HB91-71 | H | T > G | Met > Gly | 0.186 | nd |
| HB134DRMA13 | H | Multiple | Ala > Pro, Val > Gly, Arg > Lys, Thr > Ala, | 2.041 | nd |
| HB134DRMA14 | H | G > A, A > G | Arg > Lys, Thr > Ala | 1.211 | nd |
| HB134DRMA55 | H | Multiple | Ala > Pro, Val > Arg, Arg > Lys, Thr > Glu, Ser > Thr | 2.012 | nd |

The genetically altered antibodies show the following sequence differences and consensus sequence:

Amino acid Alignment of morphogenic HB91-47 Heavy Chain (SEQ ID NO:17), Parental H36 Heavy Chain (SEQ ID NO:18), and Consensus Heavy Chain Sequence (SEQ ID NO:19)

```
                        1                                   35
Morphogenic    (1)      LQQSGPELGKPGTSVKISCKASGYTFTNYGMNWVK
H36 parental   (1)      LQQSGAELVRPGTSVKISCKASGYTFTNYGMNWVK
Consensus      (1)      LQQSGXELXXPGTSVKISCKASGYTFTNYGMNWVK
                        |             FR1           |CDR1|

36                                  70
Morphogenic    (36)     QAPGKGLKWMGWINTYTGEPTYADDFKGRFAFSLE
H36 parental   (36)     QAPGKGLKWMGWINTYTGEPTYADDFKGRFAFSLE
Consensus      (36)     QAPGKGLKWMGWINTYTGEPTYADDFKGRFAFSLE
                        FR2       |      CDR2       |   FR3
```

Amino acid Alignment of Morphogenic HB91-37 Light Chain (SEQ ID NO:20), Parental H36 Light Chain (SEQ ID NO:21), and Consensus Light Chain Sequence (SEQ ID NO:22)

```
                        1                                   35
Morphogenic    (1)      SASSSVSSSYFHWYQQKSGASPKPLIHRTSNLASG
H36 parental   (1)      SASSSVSSSYFHWYQQKSGASLKPLIHRTSNLASG
Consensus      (1)      SASSSVSSSYFHWYQQKSGASXKPLIHRTSNLASG
                             CDR1    |    FR2     |  CDR2  |

36     45
Morphogenic    (36)     VPARFSGSGS
H36 parental   (36)     VPARFSGSGS
Consensus      (36)     VPARFSGSGS
                            FR3
```

The data shows that for the light chain, a substitution in the second framework region (FR2) of the light chain at position 22 of SEQ ID NO:21 to a proline increased the binding affinity of the antibody.

We claim:

1. A method of producing a monoclonal antibody having an increased affinity for the antigen to which it binds relative to a monoclonal antibody comprising a light chain variable region comprising the amino acid sequence of SEQ ID NO:21 and a heavy chain variable region comprising the amino acid sequence of SEQ ID NO:18 that binds said antigen, the method comprising: substituting with proline an amino acid in SEQ ID NO:21 within said monoclonal antibody comprising a light chain variable region comprising SEQ ID NO:21 and a heavy chain variable region comprising the amino acid sequence of SEQ ID NO:18, thereby generating a proline-substituted monoclonal antibody, determining the binding affinity of said proline-substituted monoclonal antibody for said antigen, comparing the binding affinity of said proline-substituted monoclonal antibody for said antigen to the binding affinity of said monoclonal antibody comprising a light chain variable region comprising the amino acid sequence of SEQ ID NO:21 and a heavy chain variable region comprising the amino acid sequence of SEQ ID NO:18 for said antigen, and selecting a proline-substituted antibody having increased affinity for said antigen relative to said monoclonal antibody comprising a light chain variable region comprising the amino acid sequence of SEQ ID NO:21 and a heavy chain variable region comprising the amino acid sequence of SEQ ID NO:18, thereby producing said monoclonal antibody having increased binding affinity for said antigen.

2. A method as claimed in claim 1, wherein said amino acid substituted with proline in SEQ ID NO:21 is an amino acid having a non-polar side chain.

3. A method as claimed in claim 1, wherein said amino acid substituted with proline in SEQ ID NO:21 is leucine.

4. A method as claimed in claim 1, wherein said amino acid substituted with proline in SEQ ID NO:21 is in the second framework region of the light chain of said monoclonal antibody comprising a light chain variable region comprising the amino acid sequence of SEQ ID NO:21 and a heavy chain variable region comprising the amino acid sequence of SEQ ID NO:18.

5. A method as claimed in claim 1, wherein said amino acid substituted with proline in SEQ ID NO:21 is in position 22 of the second framework region of the light chain variable region of said monoclonal antibody comprising a light chain variable region comprising the amino acid sequence of SEQ ID NO:21 and a heavy chain variable region comprising the amino acid sequence of SEQ ID NO:18.

* * * * *

SEQUENCE LISTING

<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 1
ggattttcag gtgcagattt tcag                                              24

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 2
actggatggt gggaagatgg a                                                 21

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (2)..(2)
<223> OTHER INFORMATION: n = g or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (6)..(6)
<223> OTHER INFORMATION: n = a or c
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (15)..(15)
<223> OTHER INFORMATION: n = c or g

<400> SEQUENCE: 3
angtnnagct ncagnagtc                                                    19

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n = a or g
<220> FEATURE:
<221> NAME/KEY: misc_feature
<222> LOCATION: (17)..(17)
<223> OTHER INFORMATION: n = g or a

```
<220> FEATURE:
<221> NAME/KEY: misc_feature
<222> LOCATION: (18)..(18)
<223> OTHER INFORMATION: n = a or t

<400> SEQUENCE: 4
tnccttgncc ccagtannc                                              19

<210> SEQ ID NO 5
<211> LENGTH: 859
<212> TYPE: PRT
<213> ORGANISM: Mus musculus

<400> SEQUENCE: 5
```

| | | | | | | | | | | | | | | | |
|---|---|---|---|---|---|---|---|---|---|---|---|---|---|---|---|
| Met | Glu | Gln | Thr | Glu | Gly | Val | Ser | Thr | Glu | Cys | Ala | Lys | Ala | Ile | Lys |
| 1 | | | | 5 | | | | | 10 | | | | | 15 | |
| Pro | Ile | Asp | Gly | Lys | Ser | Val | His | Gln | Ile | Cys | Ser | Gly | Gln | Val | Ile |
| | | | 20 | | | | | 25 | | | | | 30 | | |
| Leu | Ser | Leu | Ser | Thr | Ala | Val | Lys | Glu | Leu | Ile | Glu | Asn | Ser | Val | Asp |
| | | 35 | | | | | 40 | | | | | 45 | | | |
| Ala | Gly | Ala | Thr | Thr | Ile | Asp | Leu | Arg | Leu | Lys | Asp | Tyr | Gly | Val | Asp |
| | 50 | | | | | 55 | | | | | 60 | | | | |
| Leu | Ile | Glu | Val | Ser | Asp | Asn | Gly | Cys | Gly | Val | Glu | Glu | Asn | Phe |  |
| 65 | | | | | 70 | | | | | 75 | | | | | 80 |
| Glu | Gly | Leu | Ala | Leu | Lys | His | His | Thr | Ser | Lys | Ile | Gln | Glu | Phe | Ala |
| | | | | 85 | | | | | 90 | | | | | 95 | |
| Asp | Leu | Thr | Gln | Val | Glu | Thr | Phe | Gly | Phe | Arg | Gly | Glu | Ala | Leu | Ser |
| | | | 100 | | | | | 105 | | | | | 110 | | |
| Ser | Leu | Cys | Ala | Leu | Ser | Asp | Val | Thr | Ile | Ser | Thr | Cys | His | Gly | Ser |
| | | 115 | | | | | 120 | | | | | 125 | | | |
| Ala | Ser | Val | Gly | Thr | Arg | Leu | Val | Phe | Asp | His | Asn | Gly | Lys | Ile | Thr |
| | 130 | | | | | 135 | | | | | 140 | | | | |
| Gln | Lys | Thr | Pro | Tyr | Pro | Arg | Pro | Lys | Gly | Thr | Thr | Val | Ser | Val | Gln |
| 145 | | | | | 150 | | | | | 155 | | | | | 160 |
| His | Leu | Phe | Tyr | Thr | Leu | Pro | Val | Arg | Tyr | Lys | Glu | Phe | Gln | Arg | Asn |
| | | | | 165 | | | | | 170 | | | | | 175 | |
| Ile | Lys | Lys | Glu | Tyr | Ser | Lys | Met | Val | Gln | Val | Leu | Gln | Ala | Tyr | Cys |
| | | | 180 | | | | | 185 | | | | | 190 | | |
| Ile | Ile | Ser | Ala | Gly | Val | Arg | Val | Ser | Cys | Thr | Asn | Gln | Leu | Gly | Gln |
| | | 195 | | | | | 200 | | | | | 205 | | | |
| Gly | Lys | Arg | His | Ala | Val | Val | Cys | Thr | Ser | Gly | Thr | Ser | Gly | Met | Lys |
| | 210 | | | | | 215 | | | | | 220 | | | | |
| Glu | Asn | Ile | Gly | Ser | Val | Phe | Gly | Gln | Lys | Gln | Leu | Gln | Ser | Leu | Ile |
| 225 | | | | | 230 | | | | | 235 | | | | | 240 |
| Pro | Phe | Val | Gln | Leu | Pro | Pro | Ser | Asp | Ala | Val | Cys | Glu | Glu | Tyr | Gly |
| | | | | 245 | | | | | 250 | | | | | 255 | |
| Leu | Ser | Thr | Ser | Gly | Arg | His | Lys | Thr | Phe | Ser | Thr | Phe | Arg | Ala | Ser |
| | | | 260 | | | | | 265 | | | | | 270 | | |
| Phe | His | Ser | Ala | Arg | Thr | Ala | Pro | Gly | Gly | Val | Gln | Gln | Thr | Gly | Ser |
| | | 275 | | | | | 280 | | | | | 285 | | | |
| Phe | Ser | Ser | Ser | Ile | Arg | Gly | Pro | Val | Thr | Gln | Gln | Arg | Ser | Leu | Ser |
| | 290 | | | | | 295 | | | | | 300 | | | | |
| Leu | Ser | Met | Arg | Phe | Tyr | His | Met | Tyr | Asn | Arg | His | Gln | Tyr | Pro | Phe |
| 305 | | | | | 310 | | | | | 315 | | | | | 320 |
| Val | Val | Leu | Asn | Val | Ser | Val | Asp | Ser | Glu | Cys | Val | Asp | Ile | Asn | Val |
| | | | | 325 | | | | | 330 | | | | | 335 | |

```
Thr Pro Asp Lys Arg Gln Ile Leu Leu Gln Glu Glu Lys Leu Leu Leu
        340                 345                 350

Ala Val Leu Lys Thr Ser Leu Ile Gly Met Phe Asp Ser Asp Ala Asn
        355                 360                 365

Lys Leu Asn Val Asn Gln Gln Pro Leu Leu Asp Val Glu Gly Asn Leu
        370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
            420                 425                 430

Ile Lys Ser Arg Gly Pro Glu Thr Ala Glu Leu Thr Arg Ser Phe Pro
                435                 440                 445

Ser Glu Lys Arg Gly Val Leu Ser Ser Tyr Pro Ser Asp Val Ile Ser
        450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
                485                 490                 495

Leu Ser Ser Thr Ser Ala Gly Ser Glu Glu Phe Ser Thr Pro Glu
            500                 505                 510

Val Ala Ser Ser Phe Ser Ser Asp Tyr Asn Val Ser Ser Leu Glu Asp
            515                 520                 525

Arg Pro Ser Gln Glu Thr Ile Asn Cys Gly Asp Leu Asp Cys Arg Pro
        530                 535                 540

Pro Gly Thr Gly Gln Ser Leu Lys Pro Glu Asp His Gly Tyr Gln Cys
545                 550                 555                 560

Lys Ala Leu Pro Leu Ala Arg Leu Ser Pro Thr Asn Ala Lys Arg Phe
                565                 570                 575

Lys Thr Glu Glu Arg Pro Ser Asn Val Asn Ile Ser Gln Arg Leu Pro
            580                 585                 590

Gly Pro Gln Ser Thr Ser Ala Ala Glu Val Asp Val Ala Ile Lys Met
        595                 600                 605

Asn Lys Arg Ile Val Leu Leu Glu Phe Ser Leu Ser Leu Ala Lys
        610                 615                 620

Arg Met Lys Gln Leu Gln His Leu Lys Ala Gln Asn Lys His Glu Leu
625                 630                 635                 640

Ser Tyr Arg Lys Phe Arg Ala Lys Ile Cys Pro Gly Glu Asn Gln Ala
                645                 650                 655

Ala Glu Asp Glu Leu Arg Lys Glu Ile Ser Lys Ser Met Phe Ala Glu
            660                 665                 670

Met Glu Ile Leu Gly Gln Phe Asn Leu Gly Phe Ile Val Thr Lys Leu
        675                 680                 685

Lys Glu Asp Leu Phe Leu Val Asp Gln His Ala Ala Asp Glu Lys Tyr
        690                 695                 700

Asn Phe Glu Met Leu Gln Gln His Thr Val Leu Gln Ala Gln Arg Leu
705                 710                 715                 720

Ile Thr Pro Gln Thr Leu Asn Leu Thr Ala Val Asn Glu Ala Val Leu
                725                 730                 735

Ile Glu Asn Leu Glu Ile Phe Arg Lys Asn Gly Phe Asp Phe Val Ile
            740                 745                 750
```

```
Asp Glu Asp Ala Pro Val Thr Glu Arg Ala Lys Leu Ile Ser Leu Pro
        755                 760                 765
Thr Ser Lys Asn Trp Thr Phe Gly Pro Gln Asp Ile Asp Glu Leu Ile
        770                 775                 780
Phe Met Leu Ser Asp Ser Pro Gly Val Met Cys Arg Pro Ser Arg Val
785                 790                 795                 800
Arg Gln Met Phe Ala Ser Arg Ala Cys Arg Lys Ser Val Met Ile Gly
                805                 810                 815
Thr Ala Leu Asn Ala Ser Glu Met Lys Lys Leu Ile Thr His Met Gly
                820                 825                 830
Glu Met Asp His Pro Trp Asn Cys Pro His Gly Arg Pro Thr Met Arg
                835                 840                 845
His Val Ala Asn Leu Asp Val Ile Ser Gln Asn
        850                 855

<210> SEQ ID NO 6
<211> LENGTH: 3056
<212> TYPE: DNA
<213> ORGANISM: Mus musculus

<400> SEQUENCE: 6
gaattccggt gaaggtcctg aagaatttcc agattcctga gtatcattgg aggagacaga      60
taacctgtcg tcaggtaacg atggtgtata tgcaacagaa atgggtgttc ctggagacgc     120
gtcttttccc gagagcggca ccgcaactct cccgcggtga ctgtgactgg aggagtcctg     180
catccatgga gcaaaccgaa ggcgtgagta cagaatgtgc taaggccatc aagcctattg     240
atgggaagtc agtccatcaa atttgttctg gcaggtgat actcagttta agcaccgctg      300
tgaaggagtt gatagaaaat agtgtagatg ctggtgctac tactattgat ctaaggctta     360
aagactatgg ggtggacctc attgaagttt cagacaatgg atgtggggta agaagaaa      420
actttgaagg tctagctctg aaacatcaca catctaagat tcaagagttt gccgacctca     480
cgcaggttga aactttcggc tttcgggggg aagctctgag ctctctgtgt gcactaagtg     540
atgtcactat atctacctgc cacgggtctg caagcgttgg gactcgactg gtgtttgacc     600
ataatgggaa atcacccag aaaactccct accccgacc taaggaacc acagtcagtg       660
tgcagcactt attttataca ctacccgtgc gttacaaaga gttcagagg aacattaaaa      720
aggagtattc caaaatggtg caggtcttac aggcgtactg tatcatctca gcaggcgtcc     780
gtgtaagctg cactaatcag ctcggacagg ggaagcggca cgctgtggtg tgcacaagcg     840
gcacgtctgg catgaaggaa aatatcgggt ctgtgtttgg ccagaagcag ttgcaaagcc     900
tcattccttt tgttcagctg ccccctagta cgctgtgtg tgaagagtac ggcctgagca      960
cttcaggacg ccacaaaacc ttttctacgt ttcgggcttc atttcacagt gcacgcacgg    1020
cgccgggag agtgcaacag acaggcagtt tttcttcatc aatcagaggc cctgtgaccc     1080
agcaaaggtc tctaagcttg tcaatgaggt tttatcacat gtataaccgg catcagtacc    1140
catttgtcgt ccttaacgtt tccgttgact cagaatgtgt ggatattaat gtaactccag    1200
ataaaaggca aattctacta caagaagaga agctattgct ggccgtttta aagacctcct    1260
tgataggaat gtttgacagt gatgcaaaca agcttaatgt caaccagcag ccactgctag    1320
atgttgaagg taacttagta aagctgcata ctgcagaact agaaaagcct gtgccaggaa    1380
agcaagataa ctctccttca ctgaagagca cagcagacga gaaagggta gcatccatct    1440
ccaggctgag agaggccttt tctcttcatc ctactaaaga gatcaagtct aggggtccag   1500
```

-continued

```
agactgctga actgacacgg agttttccaa gtgagaaaag gggcgtgtta tcctcttatc      1560
cttcagacgt catctcttac agaggcctcc gtggctcgca ggacaaattg gtgagtccca      1620
cggacagccc tggtgactgt atggacagag agaaaataga aaagactcag ggctcagca       1680 gcacctcagc tggctctgag aagagttca gcaccccaga agtggccagt agctttagca       1740
gtgactataa cgtgagctcc ctagaagaca gaccttctca ggaaaccata aactgtggtg      1800
acctggactg ccgtcctcca ggtacaggac agtccttgaa gccagaagac catggatatc     1860
aatgcaaagc tctacctcta gctcgtctgt cacccacaaa tgccaagcgc ttcaagacag      1920
aggaaagacc ctcaaatgtc aacatttctc aaagattgcc tggtcctcag agcacctcag     1980
cagctgaggt cgatgtagcc ataaaaatga ataagagaat cgtgctcctc gagttctctc     2040
tgagttctct agctaagcga atgaagcagt tacagcacct aaaggcgcag aacaaacatg     2100
aactgagtta cagaaaattt agggccaaga tttgccctgg agaaaaccaa gcagcagaag     2160
atgaactcag aaaagagatt agtaaatcga tgtttgcaga gatggagatc ttgggtcagt    2220
ttaacctggg atttatagta accaaactga agaggacct cttcctggtg gaccagcatg     2280
ctgcggatga aagtacaac tttgagatgc tgcagcagca cacggtgctc caggcgcaga     2340
ggctcatcac accccagact ctgaacttaa ctgctgtcaa tgaagctgta ctgatagaaa    2400
atctggaaat attcagaaag aatggctttg actttgtcat tgatgaggat gctccagtca   2460
ctgaaagggc taaattgatt tccttaccaa ctagtaaaaa ctggaccttt ggaccccaag     2520
atatagatga actgatcttt atgttaagtg acagccctgg ggtcatgtgc cggccctcac    2580
gagtcagaca gatgtttgct tccagagcct gtcggaagtc agtgatgatt ggaacggcgc    2640
tcaatgcgag cgagatgaag aagctcatca cccacatggg tgagtggac caccctgga      2700 actgccccca cggcaggcca accatgaggc acgttgccaa tctggatgtc atctctcaga    2760
actgacacac cccttgtagc atagagttta ttacagattg ttcggtttgc aaagagaagg    2820
ttttaagtaa tctgattatc gttgtacaaa aattagcatg ctgctttaat gtactggatc    2880
catttaaaag cagtgttaag gcaggcatga tggagtgttc ctctagctca gctacttggg    2940
tgatccggtg ggagctcatg tgagcccagg actttgagac cactccgagc acattcatg     3000 agactcaatt caaggacaaa aaaaaaaaga tatttttgaa gccttttaaa aaaaaa        3056
```

<210> SEQ ID NO 7
<211> LENGTH: 862
<212> TYPE: PRT
<213> ORGANISM: Homo sapiens

<400> SEQUENCE: 7

```
Met Glu Arg Ala Glu Ser Ser Thr Glu Pro Ala Lys Ala Ile Lys
1               5                   10                  15

Pro Ile Asp Arg Lys Ser Val His Gln Ile Cys Ser Gly Gln Val Val
                20                  25                  30

Leu Ser Leu Ser Thr Ala Val Lys Glu Leu Val Glu Asn Ser Leu Asp
            35                  40                  45

Ala Gly Ala Thr Asn Ile Asp Leu Lys Leu Lys Asp Tyr Gly Val Asp
        50                  55                  60

Leu Ile Glu Val Ser Asp Asn Gly Cys Gly Val Glu Glu Glu Asn Phe
    65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
```

-continued

```
                    100                 105                 110
Ser Leu Cys Ala Leu Ser Asp Val Thr Ile Ser Thr Cys His Ala Ser
            115                 120                 125
Ala Lys Val Gly Thr Arg Leu Met Phe Asp His Asn Gly Lys Ile Ile
            130                 135                 140
Gln Lys Thr Pro Tyr Pro Arg Pro Arg Gly Thr Thr Val Ser Val Gln
145                 150                 155                 160
Gln Leu Phe Ser Thr Leu Pro Val Arg His Lys Glu Phe Gln Arg Asn
                165                 170                 175
Ile Lys Lys Glu Tyr Ala Lys Met Val Gln Val Leu His Ala Tyr Cys
            180                 185                 190
Ile Ile Ser Ala Gly Ile Arg Val Ser Cys Thr Asn Gln Leu Gly Gln
            195                 200                 205
Gly Lys Arg Gln Pro Val Val Cys Thr Gly Gly Ser Pro Ser Ile Lys
            210                 215                 220
Glu Asn Ile Gly Ser Val Phe Gly Gln Lys Leu Gln Ser Leu Ile
225                 230                 235                 240
Pro Phe Val Gln Leu Pro Pro Ser Asp Ser Val Cys Glu Glu Tyr Gly
                245                 250                 255
Leu Ser Cys Ser Asp Ala Leu His Asn Leu Phe Tyr Ile Ser Gly Phe
            260                 265                 270
Ile Ser Gln Cys Thr His Gly Val Gly Arg Ser Ser Thr Asp Arg Gln
            275                 280                 285
Phe Phe Phe Ile Asn Arg Arg Pro Cys Asp Pro Ala Lys Val Cys Arg
            290                 295                 300
Leu Val Asn Glu Val Tyr His Met Tyr Asn Arg His Gln Tyr Pro Phe
305                 310                 315                 320
Val Val Leu Asn Ile Ser Val Asp Ser Glu Cys Val Asp Ile Asn Val
                325                 330                 335
Thr Pro Asp Lys Arg Gln Ile Leu Leu Gln Glu Glu Lys Leu Leu Leu
            340                 345                 350
Ala Val Leu Lys Thr Ser Leu Ile Gly Met Phe Asp Ser Asp Val Asn
            355                 360                 365
Lys Leu Asn Val Ser Gln Gln Pro Leu Leu Asp Val Glu Gly Asn Leu
            370                 375                 380
Ile Lys Met His Ala Ala Asp Leu Glu Lys Pro Met Val Glu Lys Gln
385                 390                 395                 400
Asp Gln Ser Pro Ser Leu Arg Thr Gly Glu Lys Lys Asp Val Ser
                405                 410                 415
Ile Ser Arg Leu Arg Glu Ala Phe Ser Leu Arg His Thr Thr Glu Asn
            420                 425                 430
Lys Pro His Ser Pro Lys Thr Pro Glu Pro Arg Arg Ser Pro Leu Gly
            435                 440                 445
Gln Lys Arg Gly Met Leu Ser Ser Thr Ser Gly Ala Ile Ser Asp
            450                 455                 460
Lys Gly Val Leu Arg Pro Gln Lys Glu Ala Val Ser Ser Ser His Gly
465                 470                 475                 480
Pro Ser Asp Pro Thr Asp Arg Ala Glu Val Glu Lys Asp Ser Gly His
                485                 490                 495
Gly Ser Thr Ser Val Asp Ser Glu Gly Phe Ser Ile Pro Asp Thr Gly
            500                 505                 510
Ser His Cys Ser Ser Glu Tyr Ala Ala Ser Ser Pro Gly Asp Arg Gly
            515                 520                 525
```

-continued

```
Ser Gln Glu His Val Asp Ser Gln Glu Lys Ala Pro Glu Thr Asp Asp
    530                 535                 540
Ser Phe Ser Asp Val Asp Cys His Ser Asn Gln Glu Asp Thr Gly Cys
545                 550                 555                 560
Lys Phe Arg Val Leu Pro Gln Pro Thr Asn Leu Ala Thr Pro Asn Thr
                565                 570                 575
Lys Arg Phe Lys Lys Glu Glu Ile Leu Ser Ser Asp Ile Cys Gln
            580                 585                 590
Lys Leu Val Asn Thr Gln Asp Met Ser Ala Ser Gln Val Asp Val Ala
        595                 600                 605
Val Lys Ile Asn Lys Lys Val Val Pro Leu Asp Phe Ser Met Ser Ser
    610                 615                 620
Leu Ala Lys Arg Ile Lys Gln Leu His His Glu Ala Gln Gln Ser Glu
625                 630                 635                 640
Gly Glu Gln Asn Tyr Arg Lys Phe Arg Ala Lys Ile Cys Pro Gly Glu
                645                 650                 655
Asn Gln Ala Ala Glu Asp Glu Leu Arg Lys Glu Ile Ser Lys Thr Met
            660                 665                 670
Phe Ala Glu Met Glu Ile Ile Gly Gln Phe Asn Leu Gly Phe Ile Ile
        675                 680                 685
Thr Lys Leu Asn Glu Asp Ile Phe Ile Val Asp Gln His Ala Thr Asp
    690                 695                 700
Glu Lys Tyr Asn Phe Glu Met Leu Gln Gln His Thr Val Leu Gln Gly
705                 710                 715                 720
Gln Arg Leu Ile Ala Pro Gln Thr Leu Asn Leu Thr Ala Val Asn Glu
                725                 730                 735
Ala Val Leu Ile Glu Asn Leu Glu Ile Phe Arg Lys Asn Gly Phe Asp
            740                 745                 750
Phe Val Ile Asp Glu Asn Ala Pro Val Thr Glu Arg Ala Lys Leu Ile
        755                 760                 765
Ser Leu Pro Thr Ser Lys Asn Trp Thr Phe Gly Pro Gln Asp Val Asp
    770                 775                 780
Glu Leu Ile Phe Met Leu Ser Asp Ser Pro Gly Val Met Cys Arg Pro
785                 790                 795                 800
Ser Arg Val Lys Gln Met Phe Ala Ser Arg Ala Cys Arg Lys Ser Val
                805                 810                 815
Met Ile Gly Thr Ala Leu Asn Thr Ser Glu Met Lys Lys Leu Ile Thr
            820                 825                 830
His Met Gly Glu Met Asp His Pro Trp Asn Cys Pro His Gly Arg Pro
        835                 840                 845
Thr Met Arg His Ile Ala Asn Leu Gly Val Ile Ser Gln Asn
    850                 855                 860

<210> SEQ ID NO 8
<211> LENGTH: 2771
<212> TYPE: DNA
<213> ORGANISM: Homo sapiens

<400> SEQUENCE: 8
cgaggcggat cgggtgttgc atccatggag cgagctgaga gctcgagtac agaacctgct   60
aaggccatca aacctattga tcggaagtca gtccatcaga tttgctctgg gcaggtggta  120
ctgagtctaa gcactgcggt aaaggagtta gtagaaaaca gtctggatgc tggtgccact  180
aatattgatc taaagcttaa ggactatgga gtggatctta ttgaagtttc agacaatgga  240
```

```
tgtggggtag aagaagaaaa cttcgaaggc ttaactctga aacatcacac atctaagatt      300
caagagtttg ccgacctaac tcaggttgaa acttttggct ttcgggggga agctctgagc      360
tcactttgtg cactgagcga tgtcaccatt tctacctgcc acgcatcggc gaaggttgga      420
actcgactga tgtttgatca caatgggaaa attatccaga aaaccccta ccccgcccc        480 agagggacca cagtcagcgt gcagcagtta ttttccacac tacctgtgcg ccataaggaa      540
tttcaaagga atattaagaa ggagtatgcc aaaatggtcc aggtcttaca tgcatactgt      600
atcatttcag caggcatccg tgtaagttgc accaatcagc ttggacaagg aaaacgacag      660
cctgtggtat gcacaggtgg aagccccagc ataaggaaa atatcggctc tgtgtttggg       720
cagaagcagt tgcaaagcct cattcctttt gttcagctgc ccctagtga ctccgtgtgt       780 gaagagtacg gtttgagctg ttcggatgct ctgcataatc ttttttacat ctcaggtttc      840
atttcacaat gcacgcatgg agttggaagg agttcaacag acagacagtt tttctttatc      900
aaccggcggc cttgtgaccc agcaaaggtc tgcagactcg tgaatgaggt ctaccacatg      960
tataatcgac accagtatcc atttgttgtt cttaacattt ctgttgattc agaatgcgtt     1020
gatatcaatg ttactccaga taaaaggcaa attttgctac aagaggaaaa gcttttgttg     1080
gcagttttaa agacctcttt gataggaatg tttgatagtg atgtcaacaa gctaaatgtc     1140
agtcagcagc cactgctgga tgttgaaggt aacttaataa aaatgcatgc agcggatttg     1200
gaaaagccca tggtagaaaa gcaggatcaa tcccccttcat taaggactgg agaagaaaaa     1260
aaagacgtgt ccatttccag actgcgagag gccttttctc ttcgtcacac aacagagaac     1320
aagcctcaca gcccaaagac tccagaacca agaaggagcc ctctaggaca gaaaaggggt     1380
atgctgtctt ctagcacttc aggtgccatc tctgacaaag gcgtcctgag acctcagaaa     1440
gaggcagtga gttccagtca cggacccagt gaccctacgg acagagcgga ggtggagaag     1500
gactcggggc acggcagcac ttccgtggat tctgaggggt tcagcatccc agacacgggc     1560
agtcactgca gcagcgagta tgcggccagc tccccagggg acaggggctc gcaggaacat     1620
gtggactctc aggagaaagc gcctgaaact gacgactctt tttcagatgt ggactgccat     1680
tcaaaccagg aagataccgg atgtaaattt cgagttttgc ctcagccaac taatctcgca     1740
accccaaaca caaagcgttt taaaaaagaa gaaattcttt ccagttctga catttgtcaa     1800
aagttagtaa atactcagga catgtcagcc tctcaggttg atgtagctgt gaaaattaat     1860
aagaaagttg tgcccctgga cttttctatg agttctttag ctaaacgaat aaagcagtta     1920
catcatgaag cacagcaaag tgaaggggaa cagaattaca ggaagtttag ggcaaagatt     1980
tgtcctggag aaaatcaagc agccgaagat gaactaagaa aagagataag taaaacgatg     2040
tttgcagaaa tggaaatcat tggtcagttt aacctgggat ttataataac caaactgaat     2100
gaggatatct tcatagtgga ccagcatgcc acggacgaga gtataacctt cgagatgctg     2160
cagcagcaca ccgtgctcca ggggcagagg ctcatagcac ctcagactct caacttaact     2220
gctgttaatg aagctgttct gatagaaaat ctggaaatat ttagaaagaa tggctttgat     2280
tttgttatcg atgaaaatgc tccagtcact gaaagggcta aactgatttc cttgccaact     2340
agtaaaaact ggaccttcgg accccaggac gtcgatgaac tgatcttcat gctgagcgac     2400
agccctgggg tcatgtgccg gccttcccga gtcaagcaga tgtttgcctc cagagcctgc     2460
cggaagtcgg tgatgattgg gactgctctt aacacaagcg agatgaagaa actgatcacc     2520
cacatggggg agatggacca cccctggaac tgtccccatg gaaggccaac catgagacac     2580
```

-continued

```
atcgccaacc tgggtgtcat ttctcagaac tgaccgtagt cactgtatgg aataattggt    2640
tttatcgcag attttatgt tttgaaagac agagtcttca ctaaccttt tgttttaaa      2700 atgaaacctg ctacttaaaa aaatacaca tcacacccat ttaaaagtga tcttgagaac    2760
cttttcaaac c                                                        2771
```

<210> SEQ ID NO 9
<211> LENGTH: 932
<212> TYPE: PRT
<213> ORGANISM: Homo sapiens

<400> SEQUENCE: 9

```
Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
65                  70                  75                  80

His Glu Asp Leu Glu Asn Leu Thr Thr Tyr Gly Phe Arg Gly Glu Ala
                85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys Pro Ser His Leu Gly Gln Gly Thr Thr Val Thr
    130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
            180                 185                 190

Asn Lys Ala Val Ile Trp Gln Lys Ser Arg Val Ser Asp His Lys Met
        195                 200                 205

Ala Leu Met Ser Val Leu Gly Thr Ala Val Met Asn Asn Met Glu Ser
    210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
            260                 265                 270

Leu Lys Leu Ile Arg His His Tyr Asn Leu Lys Cys Leu Lys Glu Ser
        275                 280                 285

Thr Arg Leu Tyr Pro Val Phe Phe Leu Lys Ile Asp Val Pro Thr Ala
    290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335
```

```
Tyr Gly Pro Leu Pro Ser Thr Asn Ser Tyr Glu Asn Asn Lys Thr Asp
                340                 345                 350

Val Ser Ala Ala Asp Ile Val Leu Ser Lys Thr Ala Glu Thr Asp Val
            355                 360                 365

Leu Phe Asn Lys Val Glu Ser Ser Gly Lys Asn Tyr Ser Asn Val Asp
        370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
            420                 425                 430

Lys Asn Ala Phe Gln Asp Ile Ser Met Ser Asn Val Ser Trp Glu Asn
        435                 440                 445

Ser Gln Thr Glu Tyr Ser Lys Thr Cys Phe Ile Ser Ser Val Lys His
    450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Ser Glu Ile Ser Ala Asp
                485                 490                 495

Glu Trp Ser Arg Gly Asn Ile Leu Lys Asn Ser Val Gly Glu Asn Ile
            500                 505                 510

Glu Pro Val Lys Ile Leu Val Pro Glu Lys Ser Leu Pro Cys Lys Val
        515                 520                 525

Ser Asn Asn Asn Tyr Pro Ile Pro Glu Gln Met Asn Leu Asn Glu Asp
    530                 535                 540

Ser Cys Asn Lys Lys Ser Asn Val Ile Asp Asn Lys Ser Gly Lys Val
545                 550                 555                 560

Thr Ala Tyr Asp Leu Leu Ser Asn Arg Val Ile Lys Lys Pro Met Ser
                565                 570                 575

Ala Ser Ala Leu Phe Val Gln Asp His Arg Pro Gln Phe Leu Ile Glu
            580                 585                 590

Asn Pro Lys Thr Ser Leu Glu Asp Ala Thr Leu Gln Ile Glu Glu Leu
        595                 600                 605

Trp Lys Thr Leu Ser Glu Glu Lys Leu Lys Tyr Glu Glu Lys Ala
    610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Arg Lys Ile Lys Pro
                645                 650                 655

Thr Ser Ala Trp Asn Leu Ala Gln Lys His Lys Leu Lys Thr Ser Leu
            660                 665                 670

Ser Asn Gln Pro Lys Leu Asp Glu Leu Leu Gln Ser Gln Ile Glu Lys
        675                 680                 685

Arg Arg Ser Gln Asn Ile Lys Met Val Gln Ile Pro Phe Ser Met Lys
    690                 695                 700

Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
                725                 730                 735

Leu Met Thr Ser Lys Thr Glu Val Met Leu Leu Asn Pro Tyr Arg Val
            740                 745                 750

Glu Glu Ala Leu Leu Phe Lys Arg Leu Leu Glu Asn His Lys Leu Pro
```

```
            755                 760                 765
Ala Glu Pro Leu Glu Lys Pro Ile Met Leu Thr Glu Ser Leu Phe Asn
    770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
                805                 810                 815

Gly Phe Lys Ile Lys Leu Ile Pro Gly Val Ser Ile Thr Glu Asn Tyr
                820                 825                 830

Leu Glu Ile Glu Gly Met Ala Asn Cys Leu Pro Phe Tyr Gly Val Ala
                835                 840                 845

Asp Leu Lys Glu Ile Leu Asn Ala Ile Leu Asn Arg Asn Ala Lys Glu
    850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
                885                 890                 895

Ile Gln Asp Ile Ile Tyr Arg Met Lys His Gln Phe Gly Asn Glu Ile
                900                 905                 910

Lys Glu Cys Val His Gly Arg Pro Phe Phe His His Leu Thr Tyr Leu
                915                 920                 925

Pro Glu Thr Thr
    930

<210> SEQ ID NO 10
<211> LENGTH: 3063
<212> TYPE: DNA
<213> ORGANISM: Homo sapiens

<400> SEQUENCE: 10
ggcacgagtg gctgcttgcg gctagtggat ggtaattgcc tgcctcgcgc tagcagcaag      60
ctgctctgtt aaaagcgaaa atgaacaat tgcctgcggc aacagttcga ctcctttcaa      120
gttctcagat catcacttcg gtggtcagtg ttgtaaaaga gcttattgaa actccttgg      180 atgctggtgc cacaagcgta gatgttaaac tggagaacta tggatttgat aaaattgagg      240
tgcgagataa cggggagggt atcaaggctg ttgatgcacc tgtaatggca atgaagtact      300
acacctcaaa ataaatagt catgaagatc ttgaaaattt gacaacttac ggttttcgtg      360
gagaagcctt gggtcaatt tgttgtatag ctgaggtttt aattacaaca gaacggctg      420 ctgataattt tagcacccag tatgttttag atggcagtgg ccacatactt tctcagaaac      480
cttcacatct tggtcaaggt acaactgtaa ctgctttaag attattttaag aatctacctg      540 taagaaagca gttttactca actgcaaaaa aatgtaaaga tgaaataaaa aagatccaag      600
atctcctcat gagctttggt atccttaaac ctgacttaag gattgtcttt gtacataaca      660
aggcagttat ttggcagaaa agcagagtat cagatcacaa gatggctctc atgtcagttc      720
tggggactgc tgttatgaac aatatggaat cctttcagta ccactctgaa gaatctcaga      780
tttatctcag tggatttctt ccaaagtgtg atgcagacca ctctttcact agtctttcaa      840
caccagaaag aagtttcatc ttcataaaca gtcgaccagt acatcaaaaa gatatcttaa      900
agttaatccg acatcattac aatctgaaat gcctaaagga atctactcgt ttgtatcctg      960 ttttcttttct gaaatcgat gttcctacag ctgatgttga tgtaaattta acaccagata     1020
aaagccaagt attattacaa aataaggaat ctgttttaat tgctcttgaa aatctgatga     1080
```

-continued

```
cgacttgtta tggaccatta cctagtacaa attcttatga aaataataaa acagatgttt    1140
ccgcagctga catcgttctt agtaaaacag cagaaacaga tgtgctttt aataaagtgg     1200 aatcatctgg aaagaattat tcaaatgttg atacttcagt cattccattc caaaatgata    1260
tgcataatga tgaatctgga aaaaacactg atgattgttt aaatcaccag ataagtattg    1320
gtgactttgg ttatggtcat tgtagtagtg aaatttctaa cattgataaa aacactaaga    1380
atgcatttca ggacatttca atgagtaatg tatcatggga gaactctcag acggaatata    1440
gtaaaacttg ttttataagt tccgttaagc acacccagtc agaaaatggc aataaagacc    1500
atatagatga gagtggggaa aatgaggaag aagcaggtct tgaaaactct tcggaaattt    1560
ctgcagatga gtggagcagg ggaaatatac ttaaaaattc agtgggagag aatattgaac    1620
ctgtgaaaat tttagtgcct gaaaaaagtt taccatgtaa agtaagtaat aataattatc    1680
caatccctga acaaatgaat cttaatgaag attcatgtaa caaaaaatca aatgtaatag    1740
ataataaatc tggaaaagtt acagcttatg atttacttag caatcgagta atcaagaaac    1800
ccatgtcagc aagtgctctt tttgttcaag atcatcgtcc tcagtttctc atagaaaatc    1860
ctaagactag tttagaggat gcaacactac aaattgaaga actgtggaag acattgagtg    1920
aagaggaaaa actgaaatat gaagagaagg ctactaaaga cttggaacga tacaatagtc    1980
aaatgaagag agccattgaa caggagtcac aaatgtcact aaaagatggc agaaaaaaga    2040 taaacccac cagcgcatgg aatttggccc agaagcacaa gttaaaaacc tcattatcta    2100
atcaaccaaa acttgatgaa ctccttcagt cccaaattga aaaagaagg agtcaaaata    2160 ttaaaatggt acagatcccc ttttctatga aaaacttaaa aataaatttt aagaaacaaa    2220
acaaagttga cttagaagag aaggatgaac cttgcttgat ccacaatctc aggtttcctg    2280
atgcatggct aatgacatcc aaaacagagg taatgttatt aaatccatat agagtagaag    2340
aagccctgct atttaaaaga cttcttgaga atcataaact tcctgcagag ccactggaaa    2400
agccaattat gttaacagag agtcttttta atggatctca ttatttagac gttttatata    2460
aaatgacagc agatgaccaa agatacagtg gatcaactta cctgtctgat cctcgtctta    2520
cagcgaatgg tttcaagata aaattgatac caggagtttc aattactgaa aattacttgg    2580
aaatagaagg aatggctaat tgtctcccat tctatggagt agcagattta aaagaaattc    2640
ttaatgctat attaaacaga aatgcaaagg aagtttatga atgtagacct cgcaaagtga    2700
taagttattt agagggagaa gcagtgcgtc tatccagaca attacccatg tacttatcaa    2760
aagaggacat ccaagacatt atctacagaa tgaagcacca gtttggaaat gaaattaaag    2820
agtgtgttca tggtcgccca ttttttcatc atttaaccta tcttccagaa actacatgat    2880
taaatatgtt taagaagatt agttaccatt gaaattggtt ctgtcataaa acagcatgag    2940
tctggtttta aattatcttt gtattatgtg tcacatggtt attttttaaa tgaggattca    3000
ctgacttgtt tttatattga aaaagttcc acgtattgta gaaaacgtaa ataaactaat     3060
aac                                                                  3063
```

<210> SEQ ID NO 11
<211> LENGTH: 934
<212> TYPE: PRT
<213> ORGANISM: Homo sapiens

<400> SEQUENCE: 11

```
Met Ala Val Gln Pro Lys Glu Thr Leu Gln Leu Glu Ser Ala Ala Glu
1               5                   10                  15
```

-continued

```
Val Gly Phe Val Arg Phe Phe Gln Gly Met Pro Glu Lys Pro Thr Thr
             20                  25                  30
Thr Val Arg Leu Phe Asp Arg Gly Asp Phe Tyr Thr Ala His Gly Glu
         35                  40                  45
Asp Ala Leu Ala Ala Arg Glu Val Phe Lys Thr Gln Gly Val Ile
 50                  55                  60
Lys Tyr Met Gly Pro Ala Gly Ala Lys Asn Leu Gln Ser Val Val Leu
 65                  70                  75                  80
Ser Lys Met Asn Phe Glu Ser Phe Val Lys Asp Leu Leu Val Arg
                 85                  90                  95
Gln Tyr Arg Val Glu Val Tyr Lys Asn Arg Ala Gly Asn Lys Ala Ser
                100                 105                 110
Lys Glu Asn Asp Trp Tyr Leu Ala Tyr Lys Ala Ser Pro Gly Asn Leu
                115                 120                 125
Ser Gln Phe Glu Asp Ile Leu Phe Gly Asn Asn Asp Met Ser Ala Ser
130                 135                 140
Ile Gly Val Val Gly Val Lys Met Ser Ala Val Asp Gly Gln Arg Gln
145                 150                 155                 160
Val Gly Val Gly Tyr Val Asp Ser Ile Gln Arg Lys Leu Gly Leu Cys
                165                 170                 175
Glu Phe Pro Asp Asn Asp Gln Phe Ser Asn Leu Glu Ala Leu Leu Ile
                180                 185                 190
Gln Ile Gly Pro Lys Glu Cys Val Leu Pro Gly Gly Glu Thr Ala Gly
            195                 200                 205
Asp Met Gly Lys Leu Arg Gln Ile Ile Gln Arg Gly Gly Ile Leu Ile
210                 215                 220
Thr Glu Arg Lys Lys Ala Asp Phe Ser Thr Lys Asp Ile Tyr Gln Asp
225                 230                 235                 240
Leu Asn Arg Leu Leu Lys Gly Lys Gly Glu Gln Met Asn Ser Ala
                245                 250                 255
Val Leu Pro Glu Met Glu Asn Gln Val Ala Val Ser Ser Leu Ser Ala
            260                 265                 270
Val Ile Lys Phe Leu Glu Leu Leu Ser Asp Asp Ser Asn Phe Gly Gln
            275                 280                 285
Phe Glu Leu Thr Thr Phe Asp Phe Ser Gln Tyr Met Lys Leu Asp Ile
            290                 295                 300
Ala Ala Val Arg Ala Leu Asn Leu Phe Gln Gly Ser Val Glu Asp Thr
305                 310                 315                 320
Thr Gly Ser Gln Ser Leu Ala Ala Leu Leu Asn Lys Cys Lys Thr Pro
                325                 330                 335
Gln Gly Gln Arg Leu Val Asn Gln Trp Ile Lys Gln Pro Leu Met Asp
            340                 345                 350
Lys Asn Arg Ile Glu Glu Arg Leu Asn Leu Val Glu Ala Phe Val Glu
            355                 360                 365
Asp Ala Glu Leu Arg Gln Thr Leu Gln Glu Asp Leu Leu Arg Arg Phe
370                 375                 380
Pro Asp Leu Asn Arg Leu Ala Lys Lys Phe Gln Arg Gln Ala Ala Asn
385                 390                 395                 400
Leu Gln Asp Cys Tyr Arg Leu Tyr Gln Gly Ile Asn Gln Leu Pro Asn
                405                 410                 415
Val Ile Gln Ala Leu Glu Lys His Glu Gly Lys His Gln Lys Leu Leu
            420                 425                 430
Leu Ala Val Phe Val Thr Pro Leu Thr Asp Leu Arg Ser Asp Phe Ser
```

```
            435                 440                 445
Lys Phe Gln Glu Met Ile Glu Thr Thr Leu Asp Met Asp Gln Val Glu
450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
                485                 490                 495

Ile Ser Ala Ala Arg Asp Leu Gly Leu Asp Pro Gly Lys Gln Ile Lys
                500                 505                 510

Leu Asp Ser Ser Ala Gln Phe Gly Tyr Tyr Phe Arg Val Thr Cys Lys
                515                 520                 525

Glu Glu Lys Val Leu Arg Asn Asn Lys Asn Phe Ser Thr Val Asp Ile
530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Ala Gln Asp Ala
                565                 570                 575

Ile Val Lys Glu Ile Val Asn Ile Ser Ser Gly Tyr Val Glu Pro Met
                580                 585                 590

Gln Thr Leu Asn Asp Val Leu Ala Gln Leu Asp Ala Val Val Ser Phe
                595                 600                 605

Ala His Val Ser Asn Gly Ala Pro Val Pro Tyr Val Arg Pro Ala Ile
                610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
                660                 665                 670

Gly Gly Lys Ser Thr Tyr Ile Arg Gln Thr Gly Val Ile Val Leu Met
                675                 680                 685

Ala Gln Ile Gly Cys Phe Val Pro Cys Glu Ser Ala Glu Val Ser Ile
690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Ile Asp Glu Leu Gly Arg
                740                 745                 750

Gly Thr Ser Thr Tyr Asp Gly Phe Gly Leu Ala Trp Ala Ile Ser Glu
                755                 760                 765

Tyr Ile Ala Thr Lys Ile Gly Ala Phe Cys Met Phe Ala Thr His Phe
                770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
                820                 825                 830

Leu Ala Asn Phe Pro Lys His Val Ile Glu Cys Ala Lys Gln Lys Ala
                835                 840                 845

Leu Glu Leu Glu Glu Phe Gln Tyr Ile Gly Glu Ser Gln Gly Tyr Asp
850                 855                 860
```

```
Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
                900                 905                 910

Ala Glu Val Ile Ala Lys Asn Asn Ser Phe Val Asn Glu Ile Ile Ser
            915                 920                 925

Arg Ile Lys Val Thr Thr
    930

<210> SEQ ID NO 12
<211> LENGTH: 3145
<212> TYPE: DNA
<213> ORGANISM: Homo sapiens

<400> SEQUENCE: 12
```

| | | | | | |
|---|---|---|---|---|---|
| ggcgggaaac | agcttagtgg | gtgtggggtc | gcgcattttc | ttcaaccagg | aggtgaggag | 60 |
| gtttcgacat | ggcggtgcag | ccgaaggaga | cgctgcagtt | ggagagcgcg | gccgaggtcg | 120 |
| gcttcgtgcg | cttctttcag | ggcatgccgg | agaagccgac | caccacagtg | cgccttttcg | 180 |
| accgggcga | cttctatacg | cgcacggcg | aggacgcgct | gctggccgcc | cgggaggtgt | 240 |
| tcaagaccca | gggggtgatc | aagtacatgg | ggccggcagg | agcaaagaat | ctgcagagtg | 300 |
| ttgtgcttag | taaaatgaat | tttgaatctt | ttgtaaaaga | tcttcttctg | gttcgtcagt | 360 |
| atagagttga | agtttataag | aatagagctg | gaaataaggc | atccaaggag | aatgattggt | 420 |
| atttggcata | taaggcttct | cctggcaatc | tctctcagtt | tgaagacatt | ctctttggta | 480 |
| acaatgatat | gtcagcttcc | attggtgttg | tgggtgttaa | aatgtccgca | gttgatggcc | 540 |
| agagacaggt | tggagttggg | tatgtggatt | ccatacagag | gaaactagga | ctgtgtgaat | 600 |
| tccctgataa | tgatcagttc | tccaatcttg | aggctctcct | catccagatt | ggaccaaagg | 660 |
| aatgtgtttt | acccggagga | gagactgctg | gagacatggg | gaaactgaga | cagataattc | 720 |
| aaagaggagg | aattctgatc | acagaaagaa | aaaaagctga | cttttccaca | aaagacattt | 780 |
| atcaggacct | caaccggttg | ttgaaaggca | aaaagggaga | gcagatgaat | agtgctgtat | 840 |
| tgccagaaat | ggagaatcag | gttgcagttt | catcactgtc | tgcggtaatc | aagttttag | 900 |
| aactcttatc | agatgattcc | aactttggac | agtttgaact | gactacttt | gacttcagcc | 960 |
| agtatatgaa | attggatatt | gcagcagtca | gagcccttaa | ccttttttcag | ggttctgttg | 1020 |
| aagataccac | tggctctcag | tctctggctg | ccttgctgaa | taagtgtaaa | accccctcaag | 1080 |
| gacaaagact | tgttaaccag | tggattaagc | agcctctcat | ggataagaac | agaatagagg | 1140 |
| agagattgaa | tttagtggaa | gcttttgtag | aagatgcaga | attgaggcag | actttacaag | 1200 |
| aagatttact | tcgtcgattc | ccagatctta | accgacttgc | caagaagttt | caagacaag | 1260 |
| cagcaaactt | acaagattgt | taccgactct | atcagggtat | aaatcaacta | cctaatgtta | 1320 |
| tacaggctct | ggaaaaacat | gaaggaaaac | accagaaatt | attgttggca | gttttttgtga | 1380 |
| ctcctcttac | tgatcttcgt | tctgacttct | ccaagtttca | ggaaatgata | gaaacaactt | 1440 |
| tagatatgga | tcaggtggaa | accatgaatt | ccttgtaaa | accttcattt | gatcctaatc | 1500 |
| tcagtgaatt | aagagaaata | atgaatgact | ggaaaagaa | gatgcagtca | acattaataa | 1560 |
| gtgcagccag | agatcttggc | ttggaccctg | gcaaacagat | taaactggat | ccagtgcac | 1620 |
| agtttggata | ttactttcgt | gtaacctgta | aggaagaaaa | agtccttcgt | aacaataaaa | 1680 |

```
acttagtac tgtagatatc cagaagaatg gtgttaaatt taccaacagc aaattgactt    1740 cttaaatga agagtatacc aaaaataaaa cagaatatga agaagcccag gatgccattg    1800
ttaaagaaat tgtcaatatt tcttcaggct atgtagaacc aatgcagaca ctcaatgatg    1860
tgttagctca gctagatgct gttgtcagct ttgctcacgt gtcaaatgga gcacctgttc    1920
catatgtacg accagccatt ttggagaaag gacaaggaag aattatatta aaagcatcca    1980
ggcatgcttg tgttgaagtt caagatgaaa ttgcatttat tcctaatgac gtatactttg    2040
aaaaagataa acagatgttc cacatcatta ctggccccaa tatgggaggt aaatcaacat    2100
atattcgaca aactggggtg atagtactca tggcccaaat tgggtgtttt tgtgccatgtg   2160 agtcagcaga agtgtccatt gtggactgca tcttagcccg agtaggggct ggtgacagtc    2220
aattgaaagg agtctccacg ttcatggctg aaatgttgga aactgcttct atcctcaggt    2280
ctgcaaccaa agattcatta ataatcatag atgaattggg aagaggaact tctacctacg    2340
atggatttgg gttagcatgg gctatatcag aatacattgc aacaaagatt ggtgcttttt    2400
gcatgtttgc aacccatttt catgaactta ctgccttggc caatcagata ccaactgtta    2460
ataatctaca tgtcacagca ctcaccactg aagagacctt aactatgctt tatcaggtga    2520
agaaaggtgt ctgtgatcaa agttttggga ttcatgttgc agagcttgct aatttcccta    2580
agcatgtaat agagtgtgct aaacagaaag ccctggaact tgaggagttt cagtatattg    2640
gagaatcgca aggatatgat atcatggaac agcagcaaa gaagtgctat ctggaaagag    2700
agcaaggtga aaaaattatt caggagttcc tgtccaaggt gaaacaaatg ccctttactg    2760
aaatgtcaga agaaaacatc acaataaagt taaaacagct aaaagctgaa gtaatagcaa    2820
agaataatag ctttgtaaat gaaatcattt cacgaataaa agttactacg tgaaaaatcc    2880
cagtaatgga atgaaggtaa tattgataag ctattgtctg taatagtttt atattgtttt    2940
atattaaccc ttttccata gtgttaactg tcagtgccca tgggctatca acttaataag    3000
atatttagta atattttact ttgaggacat tttcaaagat ttttattttg aaaaatgaga    3060
gctgtaactg aggactgttt gcaattgaca taggcaataa taagtgatgt gctgaatttt    3120
ataaataaaa tcatgtagtt tgtgg                                         3145
```

<210> SEQ ID NO 13
<211> LENGTH: 756
<212> TYPE: PRT
<213> ORGANISM: Homo sapiens

<400> SEQUENCE: 13

```
Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110
```

```
Val Thr Ile Thr Thr Lys Thr Ala Asp Gly Lys Cys Ala Tyr Arg Ala
            115                 120                 125
Ser Tyr Ser Asp Gly Lys Leu Lys Ala Pro Pro Lys Pro Cys Ala Gly
        130                 135                 140
Asn Gln Gly Thr Gln Ile Thr Val Glu Asp Leu Phe Tyr Asn Ile Ala
145                 150                 155                 160
Thr Arg Arg Lys Ala Leu Lys Asn Pro Ser Glu Glu Tyr Gly Lys Ile
                165                 170                 175
Leu Glu Val Val Gly Arg Tyr Ser Val His Asn Ala Gly Ile Ser Phe
            180                 185                 190
Ser Val Lys Lys Gln Gly Glu Thr Val Ala Asp Val Arg Thr Leu Pro
        195                 200                 205
Asn Ala Ser Thr Val Asp Asn Ile Arg Ser Ile Phe Gly Asn Ala Val
210                 215                 220
Ser Arg Glu Leu Ile Glu Ile Gly Cys Glu Asp Lys Thr Leu Ala Phe
225                 230                 235                 240
Lys Met Asn Gly Tyr Ile Ser Asn Ala Asn Tyr Ser Val Lys Lys Cys
                245                 250                 255
Ile Phe Leu Leu Phe Ile Asn His Arg Leu Val Glu Ser Thr Ser Leu
            260                 265                 270
Arg Lys Ala Ile Glu Thr Val Tyr Ala Ala Tyr Leu Pro Lys Asn Thr
        275                 280                 285
His Pro Phe Leu Tyr Leu Ser Leu Glu Ile Ser Pro Gln Asn Val Asp
        290                 295                 300
Val Asn Val His Pro Thr Lys His Glu Val His Phe Leu His Glu Glu
305                 310                 315                 320
Ser Ile Leu Glu Arg Val Gln Gln His Ile Glu Ser Lys Leu Leu Gly
                325                 330                 335
Ser Asn Ser Ser Arg Met Tyr Phe Thr Gln Thr Leu Leu Pro Gly Leu
            340                 345                 350
Ala Gly Pro Ser Gly Glu Met Val Lys Ser Thr Thr Ser Leu Thr Ser
        355                 360                 365
Ser Ser Thr Ser Gly Ser Ser Asp Lys Val Tyr Ala His Gln Met Val
370                 375                 380
Arg Thr Asp Ser Arg Glu Gln Lys Leu Asp Ala Phe Leu Gln Pro Leu
385                 390                 395                 400
Ser Lys Pro Leu Ser Ser Gln Pro Gln Ala Ile Val Thr Glu Asp Lys
                405                 410                 415
Thr Asp Ile Ser Ser Gly Arg Ala Arg Gln Gln Asp Glu Glu Met Leu
            420                 425                 430
Glu Leu Pro Ala Pro Ala Glu Val Ala Ala Lys Asn Gln Ser Leu Glu
        435                 440                 445
Gly Asp Thr Thr Lys Gly Thr Ser Glu Met Ser Glu Lys Arg Gly Pro
450                 455                 460
Thr Ser Ser Asn Pro Arg Lys Arg His Arg Glu Asp Ser Asp Val Glu
465                 470                 475                 480
Met Val Glu Asp Asp Ser Arg Lys Glu Met Thr Ala Ala Cys Thr Pro
                485                 490                 495
Arg Arg Arg Ile Ile Asn Leu Thr Ser Val Leu Ser Leu Gln Glu Glu
            500                 505                 510
Ile Asn Glu Gln Gly His Glu Val Leu Arg Glu Met Leu His Asn His
        515                 520                 525
```

```
Ser Phe Val Gly Cys Val Asn Pro Gln Trp Ala Leu Ala Gln His Gln
    530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
        595                 600                 605

Glu Tyr Ile Val Glu Phe Leu Lys Lys Lys Ala Glu Met Leu Ala Asp
    610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
            660                 665                 670

Phe Glu Ser Leu Ser Lys Glu Cys Ala Met Phe Tyr Ser Ile Arg Lys
        675                 680                 685

Gln Tyr Ile Ser Glu Glu Ser Thr Leu Ser Gly Gln Gln Ser Glu Val
    690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
            740                 745                 750

Phe Glu Arg Cys
        755

<210> SEQ ID NO 14
<211> LENGTH: 2484
<212> TYPE: DNA
<213> ORGANISM: Homo sapiens

<400> SEQUENCE: 14
cttggctctt ctggcgccaa aatgtcgttc gtggcagggg ttattcggcg gctggacgag        60
acagtggtga accgcatcgc ggcgggggaa gttatccagc ggccagctaa tgctatcaaa       120
gagatgattg agaactgttt agatgcaaaa tccacaagta ttcaagtgat tgttaaagag       180
ggaggcctga gttgattca gatccaagac aatggcaccg ggatcaggaa agaagatctg       240
gatattgtat gtgaaaggtt cactactagt aaactgcagt cctttgagga tttagccagt       300
atttctacct atggctttcg aggtgaggct ttggccagca taagccatgt ggctcatgtt       360
actattacaa cgaaaacagc tgatggaaag tgtgcataca gagcaagtta ctcagatgga       420
aaactgaaag cccctcctaa accatgtgct ggcaatcaag ggacccagat cacggtggag       480 gaccttttt acaacatagc cacgaggaga aaagctttaa aaaatccaag tgaagaatat       540
gggaaatttt ggaagttgt tggcaggtat tcagtacaca atgcaggcat tagttctca       600 gttaaaaaac aaggagagac agtagctgat gttaggacac tacccaatgc ctcaaccgtg       660
gacaatattc gctccatctt tgaaatgctg ttagtcgag aactgataga aattggatgt       720
gaggataaaa ccctagcctt caaaatgaat ggttacatat ccaatgcaaa ctactcagtg       780
```

-continued

```
aagaagtgca tcttcttact cttcatcaac catcgtctgg tagaatcaac ttccttgaga    840
aaagccatag aaacagtgta tgcagcctat ttgcccaaaa acacacaccc attcctgtac    900
ctcagtttag aaatcagtcc ccagaatgtg gatgttaatg tgcaccccac aaagcatgaa    960
gttcacttcc tgcacgagga gagcatcctg gagcgggtgc agcagcacat cgagagcaag   1020
ctcctgggct ccaattcctc caggatgtac ttcacccaga ctttgctacc aggacttgct   1080
ggccctctg gggagatggt taaatccaca acaagtctga cctcgtcttc tacttctgga   1140
agtagtgata aggtctatgc ccaccagatg gttcgtacag attcccggga acagaagctt   1200
gatgcatttc tgcagcctct gagcaaaccc ctgtccagtc agcccaggc cattgtcaca   1260
gaggataaga cagatatttc tagtggcagg gctaggcagc aagatgagga gatgcttgaa   1320
ctcccagccc ctgctgaagt ggctgccaaa aatcagagct ggaggggga tacaacaaag   1380
gggacttcag aaatgtcaga aagagagga cctacttcca gcaaccccag aaagagacat   1440
cgggaagatt ctgatgtgga aatggtggaa gatgattccc gaaaggaaat gactgcagct   1500
tgtacccccc ggagaaggat cattaacctc actagtgttt tgagtctcca ggaagaaatt   1560
aatgagcagg gacatgaggt tctccgggag atgttgcata accactcctt cgtgggctgt   1620
gtgaatcctc agtgggcctt ggcacagcat caaaccaagt tataccttct caacaccacc   1680
aagcttagtg aagaactgtt ctaccagata tcatttatg attttgccaa ttttggtgtt   1740
ctcaggttat cggagccagc accgctcttt gaccttgcca tgcttgcctt agatagtcca   1800
gagagtggct ggacagagga agatggtccc aaagaaggac ttgctgaata cattgttgag   1860
tttctgaaga agaaggctga gatgcttgca gactatttct ctttggaaat tgatgaggaa   1920
gggaacctga ttggattacc ccttctgatt gacaactatg tgccccttt ggagggactg   1980
cctatcttca ttcttcgact agccactgag gtgaattggg acgaagaaaa ggaatgtttt   2040
gaaagcctca gtaaagaatg cgctatgttc tattccatcc ggaagcagta catatctgag   2100
gagtcgaccc tctcaggcca gcagagtgaa gtgcctggct ccattccaaa ctcctggaag   2160
tggactgtgg aacacattgt ctataaagcc ttgcgctcac acattctgcc tcctaaacat   2220
ttcacagaag atgaaatat cctgcagctt gctaacctgc ctgatctata caaagtcttt   2280
gagaggtgtt aaatatggtt atttatgcac tgtgggatgt gttcttcttt ctctgtattc   2340
cgatacaaag tgttgtatca aagtgtgata tacaaagtgt accaacataa gtgttggtag   2400
cacttaagac ttatacttgc cttctgatag tattcctta tacacagtgg attgattata   2460
aataaataga tgtgtcttaa cata                                          2484
```

<210> SEQ ID NO 15
<211> LENGTH: 133
<212> TYPE: PRT
<213> ORGANISM: Homo sapiens

<400> SEQUENCE: 15

Met Glu Arg Ala Glu Ser Ser Thr Glu Pro Ala Lys Ala Ile Lys
1               5                   10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
        35                  40                  45

Ala Gly Ala Thr Asn Ile Asp Leu Lys Leu Lys Asp Tyr Gly Val Asp
    50                  55                  60

Leu Ile Glu Val Ser Asp Asn Gly Cys Gly Val Glu Glu Glu Asn Phe

Glu Gly Leu Thr Leu Lys His His Thr Ser Lys Ile Gln Glu Phe Ala
        85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr
    130

<210> SEQ ID NO 16
<211> LENGTH: 426
<212> TYPE: DNA
<213> ORGANISM: Homo sapiens

<400> SEQUENCE: 16
cgaggcggat cgggtgttgc atccatggag cgagctgaga gctcgagtac agaacctgct      60
aaggccatca aacctattga tcggaagtca gtccatcaga tttgctctgg caggtggta     120 ctgagtctaa gcactgcggt aaaggagtta gtagaaaaca gtctggatgc tggtgccact    180
aatattgatc taaagcttaa ggactatgga gtggatctta ttgaagtttc agacaatgga    240
tgtggggtag aagaagaaaa cttcgaaggc ttaactctga acatcacac atctaagatt     300 caagagtttg ccgacctaac tcaggttgaa acttttggct ttcgggggga agctctgagc    360
tcactttgtg cactgagcga tgtcaccatt tctacctgcc acgcatcggc gaaggttgga    420
acttga                                                              426

<210> SEQ ID NO 17
<211> LENGTH: 70
<212> TYPE: PRT
<213> ORGANISM: Artificial Sequence
<220> FEATURE:
<223> OTHER INFORMATION: Synthetic construct

<400> SEQUENCE: 17

Leu Gln Gln Ser Gly Pro Glu Leu Gly Lys Pro Gly Thr Ser Val Lys
1               5                   10                  15

Ile Ser Cys Lys Ala Ser Gly Tyr Thr Phe Thr Asn Tyr Gly Met Asn
            20                  25                  30

Trp Val Lys Gln Ala Pro Gly Lys Gly Leu Lys Trp Met Gly Trp Ile
        35                  40                  45

Asn Thr Tyr Thr Gly Glu Pro Thr Tyr Ala Asp Asp Phe Lys Gly Arg
    50                  55                  60

Phe Ala Phe Ser Leu Glu
65                  70

<210> SEQ ID NO 18
<211> LENGTH: 70
<212> TYPE: PRT
<213> ORGANISM: Artificial Sequence
<220> FEATURE:
<223> OTHER INFORMATION: Synthetic construct

<400> SEQUENCE: 18

Leu Gln Gln Ser Gly Ala Glu Leu Val Arg Pro Gly Thr Ser Val Lys
1               5                   10                  15

Ile Ser Cys Lys Ala Ser Gly Tyr Thr Phe Thr Asn Tyr Gly Met Asn
            20                  25                  30

```
Trp Val Lys Gln Ala Pro Gly Lys Gly Leu Lys Trp Met Gly Trp Ile
        35                  40                  45

Asn Thr Tyr Thr Gly Glu Pro Thr Tyr Ala Asp Asp Phe Lys Gly Arg
    50                  55                  60

Phe Ala Phe Ser Leu Glu
65              70

<210> SEQ ID NO 19
<211> LENGTH: 70
<212> TYPE: PRT
<213> ORGANISM: Artificial Sequence
<220> FEATURE:
<223> OTHER INFORMATION: Oligonucleotide primer
<220> FEATURE:
<221> NAME/KEY: MISC_FEATURE
<222> LOCATION: (6)..(6)
<223> OTHER INFORMATION: Xaa = Pro or Ala
<220> FEATURE:
<221> NAME/KEY: MISC_FEATURE
<222> LOCATION: (9)..(9)
<223> OTHER INFORMATION: Xaa = Gly or Val
<220> FEATURE:
<221> NAME/KEY: MISC_FEATURE
<222> LOCATION: (10)..(10)
<223> OTHER INFORMATION: Xaa = Lys or Arg

<400> SEQUENCE: 19

Leu Gln Gln Ser Gly Xaa Glu Leu Xaa Xaa Pro Gly Thr Ser Val Lys
1               5                   10                  15

Ile Ser Cys Lys Ala Ser Gly Tyr Thr Phe Thr Asn Tyr Gly Met Asn
            20                  25                  30

Trp Val Lys Gln Ala Pro Gly Lys Gly Leu Lys Trp Met Gly Trp Ile
        35                  40                  45

Asn Thr Tyr Thr Gly Glu Pro Thr Tyr Ala Asp Asp Phe Lys Gly Arg
    50                  55                  60

Phe Ala Phe Ser Leu Glu
65              70

<210> SEQ ID NO 20
<211> LENGTH: 45
<212> TYPE: PRT
<213> ORGANISM: Artificial Sequence
<220> FEATURE:
<223> OTHER INFORMATION: Synthetic construct

<400> SEQUENCE: 20

Ser Ala Ser Ser Val Ser Ser Tyr Phe His Trp Tyr Gln Gln
1               5                   10                  15

Lys Ser Gly Ala Ser Pro Lys Pro Leu Ile His Arg Thr Ser Asn Leu
            20                  25                  30

Ala Ser Gly Val Pro Ala Arg Phe Ser Gly Ser Gly Ser
        35                  40                  45

<210> SEQ ID NO 21
<211> LENGTH: 45
<212> TYPE: PRT
<213> ORGANISM: Artificial Sequence
<220> FEATURE:
<223> OTHER INFORMATION: Synthetic construct

<400> SEQUENCE: 21

Ser Ala Ser Ser Val Ser Ser Tyr Phe His Trp Tyr Gln Gln
1               5                   10                  15

Lys Ser Gly Ala Ser Leu Lys Pro Leu Ile His Arg Thr Ser Asn Leu
```

```
                    20                  25                  30

Ala Ser Gly Val Pro Ala Arg Phe Ser Gly Ser Gly Ser
        35                  40                  45

<210> SEQ ID NO 22
<211> LENGTH: 45
<212> TYPE: PRT
<213> ORGANISM: Artificial Sequence
<220> FEATURE:
<223> OTHER INFORMATION: Oligonucleotide primer
<220> FEATURE:
<221> NAME/KEY: MISC_FEATURE
<222> LOCATION: (22)..(22)
<223> OTHER INFORMATION: Xaa = Pro or Leu

<400> SEQUENCE: 22

Ser Ala Ser Ser Ser Val Ser Ser Ser Tyr Phe His Trp Tyr Gln Gln
1               5                   10                  15

Lys Ser Gly Ala Ser Xaa Lys Pro Leu Ile His Arg Thr Ser Asn Leu
            20                  25                  30

Ala Ser Gly Val Pro Ala Arg Phe Ser Gly Ser Gly Ser
        35                  40                  45

<210> SEQ ID NO 23
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 23
tttcgcaacg ggtttgccg                                              19

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 24
gtttcagagt taagccttcg                                             20

<210> SEQ ID NO 25
<211> LENGTH: 13
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (6)..(6)
<223> OTHER INFORMATION: n is a, c, g, or t

<400> SEQUENCE: 25
tacgtngaat aat                                                    13

<210> SEQ ID NO 26
<211> LENGTH: 13
<212> TYPE: DNA
<213> ORGANISM: Artificial Sequence
<220> FEATURE:
<223> OTHER INFORMATION: Oligonucleotide primer

<400> SEQUENCE: 26
tacgttgaat aat                                                    13
```

```
<210> SEQ ID NO 27
<211> LENGTH: 63
<212> TYPE: DNA
<213> ORGANISM: Artificial Sequence
<220> FEATURE:
<223> OTHER INFORMATION: Oligonucleotide primer

<400> SEQUENCE: 27
gttggatgtc ctatgaatca agggtttgag ggaagcgcct gacttctgct ggtaccagtg    60
caa                                                                  63

<210> SEQ ID NO 28
<211> LENGTH: 63
<212> TYPE: DNA
<213> ORGANISM: Artificial Sequence
<220> FEATURE:
<223> OTHER INFORMATION: Oligonucleotide primer

<400> SEQUENCE: 28
gttggatgtc ctatgaatca agggtttggg ggaagcgcct gacttctgct ggtaccagtg    60
caa                                                                  63

<210> SEQ ID NO 29
<211> LENGTH: 63
<212> TYPE: DNA
<213> ORGANISM: Artificial Sequence
<220> FEATURE:
<223> OTHER INFORMATION: Consensus sequence

<400> SEQUENCE: 29
gttggatgtc ctatgaatca agggtttgrg ggaagcgcct gacttctgct ggtaccagtg    60
caa                                                                  63

<210> SEQ ID NO 30
<211> LENGTH: 13
<212> TYPE: DNA
<213> ORGANISM: Artificial Sequence
<220> FEATURE:
<223> OTHER INFORMATION: Oligonucleotide primer

<400> SEQUENCE: 30
tacgttgaat aat                                                       13
```